(12) United States Patent
Demario et al.

(10) Patent No.: US 10,265,279 B2
(45) Date of Patent: Apr. 23, 2019

(54) COMBINATIONS OF LSD1 INHIBITORS FOR USE IN THE TREATMENT OF SOLID TUMORS

(71) Applicant: ORYZON GENOMICS, S.A., Madrid (ES)

(72) Inventors: Mark D. Demario, New York, NY (US); Tamara Maes, Cornellà de Llobregat (ES); William E. Pierceall, New York, NY (US); Fiona Mack, New York, NY (US); Serena Lunardi, Cornellà de Llobregat (ES)

(73) Assignee: Oryzon Genomics, S.A., Madrid (ES)

(*) Notice: Subject to any disclaimer, the term of this patent is extended or adjusted under 35 U.S.C. 154(b) by 0 days.

(21) Appl. No.: 15/458,640

(22) Filed: Mar. 14, 2017

(65) Prior Publication Data

US 2017/0281567 A1  Oct. 5, 2017

Related U.S. Application Data

(60) Provisional application No. 62/308,529, filed on Mar. 15, 2016.

(51) Int. Cl.

| | | |
|---|---|---|
| *A61K 31/135* | (2006.01) | |
| *A61K 31/55* | (2006.01) | |
| *A61K 31/551* | (2006.01) | |
| *A61K 31/4402* | (2006.01) | |
| *A61K 31/47* | (2006.01) | |
| *A61K 31/52* | (2006.01) | |
| *A61K 31/404* | (2006.01) | |
| *A61K 31/635* | (2006.01) | |
| *A61K 31/167* | (2006.01) | |
| *A61K 31/4545* | (2006.01) | |
| *A61K 31/496* | (2006.01) | |
| *A61K 31/5377* | (2006.01) | |
| *A61K 31/4745* | (2006.01) | |
| *A61K 31/12* | (2006.01) | |
| *A61K 31/19* | (2006.01) | |
| *A61K 31/282* | (2006.01) | |
| *A61K 31/337* | (2006.01) | |
| *A61K 31/4045* | (2006.01) | |
| *A61K 31/475* | (2006.01) | |
| *A61K 31/495* | (2006.01) | |
| *A61K 31/519* | (2006.01) | |
| *A61K 31/555* | (2006.01) | |
| *A61K 31/704* | (2006.01) | |
| *A61K 31/7068* | (2006.01) | |

(52) U.S. Cl.
CPC .......... *A61K 31/135* (2013.01); *A61K 31/12* (2013.01); *A61K 31/167* (2013.01); *A61K 31/19* (2013.01); *A61K 31/282* (2013.01); *A61K 31/337* (2013.01); *A61K 31/404* (2013.01); *A61K 31/4045* (2013.01); *A61K 31/4402* (2013.01); *A61K 31/4545* (2013.01); *A61K 31/47* (2013.01); *A61K 31/475* (2013.01); *A61K 31/4745* (2013.01); *A61K 31/495* (2013.01); *A61K 31/496* (2013.01); *A61K 31/519* (2013.01); *A61K 31/52* (2013.01); *A61K 31/5377* (2013.01); *A61K 31/55* (2013.01); *A61K 31/551* (2013.01); *A61K 31/555* (2013.01); *A61K 31/635* (2013.01); *A61K 31/704* (2013.01); *A61K 31/7068* (2013.01)

(58) Field of Classification Search
CPC .. A61K 31/135; A61K 31/52; A61K 31/4545; A61K 31/167; A61K 31/635; A61K 31/404; A61K 31/496; A61K 31/47; A61K 31/4402; A61K 31/551; A61K 31/55; A61K 31/5377; A61K 31/4745
See application file for complete search history.

(56) References Cited

U.S. PATENT DOCUMENTS

| | | | |
|---|---|---|---|
| 2,331,725 | A | 10/1943 | Price et al. |
| 2,802,005 | A | 8/1957 | Heidelberger et al. |
| 3,205,220 | A | 9/1965 | Svoboda et al. |
| 4,058,519 | A | 11/1977 | Arcamone et al. |
| 4,814,470 | A | 3/1989 | Colin et al. |
| 4,857,653 | A | 8/1989 | Colin et al. |
| 5,712,274 | A | 1/1998 | Sueoka et al. |
| 6,121,451 | A | 9/2000 | Henegar et al. |
| 8,524,717 | B2 | 9/2013 | Guibourt et al. |
| 8,722,743 | B2 | 5/2014 | Ortega-Munoz et al. |
| 8,859,555 | B2 | 10/2014 | Ortega-Muñoz et al. |
| 8,946,296 | B2 | 2/2015 | Ortega Muñoz et al. |

(Continued)

FOREIGN PATENT DOCUMENTS

| | | |
|---|---|---|
| BE | 624076 A1 | 4/1963 |
| CA | 956939 A | 10/1974 |

(Continued)

OTHER PUBLICATIONS

Barlesi et al, "Global histone modifications predict prognosis of resected non small-cell lung cancer",J Clin Oncol,2007,25, 4358-4364.

(Continued)

*Primary Examiner* — Sarah Pihonak
*Assistant Examiner* — Jason Deck
(74) *Attorney, Agent, or Firm* — Finnegan, Henderson, Farabow, Garrett & Dunner, LLP

(57) ABSTRACT

The instant invention relates to therapeutic combinations of LSD1 inhibitors and one or more other active pharmaceutical ingredient(s) or pharmaceutically acceptable salts thereof. The combinations are particularly useful for treating neoplastic diseases, such as cancer, particularly small cell lung cancer (SCLC).

14 Claims, 11 Drawing Sheets

(56) References Cited

U.S. PATENT DOCUMENTS

| | | |
|---|---|---|
| 8,993,808 B2 | 3/2015 | Guibourt et al. |
| 9,006,449 B2 | 4/2015 | Fyfe et al. |
| 9,061,966 B2 | 6/2015 | Castro-Palomino Laria et al. |
| 9,149,447 B2 | 10/2015 | Ortega-Muñoz et al. |
| 9,181,198 B2 | 11/2015 | Ortega-Muñoz et al. |
| 9,186,337 B2 | 11/2015 | Baker et al. |
| 9,469,597 B2 | 10/2016 | Ortega Muñoz et al. |
| 9,487,512 B2 | 11/2016 | Ortega Muñoz et al. |
| 9,616,058 B2 | 4/2017 | Cesar Castro Palomino Laria et al. |
| 9,670,136 B2 | 6/2017 | Ortega-Muñoz et al. |
| 9,676,701 B2 | 6/2017 | Fyfe et al. |
| 9,708,309 B2 | 7/2017 | Ortega-Muñoz et al. |
| 9,790,196 B2 | 10/2017 | Baker et al. |
| 9,908,859 B2 | 3/2018 | Baker et al. |
| 2005/0215610 A1 | 9/2005 | Brodney et al. |
| 2005/0282803 A1 | 12/2005 | Haley et al. |
| 2006/0229289 A1 | 10/2006 | Zhu et al. |
| 2007/0265272 A1 | 11/2007 | Cheng et al. |
| 2008/0139665 A1 | 6/2008 | Schuele et al. |
| 2010/0256201 A1 | 10/2010 | Suzuki et al. |
| 2010/0324147 A1 | 12/2010 | McCafferty et al. |
| 2014/0163041 A1 | 6/2014 | Fyfe et al. |
| 2014/0228405 A1 | 8/2014 | Tomita et al. |
| 2014/0296255 A1 | 10/2014 | Maes et al. |
| 2014/0329833 A1 | 11/2014 | Maes et al. |
| 2015/0266881 A1 | 9/2015 | Tomita et al. |
| 2015/0368186 A1 | 12/2015 | Ortega Muñoz et al. |
| 2016/0000768 A1 | 1/2016 | Castro-Palomino Laria et al. |
| 2016/0039748 A1 | 2/2016 | Suzuki et al. |
| 2016/0045456 A1 | 2/2016 | Guibourt et al. |
| 2016/0081947 A1 | 3/2016 | Maes et al. |
| 2017/0008844 A1 | 1/2017 | Ortega Muñoz et al. |
| 2017/0209432 A1 | 7/2017 | Fyfe et al. |
| 2017/0281566 A1 | 10/2017 | Ciceri et al. |

FOREIGN PATENT DOCUMENTS

| | | | |
|---|---|---|---|
| CH | 514578 A | | 12/1971 |
| CN | 105233292 A | | 1/2016 |
| CN | 105541806 A | | 4/2016 |
| CN | 105924362 A | | 9/2016 |
| CN | 105985265 A | | 10/2016 |
| CN | 106045862 A | | 10/2016 |
| CN | 106045881 A | | 10/2016 |
| DE | 2510866 A1 | | 10/1975 |
| DE | 159877 A1 | | 6/1981 |
| DE | 3231255 A1 | | 3/1983 |
| EP | 0253738 A1 | | 1/1988 |
| EP | 0253739 A1 | | 1/1988 |
| EP | 0321122 A2 | | 6/1989 |
| EP | 0432677 A1 | | 6/1991 |
| EP | 1704859 | | 9/2006 |
| ES | 8604088 A1 | | 6/1986 |
| GB | 2136425 | | 9/1984 |
| JP | H10-152462 A | | 6/1998 |
| WO | 93/07148 A1 | | 4/1993 |
| WO | 99/35146 A1 | | 7/1999 |
| WO | 02/22577 A2 | | 3/2002 |
| WO | 2002/081435 A1 | | 10/2002 |
| WO | 2004/106328 A1 | | 12/2004 |
| WO | 2005/049594 A1 | | 6/2005 |
| WO | 2006/000420 A1 | | 1/2006 |
| WO | 2006/023778 A2 | | 3/2006 |
| WO | 2006/028958 A2 | | 3/2006 |
| WO | WO2006/071608 | | 7/2006 |
| WO | WO2006/087206 | | 8/2006 |
| WO | 2006/105262 A1 | | 10/2006 |
| WO | 2007/015632 A1 | | 2/2007 |
| WO | WO2007/021839 | | 7/2007 |
| WO | 2008/063525 A1 | | 5/2008 |
| WO | WO2008/127734 | | 10/2008 |
| WO | 2009/040517 A2 | | 4/2009 |
| WO | WO2010/011845 | | 1/2010 |
| WO | 2010/033481 A1 | | 3/2010 |
| WO | WO2010/043721 | | 4/2010 |
| WO | WO2010/084160 | | 7/2010 |
| WO | 2010/138588 A2 | | 12/2010 |
| WO | 2010/143582 A1 | | 12/2010 |
| WO | 2010/147917 A1 | | 12/2010 |
| WO | WO2010/139784 | | 12/2010 |
| WO | WO2011/022489 | | 2/2011 |
| WO | WO2011/035941 | | 3/2011 |
| WO | WO2011/042217 | | 4/2011 |
| WO | 2011/054843 A1 | | 5/2011 |
| WO | 2011/091213 A2 | | 7/2011 |
| WO | WO2011/106105 | | 9/2011 |
| WO | WO2011/106106 | | 9/2011 |
| WO | WO2011/113005 | | 9/2011 |
| WO | 2011/131576 A1 | | 10/2011 |
| WO | 2011/131697 A1 | | 10/2011 |
| WO | 2011/140324 A1 | | 11/2011 |
| WO | 2011/140325 A1 | | 11/2011 |
| WO | 2011/143651 A1 | | 11/2011 |
| WO | WO2012/013727 | | 2/2012 |
| WO | WO2012/013728 | | 2/2012 |
| WO | WO2012/034116 | | 3/2012 |
| WO | 2012/052390 A1 | | 4/2012 |
| WO | WO2012/042042 | | 4/2012 |
| WO | WO2012/045883 | | 4/2012 |
| WO | 2012/075381 A1 | | 6/2012 |
| WO | WO2012/072713 | | 6/2012 |
| WO | 2012/116170 A1 | | 8/2012 |
| WO | WO2012/107498 | | 8/2012 |
| WO | WO2012/107499 | | 8/2012 |
| WO | 2012/118812 A2 | | 9/2012 |
| WO | 2012/129353 A1 | | 9/2012 |
| WO | 2012/135113 A2 | | 10/2012 |
| WO | 2012/142504 A1 | | 10/2012 |
| WO | WO2012/156531 | | 11/2012 |
| WO | WO2012/156537 | | 11/2012 |
| WO | 2013/016081 A1 | | 1/2013 |
| WO | 2013/022047 A1 | | 2/2013 |
| WO | 2013/025805 A1 | | 2/2013 |
| WO | 2013/057322 A1 | | 4/2013 |
| WO | WO2013/057320 | | 4/2013 |
| WO | 2013/120104 A2 | | 8/2013 |
| WO | 2013/178821 A1 | | 12/2013 |
| WO | 2014/058071 A1 | | 4/2014 |
| WO | 2014/084298 A1 | | 6/2014 |
| WO | 2014/085613 A1 | | 6/2014 |
| WO | 2014/086790 A1 | | 6/2014 |
| WO | 2014/134583 A2 | | 9/2014 |
| WO | WO2014/153001 | | 9/2014 |
| WO | 2014/164867 A1 | | 10/2014 |
| WO | 2014/194280 A2 | | 12/2014 |
| WO | 2014/205213 | | 12/2014 |
| WO | 2015/021128 A1 | | 2/2015 |
| WO | 2015/031564 A2 | | 3/2015 |
| WO | 2015/120281 A1 | | 8/2015 |
| WO | 2015/123408 A1 | | 8/2015 |
| WO | 2015/123424 A1 | | 8/2015 |
| WO | 2015/123437 A1 | | 8/2015 |
| WO | 2015/123465 A1 | | 8/2015 |
| WO | 2015/134973 A1 | | 9/2015 |
| WO | 2015/156417 A1 | | 10/2015 |
| WO | 2016/004105 A1 | | 1/2016 |
| WO | 2016/007722 A1 | | 1/2016 |
| WO | 2016/007727 A1 | | 1/2016 |
| WO | 2016/007731 A1 | | 1/2016 |
| WO | 2016/007736 A1 | | 1/2016 |
| WO | 2016/025635 A2 | | 2/2016 |
| WO | 2016/034946 A2 | | 3/2016 |
| WO | 2016/037005 A1 | | 3/2016 |
| WO | 2016/123387 A1 | | 8/2016 |
| WO | 2016/130952 A1 | | 8/2016 |
| WO | 2016/161282 A1 | | 10/2016 |
| WO | 2016/172496 A1 | | 10/2016 |
| WO | 2016/177656 | | 11/2016 |
| WO | WO2016/198649 | | 12/2016 |
| WO | 2017/004519 A1 | | 1/2017 |
| WO | WO2017/013061 | | 1/2017 |
| WO | 2017/027678 A1 | | 2/2017 |

(56) References Cited

FOREIGN PATENT DOCUMENTS

| WO | WO2017/157813 | 9/2017 |
|---|---|---|
| WO | WO2017/157825 | 9/2017 |
| WO | WO2017/158136 | 9/2017 |
| WO | WO2017/212061 | 12/2017 |
| WO | 2015/089192 | 6/2018 |

OTHER PUBLICATIONS

Benelkebir et al, "Enantioselective synthesis of tranylcypromine analogues as lysine demethylase (LSD1) inhibitors", Bioorg Med Chem, 2011,19(12),3709-3716.

Binda et al, "Biochemical, structural, and biological evaluation of tranylcypromine derivatives as inhibitors of histone demethylases LSD1 and LSD2", J Am Chem Soc,2010,132(19),6827-6833.

Choi et al "Histone demethylase LSD1 is required to induce skeletal muscle differentiation by regulating myogenic factors" (2010) Biochemical and Biophysical Research Communications 401(3), 327-332.

Culhane et al, A mechanism-based inactivator for histone demethylase LSD1, J Am Chem Soc, 2006, 128(14), 4536-4537.

Culhane et al, "Comparative analysis of small molecules and histone substrate analogues as LSD1 lysine demethylase inhibitors", J Am Chem Soc, 2010,132(9),3164-3176.

Di Stefano et al, Mutation of Drosophila Lsd1 disrupts H3-K4 methylation, resulting in tissue-specific defects during development, Curr Biol,2007, 17(9), 808-12.

Elsheikh et al "Global histone modifications in breast cancer correlate with tumor phenotypes, prognostic factors and patient outcome", Canc Res, 2009,69, 3802-3809.

Feng et al "Pharmacological inhibition of LSD1 for the treatment of MLL-rearranged leukemia", Journal of Hematology and Oncology, 2016, 9:24.

Fischer et al, "Recovery of learning and memory is associated with chromatin remodelling", Nature, 2007,447, 178-182.

Fiskus et al, "Highly effective combination of LSD1 (KDM1A) antagonist and pan-histone deacetylase inhibitor against human AML cells" Leukemia, 2014, 1-10.

Forneris et al "LSD1: oxidative chemistry for multifaceted functions in chromatin Regulation." Trends in Biochemical Sciences 2008,33(4), 181-189.

Gooden et al, "Facile synthesis of substituted trans-2-arylcyclopropylamine inhibitors of the human histone demethylase LSD1 and monoamine oxidases A and B", Bioorg Med Chem Lett 2008, 18(10), 3047-51.

Hayami et al, "Overexpression of LSD1 contributes to human carcinogenesis through chromatin regulation in various cancers", Int J Cancer, 2011, 128(3), 574-86.

Huang et al, "Novel oligoamine analogues inhibit lysine-specific demethylase 1 (LSD1) and induce re-expression of epigeneticall silenced genes",Clin Cancer Res,2009, 15(23), 7217-28.

Huang et al, "p53 is regulated by the lysine demethylase LSD1",Nature,2007,449, 105-108.

Huang et al,"Inhibition of lysine-specific demethylase 1 by polyamine analogues results in reexpression of aberrantly silenced genes", PNAS,2007, 104(19), 8023-8028.

Huang et al, "Inhibitors of histone demethylation and histone deacetylation cooperate in regulating gene expression and inhibiting growth in human breast cancer cells", Breast Cancer Res Treat, 2012, 131(3):777-789.

Kahl et al,"Androgen receptor coactivators lysine-specific histone demethylase 1 and four and a half LIM domain protein 2 predict risk of prostate cancer recurrence", Cancer Res,2006,66 (23), 11341-11347.

Klaus et al, "DOT1L Inhibitor EPZ-5676 Displays Synergistic Antiproliferative Activity in Combination with Standard of Care Drugs and Hypomethylating Agents in MLL-Rearranged Leukemia Cells", J Pharmacol Exp Ther, 2014, 350(3):646-56.

Lan et al "Mechanisms involved in the regulation of histone lysine demethylases". Current Opinion in Cell Biology, 2008,20, 316-325.

Lee et al, "Histone H3 lysine 4 demethylation is a target of nonselective antidepressive medications",Chem Biol, 2006,13(6), 563-567.

Liang et al, "Inhibition of the histone demethylase LSD1 blocks alpha-herpesvirus lytic replication and reactivation from latency",Nat Med, 2009,15 (11), 1312-1317.

Lim et al, "Lysine-specific demethylase 1 (LSD1) is highly expressed in ER-negative breast cancers and a biomarker predicting aggressive biology", Carcinogenesis,2010, 31(3), 512-20.

McGrath et al, "Pharmacological Inhibition of the Histone Lysine Demethylase KDM1A Suppresses the Growth of Multiple Acute Myeloid Leukemia Subtypes", Cancer Res, 2016, 76:1975-1988.

Metzger et al, "LSD1 demethylates repressive histone marks to promote androgen-receptor-dependent transcription",Nature,2005, 437(7057),436-9.

Mimasu et al "Crystal structure of histone demethylase LSD1 and tranylcypromine at 2.25 Å" Biochemical and Biophysical Research Communications ,2008,366, 15-22.

Mimasu et al, "Structurally designed trans-2-phenylcyclopropylamine derivatives potently inhibit histone demethylase LSD1/KDM1", Biochemistry,2010,49(30), 6494-6503.

Neelamegan et al, "Brain-penetrant LSD1 inhibitors can block memory consolidation", ACS Chem Neurosci, 2012, 3(2), 120-128.

Ogasawara et al, "Synthesis and biological activity of optically active NCL-1, a lysine-specific demethylase 1 selective inhibitor",Bioorg Med Chem, 2011, doi:10.1016/j.bmc.2010.12.024.

Pollock et al, Lysine-specific histone demethylase 1 inhibitors control breast cancer proliferation in ERalpha-dependent and -independent manners, ACS Chem Biol 2012,7,1221-1231.

Prusevich et al, "A Selective Phenelzine Analogue Inhibitor of Histone Demethylase LSD1". ACS Chem Biol, 2014, 9(6):1284-1293.

Ramirez et al, "HDAC and LSD1 Inhibitors Synergize to Induce Cell Death in Acute Leukemia Cells", $53^{rd}$ ASH Annual Meeting and Exposition, 2011, Abstract No. 1427.

Reddy et al, "Role of lysine-specific demethylase 1 in the proinflammatory phenotype of vascular smooth muscle cells of diabetic mice",Circ Res,2008,103, 615-23.

Schmidt et al,"trans-2-phenylcyclopropylamine is a mechanism-based inactivator of the histone demethylase LSD1", Biochemistry, 2007,46(14),4408-4416.

Schulte et al, "Lysine-specific demethylase 1 is strongly expressed in poorly differentiated neuroblastoma: implications for therapy", Cancer Res,2009,69(5),2065-71.

Scoumanne et al "Protein methylation: a new mechanism of p53 tumor suppressor regulation" Histol Histopathol 2008,23, 1143-1149.

Scoumanne et al, "The lysine-specific demethylase 1 is required for cell proliferation in both p53-dependent and -independent manners", J Biol Chem, 2007,282(21), 15471-5.

Seligson et al, "Global histone modification patterns predict risk of prostate cancer recurrence",Nature, 2005,435, 1262-1266.

Seligson et al,"Global levels of histone modifications predict prognosis in different cancers",Am J Path, 2009,174,1619-28.

Sharma et al, "(Bis)urea and (bis)thiourea inhibitors of lysine-specific demethylase 1 as epigenetic modulators", J Med Chem, 2010,53(14), 5197-5212.

Shi, "Histone lysine demethylases: emerging roles in development, physiology and disease", Nature Reviews Genetics 2007, 8:829-833.

Szewczuk et al, "Mechanistic analysis of a suicide inactivator of histone demethylase LSD1", Biochemistry, 2007,46, 6892-6902.

Ueda et al, "Identification of cell-active lysine specific demethylase 1-selective inhibitors",J Am Chem Soc, 2009,131(48), 17536-17537.

Vasilatos et al, "Crosstalk between lysine-specific demethylase 1 (LSD1) and histone deacetylases mediates antineoplastic efficacy of HDAC inhibitors in human breast cancer cells", Carcinogenesis, 2013, 6: 1196-1207.

(56) References Cited

OTHER PUBLICATIONS

Wang et al, "Novel histone demethylase LSD1 inhibitors selectively target cancer cells with pluripotent stem cell properties," Cancer Research, 2011, 71(23):7238-49.
Wang et al "LSD1 Is a Subunit of the NuRD Complex and Targets the Metastasis Programs in Breast Cancer" Cell 2009, 138, 660-672.
Wang et al, "The lysine demethylase LSD1 (KDM1) is required for maintenance of global DNA methylation", Nature Genetics, 2009, 41(1), 125-129.
Yang et al "Structural Basis for the Inhibition of the LSD1 Histone Demethylase by the Antidepressant trans-2-Phenylcyclopropylamine" Biochemistry 2007,46 (27), 8058-8065.
Yang et al "Structural basis of histone demethylation by LSD1 revealed by suicide inactivation" Nature Structural & Molecular Biology 2007, 14(6), 535-539.
Johnson et al, CAPLUS, Document No. 157:576967, "Preparation of cyclopropylamines as LSD1 inhibitors in the treatment of cancer", 2012.
Co-pending U.S. Appl. No. 14/118,330, filed Nov. 18, 2013.
Co-pending U.S. Appl. No. 14/843,095, filed Sep. 2, 2015.
Co-pending U.S. Appl. No. 15/271,772, filed Sep. 21, 2016.
Co-pending U.S. Appl. No. 15/369,003, filed Dec. 5, 2016.
Co-pending U.S. Appl. No. 15/458,636, filed Mar. 14, 2017.
Co-pending U.S. Appl. No. 15/497,556, filed Apr. 26, 2017.
Co-pending U.S. Appl. No. 15/623,866, filed Jun. 15, 2017.
Co-pending U.S. Appl. No. 15/710,912, filed Sep. 21, 2017.
Co-pending U.S. Appl. No. 15/571,945, filed Nov. 6, 2017.
Co-pending U.S. Appl. No. 15/735,377, filed Dec. 11, 2017.
Co-pending U.S. Appl. No. 15/741,871, filed Jan. 4, 2018.
International search report and written opinion for International Application No. PCT/EP2017/055784, dated Jun. 19, 2017.
(Author Not Identified) Handbook of Pharmaceutical Excipients (Cover and Table of Contents only, total in 6 pages), Rowe et al., 5th edition, Grayslake, IL:Pharmaceutical Press, ( 2005).
(Author Not Identified) Remington: The Science and Practice of Pharmacy (Cover and Table of Contents only, total in 4 pages), Gennaro et al., 20th edition, Philadelphia, PA:Lippincott Williams & Wilkins, ( 2000).
Augustyn et al., "ASCL1 is a lineage oncogene providing therapeutic targets for high-grade neuroendocrine lung cancers" Proceedings of the National Academy of Sciences of the USA 111(41):14788-14793 ( 2014).
Cahn et al., "Specification of Molecular Chirality" Angewandte Chemie International Edition in English 5(4):385-415 ( 1966).
Carney et al., "Establishment and Identification of Small Cell Lung Cancer Cell Lines Having Classic and Variant Features" Cancer Research 45:2913-2923 ( 1985).
Cunningham et al., "New Human Assembly—GRCH38" Nucleic Acids Research 43:D662-D669 ( 2015).
Daigle et al., "Selective Killing of Mixed Lineage Leukemia Cells by a Potent Small-Molecule DOT1L Inhibitor" Cancer Cell 20:53-65 ( 2011).
Eliel et al. Stereochemistry of Organic Compounds (Table of Contents (in 11 pages)), New York:John Wiley & Sons, Inc., ( 1994).
Hughes et al., "Matrigel: A complex protein mixture required for optimal growth of cell culture" Proteomics 10:1886-1890 ( 2010).
Li et al., "Lysine-specific demethylase 1 inhibitors protect cochlear spiral ganglion neurons against cisplatin-induced damage" Neuroreport 26(9):539-547 ( 2015).
Mortazavi et al., "Mapping and quantifying mammalian transcriptomes by RNA-Seq" Nature Methods 5(7):621-628 (Jul. 2008).
Reich et al., "GenePattern 2.0" Nature Genetics 38(5):500-501 ( 2006).
Rosenberg et al., "Platinum Compounds: a New Class of Potent Antitumour Agents" Nature 222(5191):385-386 ( 1969).
Selzer et al., "Analysis of Chromosome Breakpoints in Neuroblastoma at Sub-Kilobase Resolution Using Fine-Tiling Oligonucleotide Array CGH" Genes, Chromosomes & Cancer 44:305-319 ( 2005).
Shi et al., "Histone Demethylation Mediated by the Nuclear Amine Oxidase Homolog LSD1" Cell 119:941-953 (Dec. 29, 2004).
Shoemaker, "The NCI60 human tumour cell line anticancer drug screen" Nature Reviews Cancer 6:813-823 ( 2006).
Singh et al., "Inhibition of LSD1 sensitizes glioblastoma cells to histone deacetylase inhibitors" Neuro-Oncology 13(8):894-903 ( 2011).
Singh et al., "Preclinical Activity of Combined HDAC and KDM1A Inhibition in Glioblastoma" Neuro-Oncology 17(11):1463-1473 ( 2015).
Yu et al., "Catalytic site remodelling of the DOT1L methyltransferase by selective inhibitors" Nature Communications 3(1288):1-11 (Dec. 18, 2012).

COMBINATIONS OF LSD1 INHIBITORS FOR USE IN THE TREATMENT OF SOLID TUMORS

CROSS REFERENCE TO RELATED APPLICATION

This application claims the benefit of priority under 35 U.S.C. 119 to U.S. Provisional Patent Application No. 62/308,529, filed Mar. 15, 2016, the content of which is incorporated herein by reference in its entirety.

FIELD OF THE INVENTION

The instant invention relates to therapeutic combinations of LSD1 inhibitors and one or more other active pharmaceutical ingredient(s) or pharmaceutically acceptable salts thereof. The combinations are particularly useful for treating neoplastic diseases, such as cancer, particularly small cell lung cancer (SCLC).

BACKGROUND OF THE INVENTION

Aberrant gene expression in affected tissue as compared to normal tissue is a common characteristic of many human diseases. This is true for cancer and many neurological diseases which are characterized by changes in gene expression patterns. Gene expression patterns are controlled at multiple levels in the cell. Control of gene expression can occur through modifications of DNA: DNA promoter methylation is associated with suppression of gene expression. Several inhibitors of DNA methylation are approved for clinical use including the blockbuster Vidaza™. Another class of modifications involve histones which form the protein scaffold that DNA is normally associated with (coiled around) in eukaryotic cells. Histones play a crucial role in organizing DNA and the regulated coiling and uncoiling of DNA around the histones is critical in controlling gene expression—coiled DNA is typically not accessible for gene transcription. A number of histone modifications have been discovered including histone acetylation, histone lysine methylation, histone arginine methylation, histone ubiquinylation, and histone sumoylation, many of which modify accessibility to the associated DNA by the cells transcriptional machinery. These histone marks serve to recruit various protein complexes involved in transcription and repression. An increasing number of studies are painting an intricate picture of how various combinations of histone marks control gene expression in cell-type specific manner and a new term has been coined to capture this concept: the histone code.

The prototypical histone mark is histone acetylation. Histone acetyl transferase and histone deacetylases are the catalytic machines involved in modulation of this histone mark although typically these enzymes are parts of multi-protein complexes containing other proteins involved in reading and modifying histone marks. The components of these protein complexes are typically cell-type specific and typically comprise transcriptional regulators, repressors, co-repressors, receptors associated with gene expression modulation (e.g., estrogen or androgen receptor). Histone deacetylase inhibitors alter the histone acetylation profile of chromatin. Accordingly, histone deacetylase inhibitors like Vorinostat (SAHA), Trichostatin A (TSA), and many others have been shown to alter gene expression in various in vitro and in vivo animal models. Clinically, histone deacetylase inhibitors have demonstrated activity in the cancer setting and are being investigated for oncology indications as well as for neurological conditions and other diseases.

Another modification that is involved in regulating gene expression is histone methylation including lysine and arginine methylation. The methylation status of histone lysines has recently been shown to be important in dynamically regulating gene expression.

A group of enzymes known as histone lysine methyl transferases and histone lysine demethylases are involved in histone lysine modifications. One particular human histone lysine demethylase enzyme called Lysine Specific Demethylase-1 (LSD1) was recently discovered[1] to be involved in this crucial histone modification. LSD1 has a fair degree of structural similarity, and amino acid identity/homology to polyamine oxidases and monoamine oxidases, all of which (i.e., MAO-A, MAO-B and LSD1) are flavin dependent amine oxidases which catalyze the oxidation of nitrogen-hydrogen bonds and/or nitrogen carbon bonds. LSD1 has been recognized as an interesting target for the development of new drugs to treat cancer, neurological diseases and other conditions.

Cyclopropylamine containing compounds are known to inhibit a number of medically important targets including amine oxidases like Monoamine Oxidase A (MAO-A; or MAOA), Monoamine Oxidase B (MAO-B; or MAOB), and Lysine Specific Demethylase-1 (LSD1). Tranylcypromine (also known as 2-phenylcyclopropylamine), which is the active ingredient of Parnate® and one of the best known examples of a cyclopropylamine, is known to inhibit all of these enzymes. Since MAO-A inhibition may cause undesired side effects, it would be desirable to identify cyclopropylamine derivatives that exhibit potent LSD1 inhibitory activity while being devoid of or having substantially reduced MAO-A inhibitory activity.

Compounds which act as inhibitors of LSD1 are known in the art. LSD1 inhibitors and methods for making them are for example disclosed in WO 2011/131697[2], WO 2012/135113[3], WO 2013/057322[4], WO 2010/143582[5], WO 2011/131576[6], WO 2013/022047[7], WO 2013/025805[8], WO 2014/058071[9], WO 2014/084298[10], WO 2014/085613[11], WO 2014/086790[12], WO2014/164867[13], WO 2014/194280[14], WO 2014/205213[15], WO 2015/021128[16], WO 2015/031564[17], WO 2015/089192[18], WO 2015/120281[19], WO 2015/123465[20], WO 2015/123437[21], WO 2015/123424[22], WO 2015/123408[23], WO 2015/134973[24], WO 2015/156417[25], WO 2015/168466, WO 2015/181380, WO 2015200843, WO 2016003917, WO 2016/004105[26], WO 2016/007722[27], WO 2016/007727[28], WO 2016/007731[29], WO 2016/007736[30], WO 2016/034946[31], WO 2016/037005[32], CN 105541806[33], WO 2016/123387[34], WO 2016/130952[35], CN 105924362[36], CN 105985265[37], WO 2016/161282[38], CN 106045862[39], CN 106045881[40], WO 2016/172496[41], WO 2016/177656[42], WO 2017/004519[43], WO 2017/027678[44] which are incorporated in their entirety herein.

WO 2012/135113[3] discloses compounds, for example GSK2879552 [CAS Reg. No. 1401966-69-5], also known as 4-[[4-[[[(1R,2S)-2-phenylcyclopropyl]amino]methyl]-1-piperidinyl]methyl]-benzoic acid (Example 26 on p. 75, Example 29 on p. 81), as selective LSD1 inhibitor.

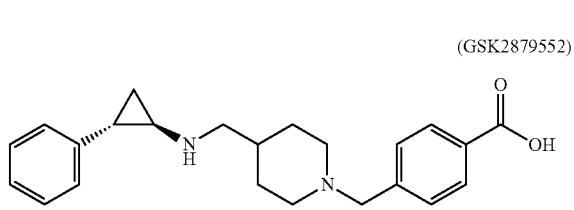 [SMILES: O=C(O)c1ccc(CN2CCC(CN[C@@H]3C[C@H]3c3ccccc3)CC2)cc1]

(GSK2879552)

WO 2017/027678[44] discloses the p-toluenesulfonic acid salt of 1-((4-(methoxymethyl)-4-(((1R,2S)-2-phenylcyclopropylamino)methyl)piperidin-1-yl)methyl)cyclobutanecarboxylic acid

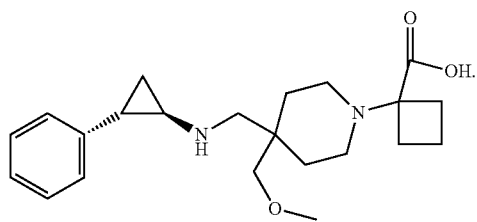

LSD1 inhibitors and methods for making them are for example disclosed in WO 2013/022047[7], particularly examples 1-166 (pages 44 to 114 of corresponding EP2743256), in particular N-[4-[2-[(cyclopropylmethyl-amino)methyl]cyclopropyl]phenyl]-1-methyl-pyrazole-4-carboxamide (Ex. 163) which are incorporated in their entirety herein.

LSD1 inhibitors and methods for making them are for example disclosed in WO 2011/131697[2], particularly examples 1-21 (pages 90 to 103), which are incorporated in their entirety herein.

LSD1 inhibitors and methods for making them are for example disclosed in WO 2013/057322[4], particularly examples 1-108 (pages 155 to 191), which are incorporated in their entirety herein.

Particular LSD1 inhibitors described in WO 2013/057322[4] are provided in Table 1.

TABLE 1

Particular LSD1 inhibitors disclosed in WO 2013/057322[4].

| Example No of WO 2013/057322[4] | Substance name | Structure |
|---|---|---|
| 1 | N1-((trans)-2-phenylcyclopropyl)cyclohexane-1,4-diamine | 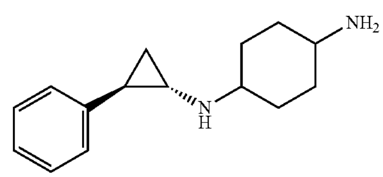 [SMILES: NC1CCC(N[C@H]2C[C@@H]2c2ccccc2)CC1] |
| 5 | (trans)-N1-((1R,2S)-2-phenylcyclopropyl)cyclohexane-1,4-diamine | 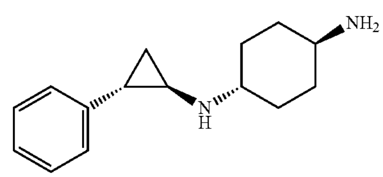 [SMILES: N[C@H]1CC[C@H](N[C@@H]2C[C@H]2c2ccccc2)CC1] |
| 15 | (R)-1-(4-(((trans)-2-phenylcyclopropyl)amino)cyclohexyl)pyrrolidin-3-amine | 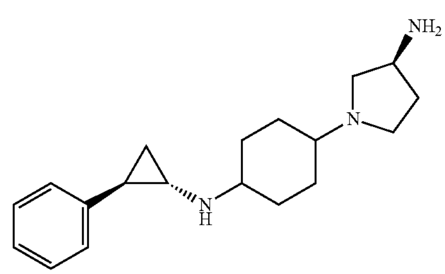 [SMILES: N[C@H]1CCN(C2CCC(N[C@H]3C[C@@H]3c3ccccc3)CC2)C1] |
| 17 | 4-(aminomethyl)-N-((trans)-2-phenylcyclopropyl)cyclohexanamine | 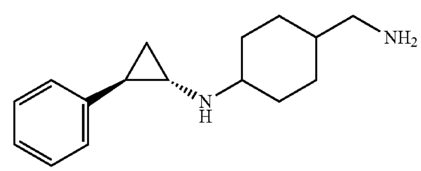 [SMILES: NCC1CCC(N[C@H]2C[C@@H]2c2ccccc2)CC1] |

TABLE 1-continued

Particular LSD1 inhibitors disclosed in WO 2013/057322[4].

| Example No of WO 2013/057322[4] | Substance name | Structure |
|---|---|---|
| 18 | N1-((trans)-2-phenylcyclopropyl)cyclohexane-1,3-diamine | 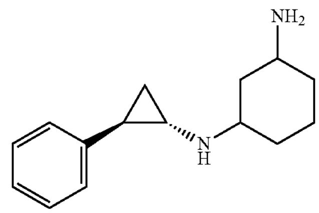 [SMILES: NC1CCCC(N[C@H]2C[C@@H]2c2ccccc2)C1] |
| 19 | N1-((trans)-2-phenylcyclopropyl)cyclobutane-1,3-diamine | 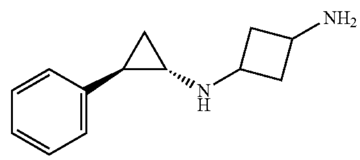 [SMILES: NC1CC(N[C@H]2C[C@@H]2c2ccccc2)C1] |
| 20 | N1-((trans)-2-phenylcyclopropyl)-2,3-dihydro-1H-indene-1,3-diamine | 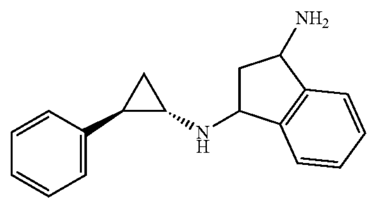 [SMILES: NC1CC(N[C@H]2C[C@@H]2c2ccccc2)c2ccccc21] |
| 22 | N1-methyl-N4-((trans)-2-phenylcyclopropyl)cyclohexane-1,4-diamine | 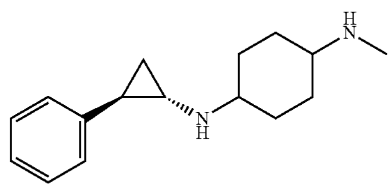 [SMILES: CNC1CCC(N[C@H]2C[C@@H]2c2ccccc2)CC1] |
| 26 | N1-((trans)-2-(4-bromophenyl)cyclopropyl)cyclohexane-1,4-diamine | 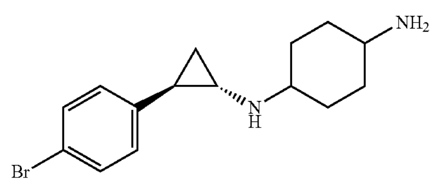 [SMILES: NC1CCC(N[C@H]2C[C@@H]2c2ccc(Br)cc2)CC1] |
| 27 | N1-(2-(o-tolyl)cyclopropyl)cyclohexane-1,4-diamine | 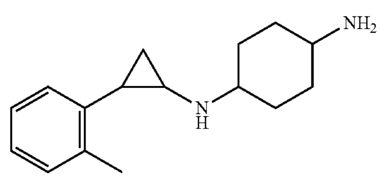 [SMILES: Cc1ccccc1C1CC1NC1CCC(N)CC1] |
| 29 | N1-(2-(4-methoxyphenyl)cyclopropyl)cyclohexane-1,4-diamine | 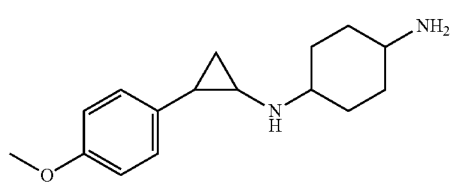 [SMILES: COc1ccc(C2CC2NC2CCC(N)CC2)cc1] |
| 31 | N1-(2-(2-fluorophenyl)cyclopropyl)cyclohexane-1,4-diamine | 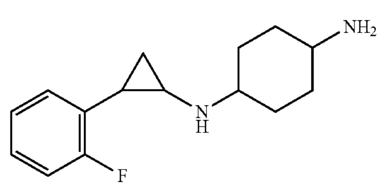 [SMILES: NC1CCC(NC2CC2c2ccccc2F)CC1] |

TABLE 1-continued

Particular LSD1 inhibitors disclosed in WO 2013/057322[4].

| Example No of WO 2013/057322[4] | Substance name | Structure |
|---|---|---|
| 33 | N1-(2-(naphthalen-2-yl)cyclopropyl)cyclohexane-1,4-diamine | 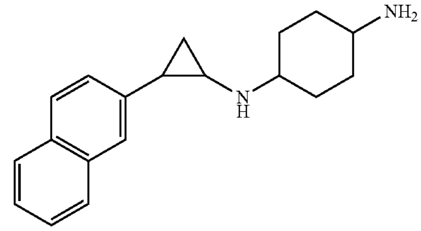 [SMILES: NC1CCC(NC2CC2c2ccc3ccccc3c2)CC1] |
| 50 | N-(4'-((trans)-2-((4-aminocyclohexyl)amino)cyclopropyl)-[1,1'-biphenyl]-3-yl)-2-cyanobenzenesulfonamide | 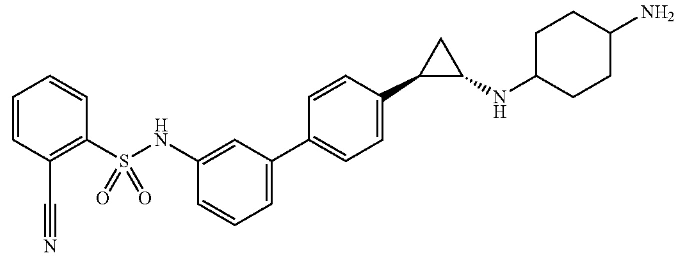 [SMILES: N#Cc1ccccc1S(=O)(=O)Nc1cccc(-c2ccc([C@H]3C[C@@H]3NC3CCC(N)CC3)cc2)c1] |
| 56 | N1-((trans)-2-(4-(pyridin-3-ylmethoxy)phenyl)cyclopropyl)cyclohexane-1,4-diamine | 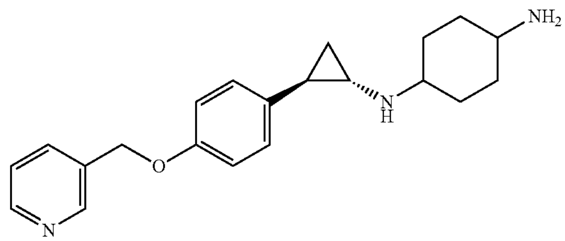 [SMILES: NC1CCC(N[C@H]2C[C@@H]2c2ccc(OCc3cccnc3)cc2)CC1] |

A more particular LSD1 inhibitor described in WO 2013/057322[4] is (trans)-N1-((1R,2S)-2-phenylcyclopropyl)cyclohexane-1,4-diamine [CAS Reg. No. 1431304-21-0]

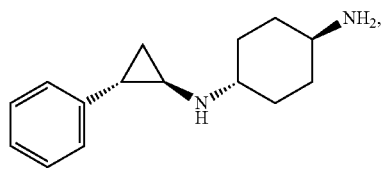 [SMILES: N[C@H]1CC[C@H](N[C@@H]2C[C@H]2c2ccccc2)CC1]

corresponding to Example 5 therein, and pharmaceutically acceptable salts thereof. This compound is also known as ORY-1001.

It has been determined that additive or synergistic effects in inhibiting the growth of cancer cells in vitro and in vivo can be achieved by administering LSD1 inhibitors or pharmaceutically acceptable salts thereof in combination with certain other specific agents. The combination and methods may be useful in the treatment of neoplastic diseases such as cancer.

Accordingly, present invention provides combinations for use in the treatment of neoplastic diseases in a mammal comprising a LSD1 inhibitor or a pharmaceutically acceptable salt thereof, and one or more active pharmaceutical ingredient(s) selected from Table 2 or pharmaceutically acceptable salts thereof.

TABLE 2

Active pharmaceutical ingredients suitable to be combined with LSD1 inhibitors.

| Compound | INN | Mode of Action | Systematic Name | CAS Number | Literature Reference |
|---|---|---|---|---|---|
| ABT-199 | Venetoclax | BCL2 inhibitor | 4-[4-[[2-(4-Chlorophenyl)-4,4-dimethylcyclohex-1-en-1-yl]methyl]piperazin-1-yl]-N-[[3-nitro-4-[[(tetrahydro-2H-pyran-4-yl)methyl]amino]phenyl]sulfonyl]-2-[(1H- | 1257044-40-8 | WO 2010/138588[45] |

TABLE 2-continued

Active pharmaceutical ingredients suitable to be combined with LSD1 inhibitors.

| Compound | INN | Mode of Action | Systematic Name | CAS Number | Literature Reference |
|---|---|---|---|---|---|
| ABT-263 | Navitoclax | BCL2 inhibitor | 4-(4-{[2-(4-Chlorophenyl)-5,5-dimethyl-1-cyclohexen-1-yl]methyl}-1-piperazinyl)-N-[(4-{[(2R)-4-(4-morpholinyl)-1-(phenylsulfanyl)-2-butanyl]amino}-3-[(trifluoromethyl)sulfonyl]phenyl)sulfonyl]benzamide pyrrolo[2,3-b]pyridin-5-yl)oxy]benzamide | 923564-51-6 | US 2007/0027135[46] |
| ABT-737 | | BCL2 inhibitor | 4-[4-[[2-(4-chlorophenyl)phenyl]methyl]piperazin-1-yl]-N-[[(2R)-4-(dimethylamino)-1-phenylsulfanylbutan-2-yl]amino]-3-nitrophenyl]sulfonylbenzamide | 852808-04-9 | WO 2005/049594[47] |
| ABT-888 | Veliparib | PARP inhibitor | 2-((R)-2-Methylpyrrolidin-2-yl)-1H-benzimidazole-4-carboxamide | 912444-00-9 | US 2006/0229289[48] |
| ACY-1215 | Ricolinostat | HDAC inhibitor | 2-(diphenylamino)-N-[7-(hydroxyamino)-7-oxoheptyl]-5-pPyrimidinecarboxamide | 1316214-52-4 | WO 2011/091213[49] |
| Belinostat | Belinostat | HDAC (pan-HDAC) inhibitor | (22E)-N-Hydroxy-3-[3-(phenylsulfamoyl)phenyl]prop-2-enamide | 866323-14-0 | WO 2009/040517[50] |
| Bendamustine | Bendamustine | DNA alkylating agent | 4-[5-[Bis(2-chloroethyl)amino]-1-methylbenzimidazol-2-yl]butanoic acid | 16506-27-7 | DD 159877[51] |
| BGJ398 | Infigratinib | FGFR kinase inhibitor | 3-(2,6-dichloro-3,5-dimethoxyphenyl)-1-(6-((4-(4-ethylpiperazin-1-yl)phenyl)amino)pyrimidin-4-yl)-1-methylurea | 872511-34-7 | WO 2006/000420[52] |
| BMS-906024 | | Notch signaling inhibitor | (2R,3S)-N-[(3S)-1-Methyl-2-oxo-5-phenyl-2,3-dihydro-1H-1,4-benzodiazepin-3-yl]-2,3-bis(3,3,3-trifluoropropyl)succinamide | 1401066-79-2 | WO 2012/129353[53] |
| Carboplatin | Carboplatin | DNA alkylating agent (DNA linker) | cis-diammine(cyclobutane-1,1-dicarboxylate-O,O')platinum(II) | 41575-94-4 | ES 544159[54] |
| CGK 733 | | ATM/ATR kinase inhibitor | α-Phenyl-N-[2,2,2-trichloro-1-[[[(4-fluoro-3-nitrophenyl)amino]thioxomethyl]amino]ethyl]benzeneacetamide | 905973-89-9 | WO 2007/015632[55] |
| Cisplatin | Cisplatin | DNA alkylating agent (DNA linker) | (SP-4-2)-diamminedichloroplatinum(II) | 15663-27-1 | Rosenberg B. et al.[56] |
| CPI-169 | | EZH2 inhibitor (EZH1/2 inhibitor) | N-[(1,2-dihydro-4-methoxy-6-methyl-2-oxo-3-pyridinyl)methyl]-1-[1-1-(ethylsulfonyl)-4-piperidinyl]ethyl]-2-methyl-1H-indole-3-carboxamide | 1450655-76-1 | WO 2013/120104[57] |
| CPI-203 | | BET inhibitor (BRD2/3/ | (6S)-4-(4-chlorophenyl)-2,3,9-trimethyl-6H-thieno[3,2- | 1446144-04-2 | WO 2014/134583[58] |

TABLE 2-continued

Active pharmaceutical ingredients suitable to be combined with LSD1 inhibitors.

| Compound | INN | Mode of Action | Systematic Name | CAS Number | Literature Reference |
|---|---|---|---|---|---|
| | | 4 inhibitor) | f][1,2,4]triazolo[4,3-a][1,4]diazepine-6-acetamide | | |
| Docetaxel | Docetaxel | anti-mitotic agent (TUBB1 stabilizer) | 1,7β,10β-trihydroxy-9-oxo-5β,20-epoxytax-11-ene-2α,4,13α-triyl 4-acetate 2-benzoate 13-{(2R,3S)-3-[(tert-butoxycarbonyl)amino]-2-hydroxy-3-phenylpropanoate} | 114977-28-5 | EP 253738[59] |
| Doxorubicin | Doxorubicin | topoisomerase inhibitor | (7S,9S)-7-[(2R,4S,5S,6S)-4-amino-5-hydroxy-6-methyloxan-2-yl]oxy-6,9,11-trihydroxy-9-(2-hydroxyacetyl)-4-methoxy-8,10-dihydro-7H-tetracene-5,12-dione | 23214-92-8 | DE 2510866[60] |
| EPZ-004777 | | DOT1L inhibitor | 7-[5-Deoxy-5-[[3-[[[[4-(1,1-dimethylethyl)phenyl]amino]carbonyl]amino]propyl](1-methylethyl)amino]-β-D-ribofuranosyl]-7H-pyrrolo[2,3-d]pyrimidin-4-amine | 1338466-77-5 | Daigle S. R. et al.[61] |
| EPZ005687 | | EZH2 inhibitor | 1-cyclopentyl-N-[(1,2-dihydro-4,6-dimethyl-2-oxo-3-pyridinyl)methyl]-6-[4-(4-morpholinylmethyl)phenyl]-1H-indazole-4-carboxamide | 1396772-26-1 | WO 2012/118812[62] |
| EPZ-5676 | Pinometostat | DOT1L inhibitor | 5'-deoxy-5'-[[cis-3-[2-[6-(1,1-dimethylethyl)-1H-benzimidazol-2-yl]ethyl]cyclobutyl](1-methylethyl)amino]-adenosine | 1380288-87-8 | WO 2012/075381[63] |
| EPZ-6438 | Tazemetostat | EZH2 inhibitor | N-[(1,2-dihydro-4,6-dimethyl-2-oxo-3-pyridinyl)methyl]-5-[ethyl(tetrahydro-2H-pyran-4-yl)amino]-4-methyl-4'-(4-morpholinylmethyl)-[1,1'-biphenyl]-3-carboxamide | 1403254-99-8 | WO 2012/142504[64] |
| Erlotinib | Erlotinib | tyrosine kinase inhibitor | N-(3-ethynylphenyl)-6,7-bis(2-methoxyethoxy)quinazolin-4-amine | 183321-74-6 | WO 9630347 A1 |
| Etoposide | Etoposide | topoisomerase inhibitor | 4'-Demethyl-epipodophyllotoxin 9-[4,6-O-(R)-ethylidene-beta-D-glucopyranoside], 4'-(dihydrogen phosphate) | 33419-42-0 | CH 514578[65] |
| FLI 06 | | Notch signaling inhibitor | Cyclohexyl 1,4,5,6,7,8-hexahydro-2,7,7-trimethyl-4-(4-nitrophenyl)-5-oxo-3-quinolinecarboxylate | 313967-18-9 | WO 2013/178821[66] |
| Fluorouracil | Fluorouracil | thymidylate synthase inhibitor | 5-Fluoro-1H,3H-pyrimidine-2,4-dione | 51-21-8 | U.S. Pat No. 2,802,005[67] |
| GDC-0449 | Vismodegib | Hedgehog pathway inhibitor | 2-Chloro-N-(4-chloro-3-pyndin-2-ylphenyl)-4-methylsulfonylbenzamide | 879085-55-9 | WO 2006/028958[68] |
| Gemcitabine | Gemcitabine | nucleoside analog | 4-amino-1-(2-deoxy-2,2-difluoro-β-D-erythro-pentofuranosyl)pyrimidin-2(1H)-on | 95058-81-4 | GB 2136425[69] |

TABLE 2-continued

Active pharmaceutical ingredients suitable to be combined with LSD1 inhibitors.

| Compound | INN | Mode of Action | Systematic Name | CAS Number | Literature Reference |
|---|---|---|---|---|---|
| GSK126 | | EZH2 inhibitor | N-[(1,2-dihydro-4,6-dimethyl-2-oxo-3-pyridinyl)methyl]-3-methyl-1-[(1S)-1-methylpropyl]-6-[6-(1-piperazinyl)-3-pyridinyl]-1H-indole-4-carboxamide | 1346574-57-9 | WO 2011/140324[70] |
| GSK1324726A (I-BET726) | | BET inhibitor (BRD2/3/4 inhibitor) | 4-[(2S,4R)-1-acetyl-4-[(4-chlorophenyl)amino]-1,2,3,4-tetrahydro-2-methyl-6-quinolinyl]-benzoic acid | 1300031-52-0 | WO 2011/054843[71] |
| GSK343 | | EZH2 inhibitor (EZH1/2 inhibitor) | N-[(1,2-dihydro-6-methyl-2-oxo-4-propyl-3-pyridinyl)methyl]-1-(1-methylethyl)-6-[2-(4-methyl-1-piperazinyl)-4-pyridinyl]-1H-indazole-4-carboxamide | 1346704-33-3 | WO 2011/140325[72] |
| GSK-J1 | | demethylase inhibitor (JMJD3/UTX inhibitor) | N-[2-(2-Pyridinyl)-6-(1,2,4,5-tetrahydro-3H-3-benzazepin-3-yl)-4-pyrimidinyl]-β-alanine | 1373422-53-7 | WO 2012/052390[73] |
| GSK1210151A (I-BET151) | | BET inhibitor (BRD2/3/4 inhibitor) | 7,3,5-dimethyl-4-isoxazolyl-1,3-dihydro-8-methoxy-1-[1R-1-(2-pyridinyl)ethyl]-2H-imidazo[4,5-c]quinolin-2-one | 1300031-49-5 | WO 2011/054843[71] |
| Irinotecan | Irinotecan | topoisomerase inhibitor | (S)-4,11-diethyl-3,4,12,14-tetrahydro-4-hydroxy-3,14-dioxo1H-pyrano[3',4':6,7]-indolizino[1,2-b]quinolin-9-yl-[1,4'bipiperidine]-1'-carboxylate | 100286-90-6 | U.S. Pat. No. 6,121,451[74] |
| (+)-JQ1 | | BET inhibitor (BRD2/3/4 inhibitor) | (S)-tert-butyl 2-(4-(4-chlorophenyl)-2,3,9-trimethyl-6H-thieno[3,2-f][1,2,4]triazolo[4,3-a][1,4]diazepin-6-yl)acetate | 1268524-70-4 | WO 2011/143651[75] |
| Lapatinib | Lapatinib | tyrosine kinase inhibitor | N-[3-chloro-4-[(3-fluorophenyl)methoxy]phenyl]-6-[5-[(2-methylsulfonylethylamino)methyl]-2-furyl]quinazolin-4-amine | 231277-92-2 | WO 99/35146[76] |
| LDE225 | Sonidegib | Hedgehog pathway inhibitor | N-[6-[(2S,6R)-2,6-Dimethylmorpholin-4-yl]pyridin-3-yl]-2-methyl-3-[4-(trifluoromethoxy)phenyl]benzamide | 956697-53-3 | WO 2010/033481[77] |
| LY2603618 | | Chk inhibitor | N-[5-bromo-4-methyl-2-[(2S)-2-morpholinylmethoxy]phenyl]-N'-(5-methyl-2-pyrazinyl)-urea | 911222-45-2 | WO 2006/105262[78] |
| LY-3039478 | | Notch signaling inhibitor | N-[(1S)-2-[[(7S)-6,7-dihydro-5-(2-hydroxyethyl)-6-oxo-5H-pyrido[3,2-a][3]benzazepin-7-yl]amino]-1-methyl-2-oxoethyl]-4,4,4-trifluoro-butanamide | 1421438-81-4 | WO 2013/016081[79] |
| Menadione | Menadione | 1,4-naphthoquinone analogue | 2-Methylnaphthalene-1,4-dione | 58-27-5 | U.S. Pat. No. 2,331,725[80] |

TABLE 2-continued

Active pharmaceutical ingredients suitable to be combined with LSD1 inhibitors.

| Compound | INN | Mode of Action | Systematic Name | CAS Number | Literature Reference |
|---|---|---|---|---|---|
| Methotrexate | Methotrexate | folic acid inhibitor (DHFR inhibitor) | (2S)-2-[(4-{[(2,4-Diaminopteridin-6-yl)methyl](methyl)amino}benzoyl)amino]pentanedioic acid | 59-05-2 | U.S. Pat No. 2,512,572 |
| MK-0752 | | Notch signaling inhibitor (gamma secretase inhibitor) | cis-4-[(4-chlorophenyl)sulfonyl]-4-(2,5-difluorophenyl)-cyclohexanepropanoic acid | 471905-41-6 | WO 2002/081435[81] |
| MLN8237 | Alisertib | Aurora A kinase inhibitor | 4-[[9-chloro-7-(2-fluoro-6-methoxyphenyl)-5H-pyrimido[5,4-d][2]benzazepin-2-yl]amino]-2-methoxy-benzoic acid | 1028486-01-2 | WO 2008/063525[82] |
| MS 436 | | BET inhibitor (BRD2/3/4 inhibitor) | 4-[(1E)-2-(2-amino-4-hydroxy-5-methylphenyl)diazenyl]-N-2-pyridinyl-benzenesulfonamide | 1395084-25-9 | WO 2012/116170[83] |
| Nutlin-3A | Nutlin-3A | MDM2 inhibitor | 2-Piperazinone, 4-[[(4S,5R)-4,5-bis(4-chlorophenyl)-4,5-dihydro-2-[4-methoxy-2-(1-methylethoxy)phenyl]-1H-imidazol-1-yl]carbonyl]- | 675576-98-4 | US 2005/0282803[84] |
| Obatoclax | Obatoclax | BCL2 inhibitor | 2-(2-((3,5-Dimethyl-1H-pyrrol-2-yl)methylene)-3-methoxy-2H-pyrrol-5-yl)-1H-indole | 803712-67-6 | WO 2004/106328[85] |
| OTX015 | | BET inhibitor (BRD2/3/4 inhibitor) | (6S)-4-(4-chlorophenyl)-N-(4-hydroxyphenyl)-2,3,9-trimethyl-6H-Thieno[3,2-f][1,2,4]triazolo[4,3-a][1,4]diazepine-6-acetamide | 202590-98-5 | U.S. Pat No. 5,712,274[86] |
| Paclitaxel | Paclitaxel | anti-mitotic agent/TUBB stabilizer | (2α,4α,5β,7β,10β,13α)-4,10-Bis(acetyloxy)-13-{[(2R,3S)-3-(benzoylamino)-2-hydroxy-3-phenylpropanoyl]oxy}-1,7-dihydroxy-9-oxo-5,20-epoxytax-11-en-2-yl benzoate | 33069-62-4 | EP 253739[87] |
| Panobinostat | Panobinostat | HDAC (pan-HDAC) inhibitor | (2E)-N-hydroxy-3-[4-({[2-(2-methyl-1H-indol-3-yl)ethyl]amino}methyl)phenyl]acrylamide | 404950-80-7 | WO 2002/022577[88] |
| Pemetrexed | Pemetrexed | folic acid inhibitor (TYMS/DHFR/GART inhibitor) | (2S)-2-{4-[2-(2-amino-4-oxo-1,7-dihydropyrrolo[2,3-d]pyrimidin-5-yl)ethyl]benzoyl]amino}pentanedioic acid | 137281-23-3 | EP 432677[89] |
| PF-04217903 | | c-Met inhibitor | 4-[1-(6-quinolinylmethyl)-1H-1,2,3-triazolo[4,5-b]pyrazin-6-yl]-1H-pPyrazole-1-ethanol | 956905-27-4 | US 2007/0265272[90] |

TABLE 2-continued

Active pharmaceutical ingredients suitable to be combined with LSD1 inhibitors.

| Compound | INN | Mode of Action | Systematic Name | CAS Number | Literature Reference |
|---|---|---|---|---|---|
| PF-3084014 | | Notch signaling inhibitor (gamma secretase inhibitor) | (2S)-2-[[(2S)-6,8-Difluoro-1,2,3,4-tetrahydro-2-naphthalenyl]amino]-N-[1-[2-[(2,2-dimethylpropyl)amino]-1,1-dimethylethyl]-1H-imidazol-4-yl]pentanamide dihydrobromide | 865773-15-5 | US 2005/0215610[91] |
| SAHA | Vorinostat | HDAC inhibitor | suberanilohydroxamic acid | 149647-78-9 | WO 93/07148[92] |
| SGC 0946 | | DOT1L inhibitor | 1-[3-[[[(2R,3S,4R,5R)-5-(4-Amino-5-bromo-7H-pyrrolo[2,3-d]pyrimidin-7-yl)-3,4-dihydroxytetrahydrofuran-2-yl]methyl](isopropyl)amino]propyl]-3-[4-(2,2-dimethylethyl)phenyl]urea | 1561178-17-3 | Yu et al.[93] |
| SNDX-275 | Entinostat | HDAC inhibitor | N-[[4-[[(2-aminophenyl)amino]carbonyl]phenyl]methyl]-carbamic acid 3-pyridinylmethyl ester | 209783-80-2 | JP 10152462[94] |
| Taladegib | Taladegib | Hedgehog pathway inhibitor (smoothened inhibitor) | 4-fluoro-N-methyl-N-[1-[4-(1-methyl-1H-pyrazol-5-yl)-1-phthalazinyl]-4-piperidinyl]-2-(trifluoromethyl)-benzamide | 1258861-20-9 | WO 2010/147917[95] |
| Temozolomide | Temozolomide | DNA alkylating agent | 4-methyl-5-oxo-2,3,4,6,8-pentazabicyclo[4.3.0]nona-2,7,9-triene-9-carboxamide | 85622-93-1 | DE 3231255[96] |
| Topotecan | Topotecan | topoisomerase inhibitor | (S)-10-[(dimethylamino)methyl]-4-ethyl-4,9-dihydroxy-1H-pyrano[3',4':6,7]indolizino[1,2-b]quinoline-3,14(4H,12H)-dione monohydrochloride | 123948-87-8 | EP 321122[97] |
| TW-37 | | BCL2 inhibitor (BCL2, BCL-xl, MCL-1 inhibitor) | N-[4-[[2-(1,1-dimethylethyl)phenyl]sulfonyl]phenyl]-2,3,4-trihydroxy-5-[[2-(1-methylethyl)phenyl]methyl]-benzamide | 877877-35-5 | WO 2006/023778[98] |
| Vincristine | Vincristine | anti-mitotic agent (TUBB2 destabilizer) | (3aR,3a1R,4R,5S,5aR,10bR)-Methyl 4-acetoxy-3a-ethyl-9-((5S,7S,9S)-5-ethyl-5-hydroxy-9-(methoxycarbonyl)-2,4,5,6,7,8,9,10-octahydro-1H-3,7-methano[1]azacycloundecino[5,4-b]indol-9-yl)-6-formyl-5-hydroxy-8-methoxy-3a,3a1,4,5,5a,6,11,12-octahydro-1H-indolizino[8,1-cd]carbazole-5-carboxylate | 57-22-7 | BE 624076[99] |

The structures of the compounds of Table 2 are as follows:
ABT-199 (Venetoclax):
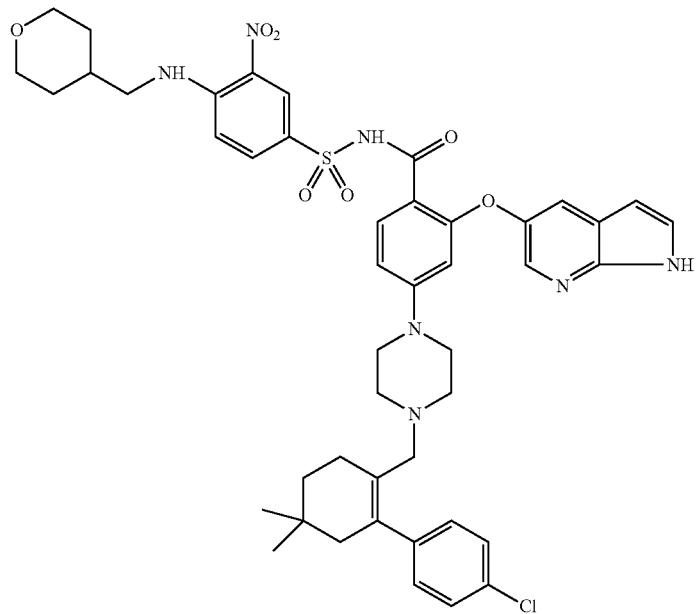
ABT-263 (Navitoclax):
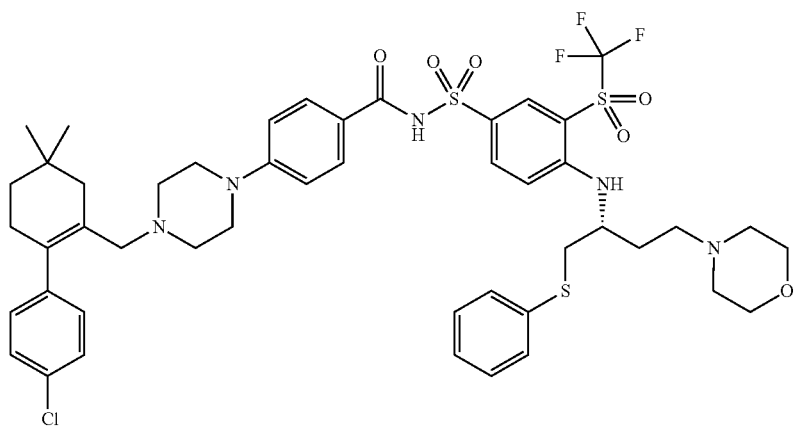
ABT-737:
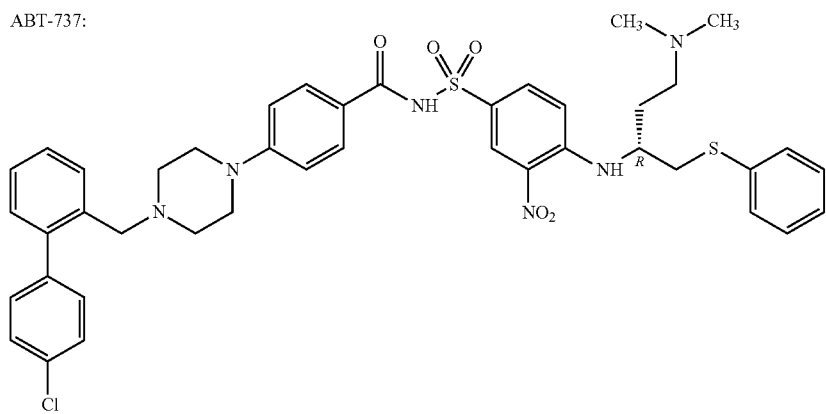

-continued
ABT-888 (Veliparib):
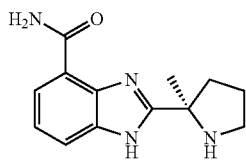
ACY-1215 (Ricolinostat):
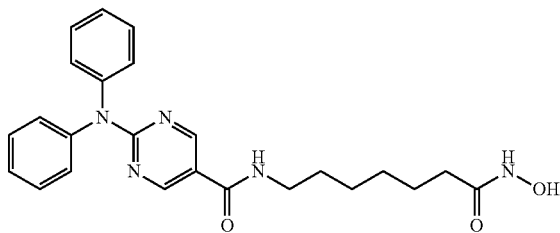
Belinostat:
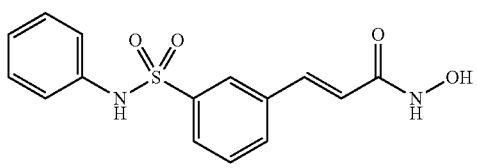
Bendamustine:
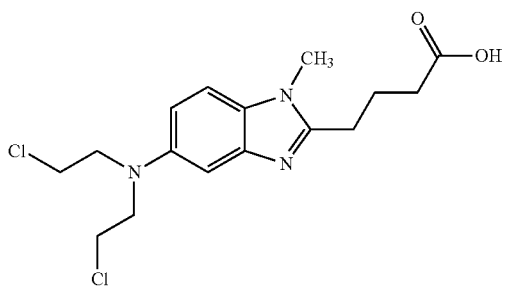
BGJ398 (Infigratinib):
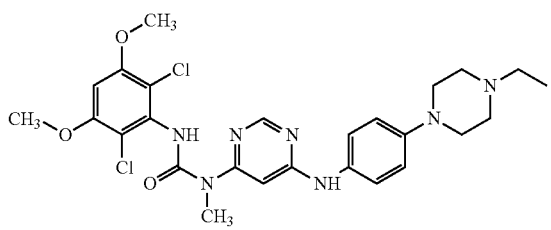
BMS-906024:
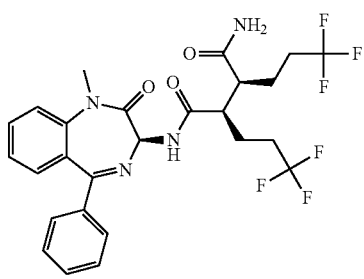
Carboplatin:
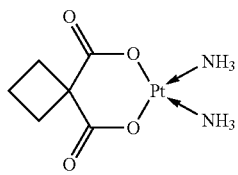
CGK 733:
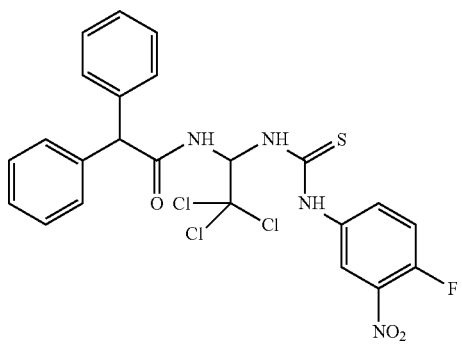
Cisplatin:
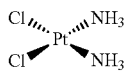
CPI-169:
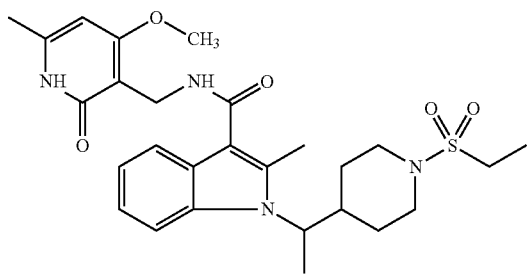

-continued
CPI-203:
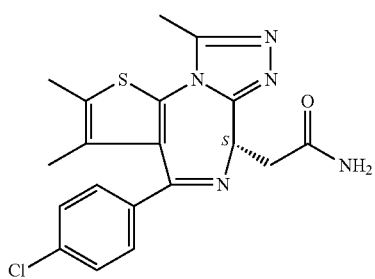
Docetaxel:
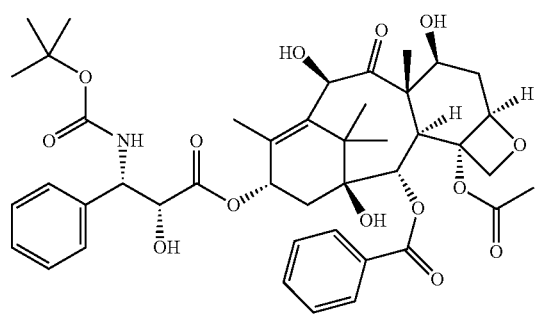
Doxorubicin:
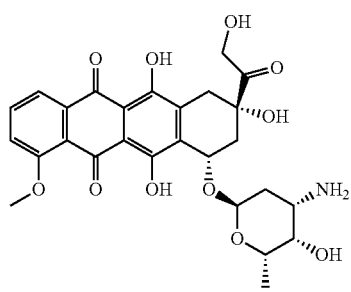
EPZ-004777:
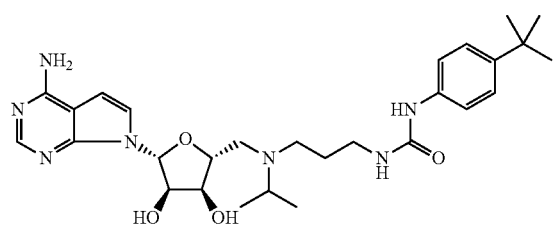
EPZ005687:
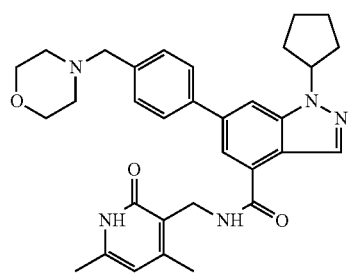
EPZ-5676 (Pinometostat):
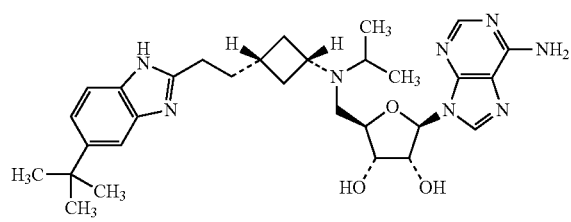
EPZ-6438 (Tazemetostat):
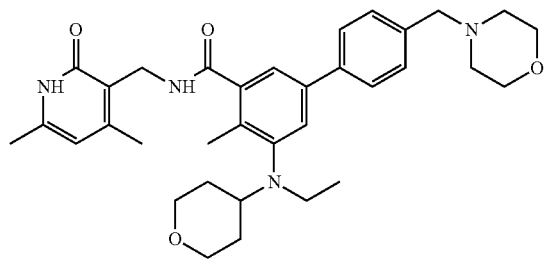
Erlotinib:
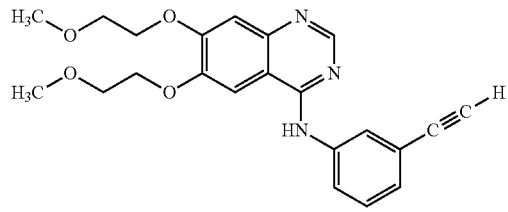

-continued
Etoposide:
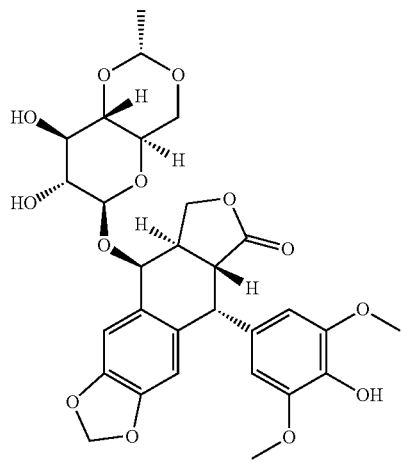
FLI 06:
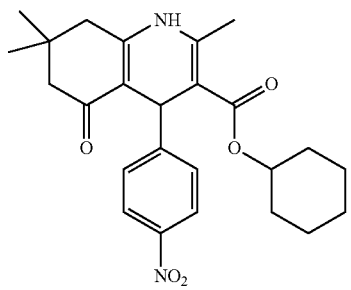
Fluorouracil:
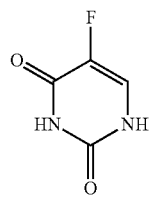
GDC-0449 (Vismodegib):
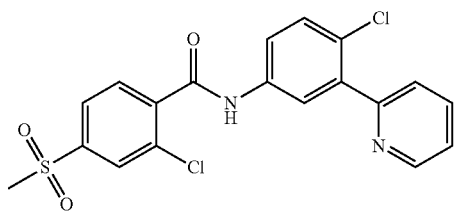
Gemcitabine:
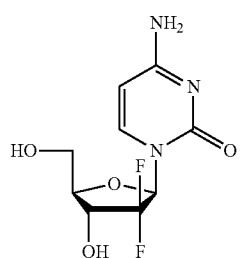
GSK126:
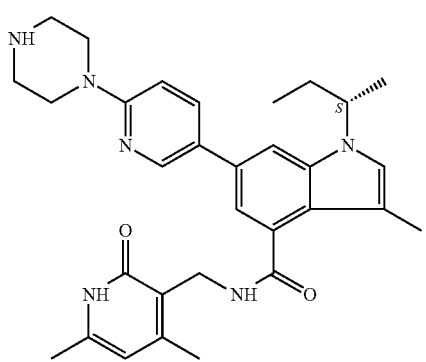
GSK1324726A (I-BET726):
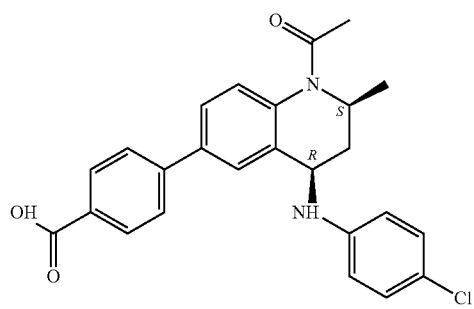
GSK343:
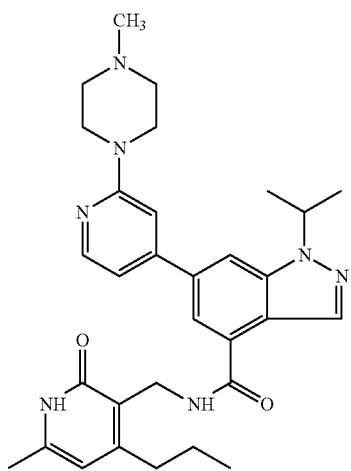

-continued
GSK-J1:
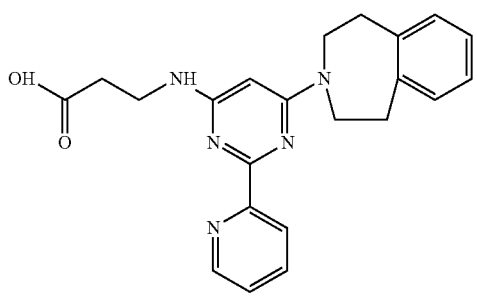
GSK1210151A (I-BET151):
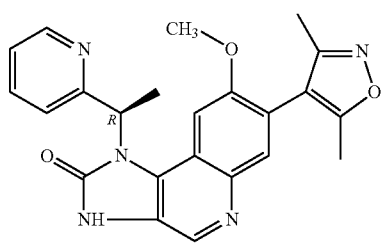
Irinotecan:
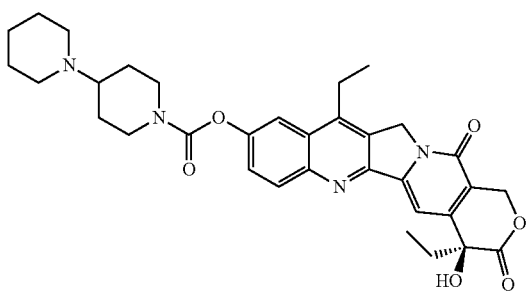
(+)-JQ1:
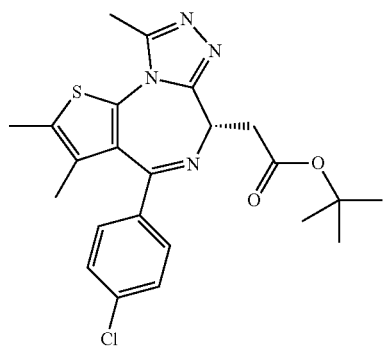
Lapatinib:
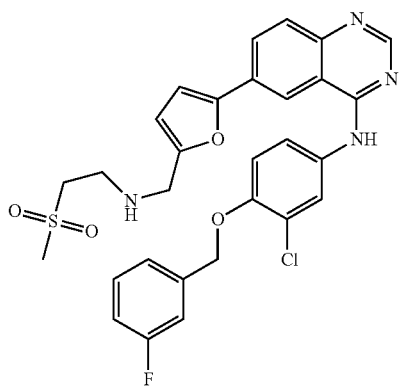
LDE225 (Sonidegib):
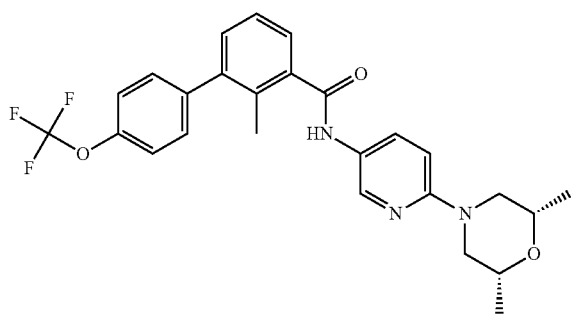
LY2603618:
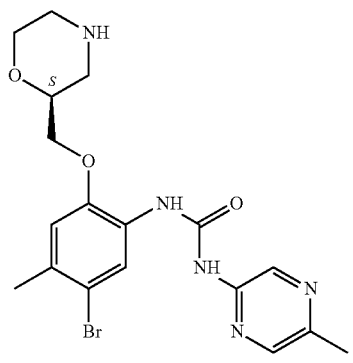
LY-3039478:
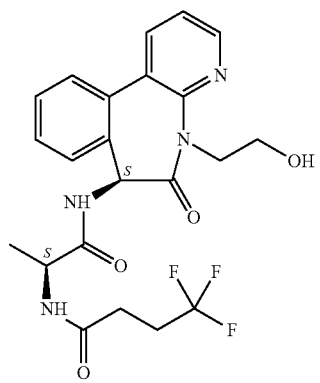

-continued
Menadione:
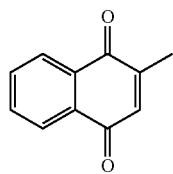
Methotrexate:
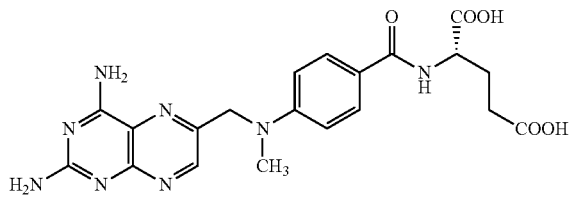
MK-0752:
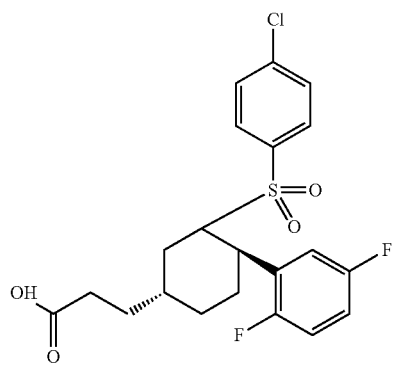
MLN8237 (Alisertib):
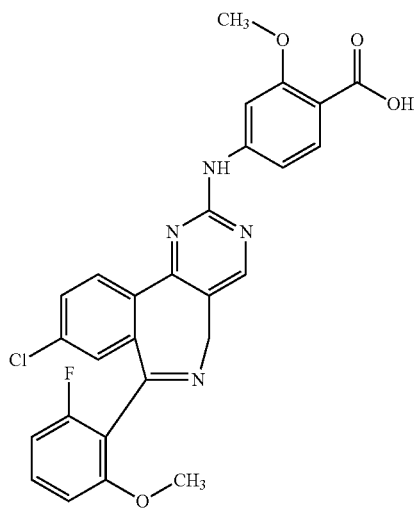
MS 436:
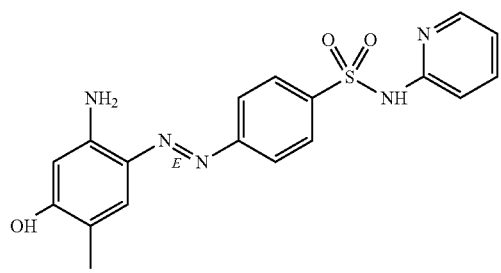
Nutlin-3A:
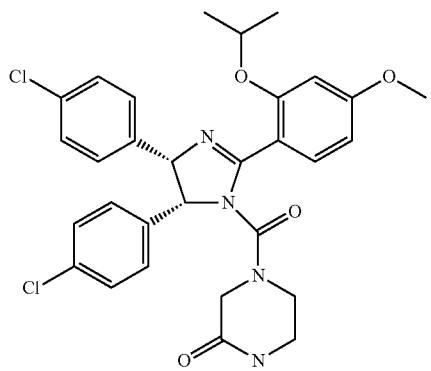
Obatoclax:
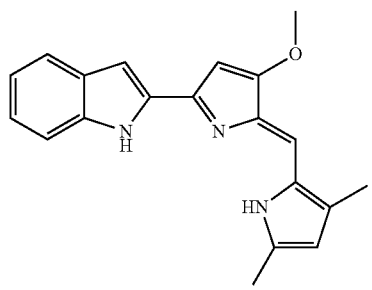
OTX015:
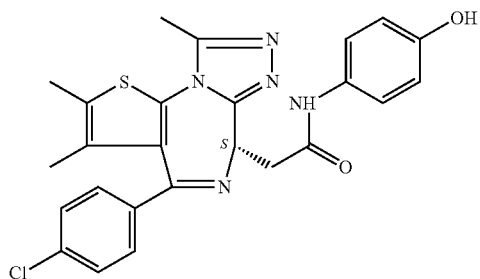

-continued
Paclitaxel:
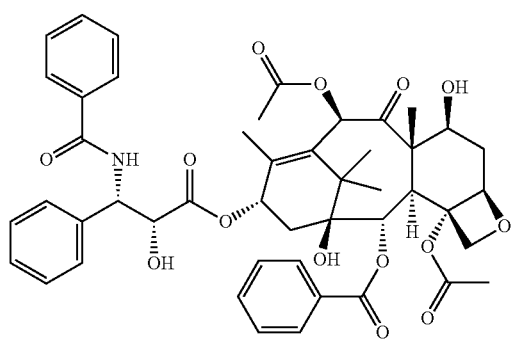
Panobinostat:
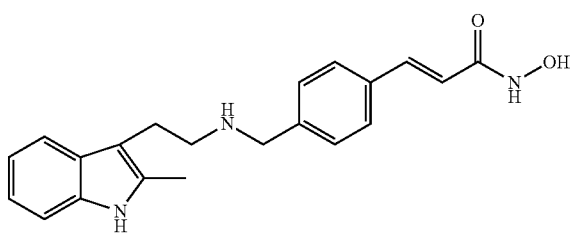
Pemetrexed:
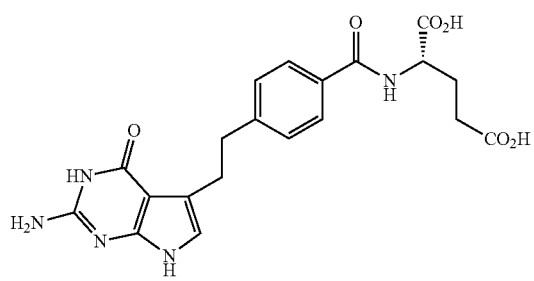
PF-04217903:
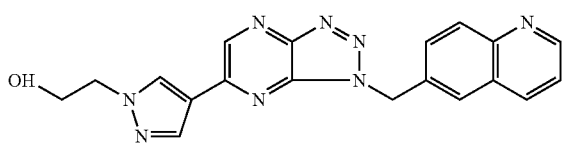
PF-3084014:
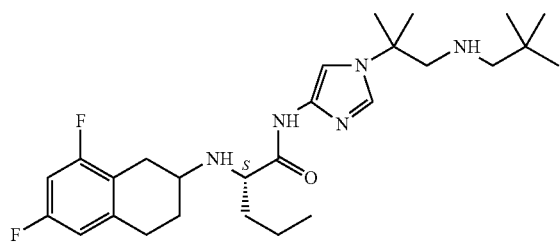
SAHA (Vorinostat):
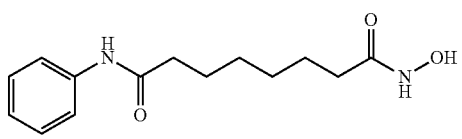
SGC 0946:
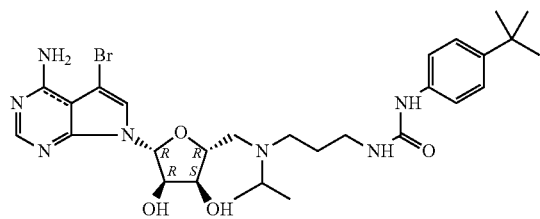
SNDX-275 (Entinostat):
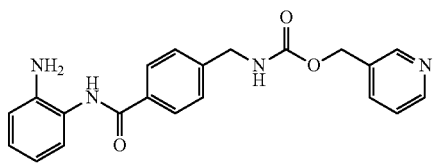

Taladegib:

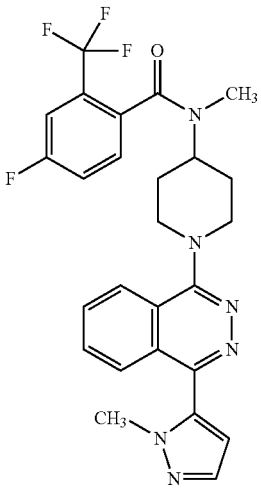

Topotecan:

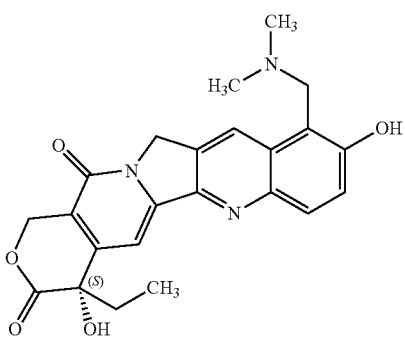

Vincristine:

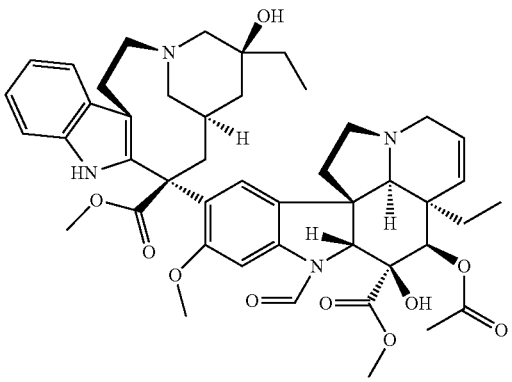

Temozolomide:

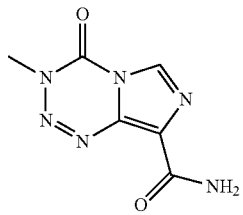

TW-37:

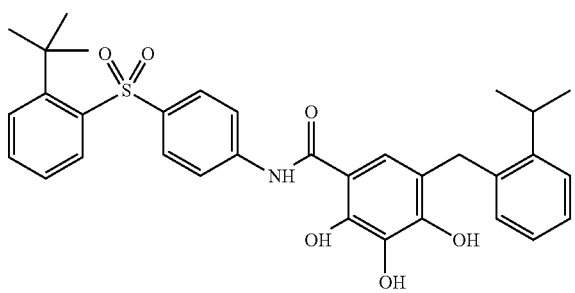

DETAILED DESCRIPTION OF THE INVENTION

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below.

All publications, patent applications, patents, and other references mentioned herein are incorporated by reference in their entirety.

The nomenclature used in this Application is based on IUPAC systematic nomenclature, unless indicated otherwise.

Any open valency appearing on a carbon, oxygen, sulfur or nitrogen atom in the structures herein indicates the presence of hydrogen, unless indicated otherwise.

When indicating the number of substituents, the term "one or more" refers to the range from one substituent to the highest possible number of substitution, i.e. replacement of one hydrogen up to replacement of all hydrogens by substituents.

The term "optional" or "optionally" denotes that a subsequently described event or circumstance can but need not occur, and that the description includes instances where the event or circumstance occurs and instances in which it does not.

"The term "pharmaceutically acceptable salts" denotes salts which are not biologically or otherwise undesirable. Pharmaceutically acceptable salts include both acid and base addition salts.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, and salicyclic acid.

The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, and polyamine resins.

Stereochemical definitions and conventions used herein generally follow S. P. Parker[100]; and Eliel, E. and Wilen, S.[101]. In describing an optically active compound, the prefixes D and L, or R and S, are used to denote the absolute configuration of the molecule about its chiral center(s). The substituents attached to the chiral center under consideration are ranked in accordance with the Sequence Rule of Cahn, Ingold and Prelog[102]. The prefixes D and L or (+) and (-) are employed to designate the sign of rotation of plane-polarized light by the compound, with (-) or L designating that the compound is levorotatory. A compound prefixed with (+) or D is dextrorotatory.

The terms "pharmaceutical composition" and "pharmaceutical formulation" (or "formulation") are used interchangeably and denote a mixture or solution comprising a therapeutically effective amount of an active pharmaceutical ingredient together with pharmaceutically acceptable excipients to be administered to a mammal, e.g., a human in need thereof.

The term "pharmaceutically acceptable" denotes an attribute of a material which is useful in preparing a pharmaceutical composition that is generally safe, non-toxic, and neither biologically nor otherwise undesirable and is acceptable for veterinary as well as human pharmaceutical use.

The terms "pharmaceutically acceptable excipient", "pharmaceutically acceptable carrier" and "therapeutically inert excipient" can be used interchangeably and denote any pharmaceutically acceptable ingredient in a pharmaceutical composition having no therapeutic activity and being non-toxic to the subject administered, such as disintegrators, binders, fillers, solvents, buffers, tonicity agents, stabilizers, antioxidants, surfactants, carriers, diluents or lubricants used in formulating pharmaceutical products.

The term "inhibitor" denotes a compound which competes with, reduces or prevents the binding of a particular ligand to a particular receptor or enzyme and/or which reduces or prevents the activity of a particular protein, e.g. of a receptor or an enzyme.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

The term "animal" as used herein comprises human beings and non-human animals. In one embodiment, a "non-human animal" is a mammal, for example a rodent such as rat or a mouse. In one embodiment, a non-human animal is a mouse.

The term "half maximal effective concentration" (EC50) denotes the plasma concentration of a particular compound or molecule required for obtaining 50% of the maximum of a particular effect in vivo.

The term "therapeutically effective amount" (or "effective amount") denotes an amount of a compound or molecule of the present invention that, when administered to a subject, (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. The therapeutically effective amount will vary depending on the compound, the disease state being treated, the severity of the disease treated, the age and relative health of the subject, the route and form of administration, the judgment of the attending medical or veterinary practitioner, and other factors.

The term "treating" or "treatment" of a disease state includes inhibiting the disease state, i.e., arresting the development of the disease state or its clinical symptoms, or relieving the disease state, i.e., causing temporary or permanent regression of the disease state or its clinical symptoms.

The term "assessing a neoplastic disease" is used to indicate that the method according to the present invention will aid a medical professional including, e.g., a physician in assessing whether an individual has a neoplastic disease or is at risk of developing a neoplastic disease. The levels of a gene panel as compared to one or more reference levels indicate whether the individual has a neoplastic disease or whether the individual is at risk of developing a neoplastic disease or prognosing the course of a neoplastic disease. In one embodiment the term assessing a neoplastic disease is used to indicate that the method according to the present invention will aid the medical professional in assessing whether an individual has a neoplastic disease or not. In these embodiment levels of a gene panel as compared to one or more reference levels indicate whether the individual has a neoplastic disease.

The term "assessing a therapy" is used to indicate that the method according to the present invention will aid a medical professional including, e.g., a physician in assessing whether an individual having a neoplastic disease should be treated with an effective amount of an LSD1 inhibitor. Levels of the responder genes above the reference level, and/or levels of the non-responder genes below the reference level indicate that the patient should be treated with an effective amount of an LSD1 inhibitor. In certain embodiments, the term "at the reference level" refers to a level of a gene of the gene panel in the sample from the individual or patient that is essentially identical to the reference level or to a level that differs from the reference level by up to 1%, up to 2%, up to 3%, up to 4%, up to 5%.

In certain embodiments, the term "above the reference level" refers to a level of a gene of the gene panel in the sample from the individual or patient above the reference level or to an overall increase of 5%, 10%, 20%, 25%, 30%, 40%, 50%, 60%, 70%, 80%, 85%, 90%, 95%, 100% or greater, determined by the methods described herein, as compared to the reference level. In certain embodiments, the term increase refers to the increase in a level of a gene of the gene panel in the sample from the individual or patient wherein, the increase is at least about 1.5-, 1.75-, 2-, 3-, 4-, 5-, 6-, 7-, 8-, 9-, 10-, 15-, 20-, 25-, 30-, 40-, 50-, 60-, 70-, 75-, 80-, 90-, or 100-fold higher as compared to the reference level, e.g. predetermined from a reference sample.

In certain embodiments, the term "decrease" or "below" herein to a level of a gene of the gene panel in the sample from the individual or patient below the reference level or to an overall reduction of 5%, 10%, 20%, 25%, 30%, 40%, 50%, 60%, 70%, 80%, 85%, 90%, 95%, 96%, 97%, 98%, 99% or greater, determined by the methods described herein, as compared to the reference level. In certain embodiments, the term decrease refers to a decrease in a level of a gene of the gene panel in the sample from the individual or patient wherein the decreased level is at most about 0.9-, 0.8-, 0.7-, 0.6-, 0.5-, 0.4-, 0.3-, 0.2-, 0.1-, 0.05-, or 0.01-fold of the reference level, e.g. predetermined from a reference sample, or lower.

The term "biomarker" as used herein refers generally to a gene, the expression or presence of which in or on a mammalian tissue or cell can be detected by standard methods (or methods disclosed herein) and which may be predictive, diagnostic and/or prognostic for a mammalian cell's or tissue's sensitivity to treatment regimens based on LSD1 inhibition by e.g. an LSD1 inhibitor such as (trans)-N1-((1R,2S)-2-phenylcyclopropyl)cyclohexane-1,4-diamine bis-hydrochloride. In certain embodiments, the level of such a biomarker is determined to be higher or lower than that observed for a reference sample.

The term "comparing" as used herein refers to comparing the level of the biomarker in the sample from the individual or patient with the reference level of the biomarker specified elsewhere in this description. It is to be understood that comparing as used herein usually refers to a comparison of corresponding parameters or values, e.g., an absolute amount is compared to an absolute reference amount while a concentration is compared to a reference concentration or an intensity signal obtained from the biomarker in a sample is compared to the same type of intensity signal obtained from a reference sample. The comparison may be carried out manually or computer assisted. Thus, the comparison may be carried out by a computing device (e.g., of a system disclosed herein). The value of the measured or detected level of the biomarker in the sample from the individual or patient and the reference level can be, e.g., compared to each other and the said comparison can be automatically carried out by a computer program executing an algorithm for the comparison. The computer program carrying out the said evaluation will provide the desired assessment in a suitable output format. For a computer assisted comparison, the value of the determined amount may be compared to values corresponding to suitable references which are stored in a database by a computer program. The computer program may further evaluate the result of the comparison, i.e. automatically provide the desired assessment in a suitable output format. For a computer assisted comparison, the value of the determined amount may be compared to values corresponding to suitable references which are stored in a database by a computer program. The computer program may further evaluate the result of the comparison, i.e. automatically provides the desired assessment in a suitable output format.

The term "detecting" a biomarker as used herein refers to methods of detecting the presence of quantity of the biomarker in the sample employing appropriate methods of detection described elsewhere herein.

The term "measuring" the level of a biomarker, as used herein refers to the quantification of the biomarker, e.g. to determining the level of the biomarker in the sample, employing appropriate methods of detection described elsewhere herein.

The term "monitoring the efficacy of a therapy" is used to indicate that a sample is obtained at least once, including serially, from a patient before and/or under therapy with an LSD1 inhibitor and that gene panel levels are measured therein to obtain an indication whether the therapy is efficient or not.

In the monitoring of the efficacy of a therapy the gene panel levels are measured and in one embodiment compared to a reference value for the gene panel, or, in a further embodiment, it is compared to the gene panel levels in a sample obtained from the same patient at an earlier point in time, e.g. while said patient was already under therapy or before start of a therapy in said patient.

A "patient" or "subject" herein is any single human subject eligible for treatment who is experiencing or has experienced one or more signs, symptoms, or other indicators of a neoplastic disease. Intended to be included as a subject are any subjects involved in clinical research trials not showing any clinical sign of disease, or subjects involved in epidemiological studies, or subjects once used as controls. The subject may have been previously treated with an LSD1 inhibitor or another drug, or not so treated. The subject may be naïve to an additional drug(s) being used when the treatment herein is started, i.e., the subject may not have been previously treated with, for example, a therapy other than an LSD1 inhibitor at "baseline" (i.e., at a set point in time before the administration of a first dose of Drug D in the treatment method herein, such as the day of screening the subject before treatment is commenced). Such "naïve" subjects are generally considered to be candidates for treatment with such additional drug(s).

The phrase "providing a diagnosis/assessment" as used herein refers to using the information or data generated relating to the gene panel levels in a sample of a patient to diagnose/assess a neoplastic disease in the patient. The information or data may be in any form, written, oral or electronic. In some embodiments, using the information or data generated includes communicating, presenting, reporting, storing, sending, transferring, supplying, transmitting, dispensing, or combinations thereof. In some embodiments, communicating, presenting, reporting, storing, sending, transferring, supplying, transmitting, dispensing, or combinations thereof are performed by a computing device, analyzer unit or combination thereof. In some further embodiments, communicating, presenting, reporting, storing, sending, transferring, supplying, transmitting, dispensing, or combinations thereof are performed by a laboratory or medical professional. In some embodiments, the information or data includes a comparison of the gene panel levels to a reference level.

The phrase "recommending a treatment" as used herein refers to using the information or data generated relating to the gene panel levels in a sample of a patient to identify the patient as suitably treated or not suitably treated with a therapy. In some embodiment the therapy may comprise an LSD1 inhibitor. In some embodiments the phrase "recommending a treatment/therapy" includes the identification of a patient who requires adaptation of an effective amount of an LSD1 inhibitor being administered. In some embodiments recommending a treatment includes recommending that the amount of an LSD1 inhibitor being administered is adapted. The phrase "recommending a treatment" as used herein also may refer to using the information or data generated for proposing or selecting a therapy comprising an LSD1 inhibitor for a patient identified or selected as more or less likely to respond to the therapy comprising a LSD1 inhibitor. The information or data used or generated may be in any form, written, oral or electronic. In some embodiments, using the information or data generated includes communicating, presenting, reporting, storing, sending, transferring, supplying, transmitting, dispensing, or combinations thereof. In some embodiments, communicating, presenting, reporting, storing, sending, transferring, supplying, transmitting, dispensing, or combinations thereof are performed by a computing device, analyzer unit or combination thereof. In some further embodiments, communicating, presenting, reporting, storing, sending, transferring, supplying, transmitting, dispensing, or combinations thereof are performed by a laboratory or medical professional. In some embodiments, the information or data includes a comparison of the gene panel levels to a reference level. In some embodiments, the information or data includes an indication that the patient is suitably treated or not suitably treated with a therapy comprising an LSD1 inhibitor.

In certain embodiments, the term "reference level" herein refers to a predetermined value. In this context "level" encompasses the absolute amount, the relative amount or concentration as well as any value or parameter which correlates thereto or can be derived therefrom. As the skilled artisan will appreciate the reference level is predetermined and set to meet routine requirements in terms of e.g. specificity and/or sensitivity. These requirements can vary, e.g. from regulatory body to regulatory body. It may for example be that assay sensitivity or specificity, respectively, has to be set to certain limits, e.g. 80%, 90%, 95% or 98%, respectively. These requirements may also be defined in terms of positive or negative predictive values. Nonetheless, based on the teaching given in the present invention it will always be possible for a skilled artisan to arrive at the reference level meeting those requirements. In one embodiment the reference level is determined in reference samples from healthy individuals. The reference level in one embodiment has been predetermined in reference samples from the disease entity to which the patient belongs. In certain embodiments the reference level can e.g. be set to any percentage between 25% and 75% of the overall distribution of the values in a disease entity investigated. In other embodiments the reference level can e.g. be set to the median, tertiles or quartiles as determined from the overall distribution of the values in reference samples from a disease entity investigated. In one embodiment the reference level is set to the median value as determined from the overall distribution of the values in a disease entity investigated. The reference level may vary depending on various physiological parameters such as age, gender or subpopulation, as well as on the means used for the determination of the gene panel levels referred to herein. In one embodiment, the reference sample is from essentially the same type of cells, tissue, organ or body fluid source as the sample from the individual or patient subjected to the method of the invention, e.g. if according to the invention blood is used as a sample to determine the gene panel levels in the individual, the reference level is also determined in blood or a part thereof.

The phrase "responsive to" in the context of the present invention indicates that a patient suffering from, being suspected to suffer or being prone to suffer from, or diagnosed with a disorder as described herein, shows a response to therapy comprising an LSD1 inhibitor.

The term "sample" refers to a sample of a body fluid, to a sample of separated cells or to a sample from a tissue or an organ. Samples of body fluids can be obtained by well-known techniques and include, samples of blood, plasma, serum, urine, lymphatic fluid, sputum, ascites, bronchial lavage or any other bodily secretion or derivative thereof. Tissue or organ samples may be obtained from any tissue or organ by, e.g., biopsy. Separated cells may be obtained from the body fluids or the tissues or organs by separating techniques such as centrifugation or cell sorting. E.g., cell-, tissue- or organ samples may be obtained from those cells, tissues or organs which express or produce the biomarker. The sample may be frozen, fresh, fixed (e.g. formalin fixed), centrifuged, and/or embedded (e.g. paraffin embedded), etc. The cell sample can, of course, be subjected to a variety of well-known post-collection preparative and storage techniques (e.g., nucleic acid and/or protein extraction, fixation, storage, freezing, ultrafiltration, concentration, evaporation, centrifugation, etc.) prior to assessing the amount of the marker in the sample. Likewise, biopsies may also be subjected to post-collection preparative and storage techniques, e.g., fixation.

The phrase "selecting a patient" or "identifying a patient" as used herein refers to using the information or data generated relating to the gene panel levels in a sample of a patient to identify or selecting the patient as more likely to benefit or less likely to benefit from a therapy comprising an LSD1 inhibitor. The information or data used or generated may be in any form, written, oral or electronic. In some embodiments, using the information or data generated includes communicating, presenting, reporting, storing, sending, transferring, supplying, transmitting, dispensing, or combinations thereof. In some embodiments, communicating, presenting, reporting, storing, sending, transferring, supplying, transmitting, dispensing, or combinations thereof are performed by a computing device, analyzer unit or combination thereof. In some further embodiments, communicating, presenting, reporting, storing, sending, transferring, supplying, transmitting, dispensing, or combinations thereof are performed by a laboratory or medical professional. In some embodiments, the information or data includes a comparison of the gene panel levels to a reference level. In some embodiments, the information or data includes an indication that the patient is more likely or less likely to respond to a therapy comprising an LSD1 inhibitor.

The phrase "selecting a therapy" as used herein refers to using the information or data generated relating to the gene panel levels in a sample of a patient to identify or selecting a therapy for a patient. In some embodiment the therapy may comprise an LSD1 inhibitor. In some embodiments the phrase "identifying/selecting a therapy" includes the identification of a patient who requires adaptation of an effective amount of an LSD1 inhibitor being administered. In some embodiments recommending a treatment includes recommending that the amount of LSD1 inhibitor being administered is adapted. The phrase "recommending a treatment" as used herein also may refer to using the information or data generated for proposing or selecting a therapy comprising an LSD1 inhibitor for a patient identified or selected as more or less likely to respond to the therapy comprising an LSD1 inhibitor. The information or data used or generated may be in any form, written, oral or electronic. In some embodiments, using the information or data generated includes communicating, presenting, reporting, storing, sending, transferring, supplying, transmitting, dispensing, or combinations thereof. In some embodiments, communicating, presenting, reporting, storing, sending, transferring, supplying, transmitting, dispensing, or combinations thereof are performed by a computing device, analyzer unit or combination thereof. In some further embodiments, communicating, presenting, reporting, storing, sending, transferring, supplying, transmitting, dispensing, or combinations thereof are performed by a laboratory or medical professional. In some embodiments, the information or data includes a comparison of the gene panel levels to a reference level. In some embodiments, the information or data includes an indication that a therapy comprising an LSD1 inhibitor is suitable for the patient.

The term "responder gene" refers to the group of genes comprising ASCL1, HOXA10, NCAM1, NCAM2, NEUROD1, DDC, GRP, KRT8, ENO2, AVP, OXT, SYP, CHGA, CHGB, SOX21 and BCL2.

The term "non-responder gene" refers to the oncogene MYC.

The term "solid tumor" relates to an abnormal mass of tissue that usually does not contain cysts or liquid areas. Solid tumors may be benign (not cancer), or malignant (cancer). Different types of solid tumors are named for the type of cells that form them. Examples of solid tumors are sarcomas, carcinomas, and lymphomas. Leukemias (cancers of the blood) generally do not form solid tumors.

Therapeutic Combinations

In detail, the present invention provides a therapeutic combination comprising an LSD1 inhibitor or a pharmaceutically acceptable salt thereof, and one or more active pharmaceutical ingredients selected from a compound of Table 2 and pharmaceutically acceptable salts thereof.

In detail, the present invention provides a therapeutic combination comprising an LSD1 inhibitor or a pharmaceutically acceptable salt thereof, and one or more active pharmaceutical ingredients selected from the list of ABT-199, ABT-263, ABT-737, ABT-888, ACY-1215, Belinostat, Bendamustine, BGJ398, BMS-906024, Carboplatin, CGK 733, Cisplatin, CPI-169, CPI-203, Docetaxel, Doxorubicin, EPZ-004777, EPZ005687, EPZ-5676, EPZ-6438, Erlotinib, Etoposide, FLI 06, Fluorouracil, GDC-0449, Gemcitabine, GSK126, GSK1324726A, GSK343, GSK-J1, GSK1210151A, Irinotecan, (+)-JQ1, Lapatinib, LDE225, LY2603618, LY-3039478, Menadione, Methotrexate, MK-0752, MLN8237, MS 436, Nutlin-3A, Obatoclax, OTX015, Paclitaxel, Panobinostat, Pemetrexed, PF-04217903, PF-3084014, SAHA, SGC 0946, SNDX-275, Taladegib, Temozolomide, Topotecan, TW-37, Vincristine and pharmaceutically acceptable salts thereof.

In detail, the present invention provides a therapeutic combination comprising an LSD1 inhibitor or a pharmaceutically acceptable salt thereof, and one or more active pharmaceutical ingredients selected from BCL2 inhibitors, BET inhibitors, EZH2 inhibitors, DOT1L inhibitors, Chk inhibitors, DNA alkylating agents, HDAC inhibitors, topoisomerase inhibitors, anti-mitotic agents, Aurora kinase inhibitors and pharmaceutically acceptable salts thereof.

In detail, the present invention provides a therapeutic combination comprising an LSD1 inhibitor or a pharmaceutically acceptable salt thereof, and one or more active pharmaceutical ingredients selected from BCL2 inhibitors, BET inhibitors, EZH2 inhibitors, DOT1L inhibitors and pharmaceutically acceptable salts thereof.

In detail, the present invention provides a therapeutic combination comprising an LSD1 inhibitor or a pharmaceutically acceptable salt thereof, and one or more active pharmaceutical ingredients selected from BCL2 inhibitors, BET inhibitors and pharmaceutically acceptable salts thereof.

In detail, the present invention provides a therapeutic combination comprising an LSD1 inhibitor or a pharmaceutically acceptable salt thereof, and one BCL2 inhibitor or a pharmaceutically acceptable salt thereof.

In detail, the present invention provides a therapeutic combination comprising an LSD1 inhibitor or a pharmaceutically acceptable salt thereof, and one BCL2 inhibitor selected from the list of ABT-199, ABT-263, ABT-737, Obatoclax, TW-37 and a pharmaceutically acceptable salt thereof.

In detail, the present invention provides a therapeutic combination comprising an LSD1 inhibitor or a pharmaceutically acceptable salt thereof, and one BET inhibitor or a pharmaceutically acceptable salt thereof.

In detail, the present invention provides a therapeutic combination comprising an LSD1 inhibitor or a pharmaceutically acceptable salt thereof, and one BET inhibitor selected from the list of CPI-203, GSK1324726A, GSK1210151A, (+)-JQ1, MS 436, OTX015 and a pharmaceutically acceptable salt thereof.

In detail, the present invention provides a therapeutic combination comprising an LSD1 inhibitor or a pharmaceutically acceptable salt thereof, and one EZH2 inhibitor or a pharmaceutically acceptable salt thereof.

In detail, the present invention provides a therapeutic combination comprising an LSD1 inhibitor or a pharmaceutically acceptable salt thereof, and one EZH2 inhibitor selected from the list of CPI-169, EPZ005687, EPZ-6438, GSK126, GSK343 and a pharmaceutically acceptable salt thereof.

In detail, the present invention provides a therapeutic combination comprising an LSD1 inhibitor or a pharmaceutically acceptable salt thereof, and one DOT1L inhibitor or a pharmaceutically acceptable salt thereof.

In detail, the present invention provides a therapeutic combination comprising an LSD1 inhibitor or a pharmaceutically acceptable salt thereof, and one DOT1L inhibitor selected from the list of EPZ-004777, EPZ-5676, SGC 0946 and a pharmaceutically acceptable salt thereof.

In detail, the present invention provides a therapeutic combination comprising an LSD1 inhibitor or a pharmaceutically acceptable salt thereof, and one Chk inhibitor or a pharmaceutically acceptable salt thereof.

In detail, the present invention provides a therapeutic combination comprising an LSD1 inhibitor or a pharmaceutically acceptable salt thereof, and one Chk inhibitor selected from LY2603618 and a pharmaceutically acceptable salt thereof.

In detail, the present invention provides a therapeutic combination comprising an LSD1 inhibitor or a pharmaceutically acceptable salt thereof, and one DNA alkylating agent or a pharmaceutically acceptable salt thereof.

In detail, the present invention provides a therapeutic combination comprising an LSD1 inhibitor or a pharmaceutically acceptable salt thereof, and one DNA alkylating agent selected from the list of Bendamustine, Carboplatin, Cisplatin, Temozolomide and a pharmaceutically acceptable salt thereof.

In detail, the present invention provides a therapeutic combination comprising an LSD1 inhibitor or a pharmaceutically acceptable salt thereof, and one HDAC inhibitor or a pharmaceutically acceptable salt thereof.

In detail, the present invention provides a therapeutic combination comprising an LSD1 inhibitor or a pharmaceutically acceptable salt thereof, and one HDAC inhibitor selected from the list of ACY-1215, Belinostat, Panobinostat, SAHA, SNDX-275 or and a pharmaceutically acceptable salt thereof.

In detail, the present invention provides a therapeutic combination comprising an LSD1 inhibitor or a pharmaceutically acceptable salt thereof, and one topoisomerase inhibitor or a pharmaceutically acceptable salt thereof.

In detail, the present invention provides a therapeutic combination comprising an LSD1 inhibitor or a pharmaceutically acceptable salt thereof, and one topoisomerase inhibitor selected from the list of Etoposide, Irinotecan, Topotecan and a pharmaceutically acceptable salt thereof.

In detail, the present invention provides a therapeutic combination comprising an LSD1 inhibitor or a pharmaceutically acceptable salt thereof, and one Aurora kinase inhibitor or a pharmaceutically acceptable salt thereof.

In detail, the present invention provides a therapeutic combination comprising an LSD1 inhibitor or a pharmaceutically acceptable salt thereof, and one Aurora kinase inhibitor selected from the list of MLN8237 and a pharmaceutically acceptable salt thereof.

In detail, the present invention provides a therapeutic combination comprising an LSD1 inhibitor or a pharmaceutically acceptable salt thereof, and one anti-mitotic agent or a pharmaceutically acceptable salt thereof.

In detail, the present invention provides a therapeutic combination comprising an LSD1 inhibitor or a pharmaceutically acceptable salt thereof, and one anti-mitotic agent selected from Docetaxel, Paclitaxel, Vincristine and a pharmaceutically acceptable salt thereof.

In one embodiment, the present invention provides a therapeutic combination comprising an LSD1 inhibitor or a pharmaceutically acceptable salt thereof, a topoisomerase inhibitor or a pharmaceutically acceptable salt thereof, and a DNA alkylating agent or a pharmaceutically acceptable salt thereof.

In one embodiment, the present invention provides a therapeutic combination comprising (trans)-N1-((1R,2S)-2-phenylcyclopropyl)cyclohexane-1,4-diamine or a pharmaceutically acceptable salt thereof, a topoisomerase inhibitor or a pharmaceutically acceptable salt thereof, and a DNA alkylating agent or a pharmaceutically acceptable salt thereof.

In one embodiment, the present invention provides a therapeutic combination comprising an LSD1 inhibitor or a pharmaceutically acceptable salt thereof, etoposide or a pharmaceutically acceptable salt thereof, and carboplatin or a pharmaceutically acceptable salt thereof.

In one embodiment, the present invention provides a therapeutic combination comprising (trans)-N1-((1R,2S)-2-phenylcyclopropyl)cyclohexane-1,4-diamine or a pharmaceutically acceptable salt thereof, etoposide or a pharmaceutically acceptable salt thereof, and carboplatin or a pharmaceutically acceptable salt thereof.

In one embodiment of the invention, the therapeutic combination yields a synergy score above 6.4, particularly above 8, more particularly above 10, most particularly above 15.

In one embodiment of the invention, the therapeutic combination yields a synergy score above 6.4, particularly above 8, more particularly above 10, most particularly above 15, wherein the synergy score was calculated as:

$$\text{Synergy Score} = \log f_X \log f_Y \Sigma \max(0, I_{data}) (I_{data} - I_{Loewe})$$

LSD1 Inhibitors

In one aspect of the present invention, the LSD1 inhibitor is selected from a compound as described in WO 2011/131697[2], WO 2012135113[3] and WO 2013/057322[4].

In a particular embodiment of the invention the LSD1 inhibitor is selected from the list of:

4-[[4-[[[(1R,2S)-2-phenylcyclopropyl]amino]methyl]-1-piperidinyl]methyl]-benzoic acid, (trans)-N1-((1R,2S)-2-phenylcyclopropyl)cyclohexane-1,4-diamine, (R)-1-(4-(((trans)-2-phenylcyclopropyl)amino)cyclohexyl) pyrrolidin-3-amine, 4-(aminomethyl)-N-((trans)-2-phenylcyclopropyl)cyclohexanamine, N1-((trans)-2-phenylcyclopropyl)cyclohexane-1,3-diamine, N1-((trans)-2-phenylcyclopropyl)cyclobutane-1,3-diamine, N1-((trans)-2-phenylcyclopropyl)-2,3-dihydro-1H-indene-1,3-diamine, N1-methyl-N4-((trans)-2-phenylcyclopropyl)cyclohexane-1,4-diamine, N1-((trans)-2-(4-bromophenyl)cyclopropyl)cyclohexane-1,4-diamine, N1-(2-(o-tolyl)cyclopropyl)cyclohexane-1,4-diamine, N1-(2-(4-methoxyphenyl)cyclopropyl)cyclohexane-1,4-diamine, N1-(2-(2-fluorophenyl)cyclopropyl)cyclohexane-1,4-diamine, N1-(2-(naphthalen-2-yl)cyclopropyl)cyclohexane-1,4-diamine, N-(4'-((trans)-2-((4-aminocyclohexyl)amino)cyclopropyl)-[1,1'-biphenyl]-3-yl)-2-cyanobenzenesulfonamide, N1-((trans)-2-(4-(pyridin-3-ylmethoxy)phenyl)cyclopropyl) cyclohexane-1,4-diamine, and a pharmaceutically acceptable salt thereof.

In a particular embodiment of the invention the LSD1 inhibitor is selected from the list of:

4-[[4-[[[(1R,2S)-2-phenylcyclopropyl]amino]methyl]-1-piperidinyl]methyl]-benzoic acid, (trans)-N1-((1R,2S)-2-phenylcyclopropyl)cyclohexane-1,4-diamine, (R)-1-(4-(((trans)-2-phenylcyclopropyl)amino)cyclohexyl) pyrrolidin-3-amine, 4-(aminomethyl)-N-((trans)-2-phenylcyclopropyl)cyclohexanamine, N1-((trans)-2-phenylcyclopropyl)cyclohexane-1,3-diamine, N1-((trans)-2-phenylcyclopropyl)cyclobutane-1,3-diamine, N1-((trans)-2-phenylcyclopropyl)-2,3-dihydro-1H-indene-1,3-diamine, N1-methyl-N4-((trans)-2-phenylcyclopropyl)cyclohexane-1,4-diamine, N1-((trans)-2-(4-bromophenyl)cyclopropyl)cyclohexane-1,4-diamine, N1-(2-(o-tolyl)cyclopropyl)cyclohexane-1,4-diamine, N1-(2-(4-methoxyphenyl)cyclopropyl)cyclohexane-1,4-diamine, N1-(2-(2-fluorophenyl)cyclopropyl)cyclohexane-1,4-diamine, N1-(2-(naphthalen-2-yl)cyclopropyl)cyclohexane-1,4-diamine,
N-(4'-((trans)-2-((4-aminocyclohexyl)amino)cyclopropyl)-[1,1'-biphenyl]-3-yl)-2-cyanobenzenesulfonamide, and
N1-((trans)-2-(4-(pyridin-3-ylmethoxy)phenyl)cyclopropyl) cyclohexane-1,4-diamine,
or a pharmaceutically acceptable salt thereof.

In a particular embodiment of the invention the LSD1 inhibitor is selected from the list of:
4-[[4-[[[(1R,2S)-2-phenylcyclopropyl]amino]methyl]-1-piperidinyl]methyl]-benzoic acid (trans)-N1-((1R,2S)-2-phenylcyclopropyl)cyclohexane-1,4-diamine,
(R)-1-(4-(((trans)-2-phenylcyclopropyl)amino)cyclohexyl) pyrrolidin-3-amine,
4-(aminomethyl)-N-((trans)-2-phenylcyclopropyl)cyclohexanamine,
N1-((trans)-2-phenylcyclopropyl)cyclohexane-1,3-diamine,
N1-((trans)-2-phenylcyclopropyl)cyclobutane-1,3-diamine,
N1-((trans)-2-phenylcyclopropyl)-2,3-dihydro-1H-indene-1,3-diamine,
N1-methyl-N4-((trans)-2-phenylcyclopropyl)cyclohexane-1,4-diamine,
N1-((trans)-2-(4-bromophenyl)cyclopropyl)cyclohexane-1,4-diamine,
N1-(2-(o-tolyl)cyclopropyl)cyclohexane-1,4-diamine,
N1-(2-(4-methoxyphenyl)cyclopropyl)cyclohexane-1,4-diamine,
N1-(2-(2-fluorophenyl)cyclopropyl)cyclohexane-1,4-diamine,
N1-(2-(naphthalen-2-yl)cyclopropyl)cyclohexane-1,4-diamine,
N-(4'-((trans)-2-((4-aminocyclohexyl)amino)cyclopropyl)-[1,1'-biphenyl]-3-yl)-2-cyanobenzenesulfonamide,
N1-((trans)-2-(4-(pyridin-3-ylmethoxy)phenyl)cyclopropyl) cyclohexane-1,4-diamine,
and a pharmaceutically acceptable salt thereof.

In a particular embodiment of the invention the LSD1 inhibitor is GSK2879552 [CAS Reg. No. 1401966-69-5], also known as 4-[[4-[[[(1R,2S)-2-phenylcyclopropyl]amino]methyl]-1-piperidinyl]methyl]-benzoic acid, or a pharmaceutically acceptable salt thereof.

In a particular embodiment of the invention the LSD1 inhibitor is selected from the list of:
(trans)-N1-((1R,2S)-2-phenylcyclopropyl)cyclohexane-1,4-diamine,
(R)-1-(4-(((trans)-2-phenylcyclopropyl)amino)cyclohexyl) pyrrolidin-3-amine,
4-(aminomethyl)-N-((trans)-2-phenylcyclopropyl)cyclohexanamine,
N1-((trans)-2-phenylcyclopropyl)cyclohexane-1,3-diamine,
N1-((trans)-2-phenylcyclopropyl)cyclobutane-1,3-diamine,
N1-((trans)-2-phenylcyclopropyl)-2,3-dihydro-1H-indene-1,3-diamine,
N1-methyl-N4-((trans)-2-phenylcyclopropyl)cyclohexane-1,4-diamine,
N1-((trans)-2-(4-bromophenyl)cyclopropyl)cyclohexane-1,4-diamine,
N1-(2-(o-tolyl)cyclopropyl)cyclohexane-1,4-diamine,
N1-(2-(4-methoxyphenyl)cyclopropyl)cyclohexane-1,4-diamine,
N1-(2-(2-fluorophenyl)cyclopropyl)cyclohexane-1,4-diamine,
N1-(2-(naphthalen-2-yl)cyclopropyl)cyclohexane-1,4-diamine,
N-(4'-((trans)-2-((4-aminocyclohexyl)amino)cyclopropyl)-[1,1'-biphenyl]-3-yl)-2-cyanobenzenesulfonamide,
N1-((trans)-2-(4-(pyridin-3-ylmethoxy)phenyl)cyclopropyl) cyclohexane-1,4-diamine,
and a pharmaceutically acceptable salt thereof.

In a particular embodiment of the invention the LSD1 inhibitor is (trans)-N1-((1R,2S)-2-phenylcyclopropyl)cyclohexane-1,4-diamine [CAS Reg. No. 1431304-21-0] or a pharmaceutically acceptable salt thereof.

In a particular embodiment of the invention the LSD1 inhibitor is (trans)-N1-((1R,2S)-2-phenylcyclopropyl)cyclohexane-1,4-diamine [CAS Reg. No. 1431304-21-0] or a hydrochloride salt thereof.

In a particular embodiment of the invention the LSD1 inhibitor is (trans)-N1-((1R,2S)-2-phenylcyclopropyl)cyclohexane-1,4-diamine bis-hydrochloride [CAS Reg. No. 1431303-72-8].

Combination Therapies

The therapeutic combinations may be used for the treatment of a hyperproliferative disease or disorder, including tumors, cancers, and neoplastic tissue, along with pre-malignant and non-neoplastic or non-malignant hyperproliferative disorders. In certain embodiments, a combination of the invention is combined in a dosing regimen as combination therapy, with another compound that has anti-hyperproliferative properties or that is useful for treating the hyperproliferative disorder. The additional compound of the dosing regimen preferably has complementary activities to the combination, and such that they do not adversely affect each other. Such compounds may be administered in amounts that are effective for the purpose intended. In one embodiment, the therapeutic combination is administered by a dosing regimen wherein the therapeutically effective amount of an LSD1 inhibitor or a pharmaceutically acceptable salt thereof, or a pharmaceutically acceptable salt thereof is administered in a range from twice daily to once every three weeks (q3wk), and the therapeutically effective amount of one or more active pharmaceutical ingredients selected from a compound of Table 2 and pharmaceutically acceptable salts thereof is administered in a range from twice daily to once every three weeks.

The combination therapy may be administered as a simultaneous or sequential regimen. When administered sequentially, the combination may be administered in two or more administrations. The combined administration includes coadministration, using separate formulation, and consecutive administration in either order, wherein preferably there is a time period while both (or all) active agents simultaneously exert their biological activities.

In one specific aspect of the invention, the LSD1 inhibitor or a pharmaceutically acceptable salt thereof can be administered for a time period of about 1 to about 10 days after administration of the one or more active pharmaceutical ingredients selected from a compound of Table 2 and pharmaceutically acceptable salts thereof begins. In another specific aspect of the invention, the LSD1 inhibitor or a pharmaceutically acceptable salt thereof can be administered for a time period of about 1 to 10 days before administration of the one or more active pharmaceutical ingredients selected from a compound of Table 2 and pharmaceutically acceptable salts thereof begins. In another specific aspect of the invention, administration of the LSD1 inhibitor or a pharmaceutically acceptable salt thereof and administration of the one or more active pharmaceutical ingredients selected from a compound of Table 2 and pharmaceutically acceptable salts thereof begin on the same day.

In one specific aspect of the invention, the one or more active pharmaceutical ingredients selected from a compound of Table 2 and pharmaceutically acceptable salts thereof can be administered for a time period of about 1 to about 10 days after administration of the LSD1 inhibitor or a pharmaceutically acceptable salt thereof begins. In another specific aspect of the invention, the one or more active pharmaceutical ingredients selected from a compound of Table 2 and pharmaceutically acceptable salts thereof can be administered for a time period of about 1 to 10 days before administration of the LSD1 inhibitor or a pharmaceutically acceptable salt thereof begins. In another specific aspect of the invention, administration of one or more active pharmaceutical ingredients selected from a compound of Table 2 and pharmaceutically acceptable salts thereof and administration of the LSD1 inhibitor or a pharmaceutically acceptable salt thereof begin on the same day.

Suitable dosages for any of the above co-administered agents are those presently used and may be lowered due to the combined action (synergy) of the newly identified agent and other chemotherapeutic agents or treatments, such as to increase the therapeutic index or mitigate toxicity or other side-effects or consequences.

In a particular embodiment of anti-cancer therapy, the therapeutic combination may be combined with surgical therapy and radiotherapy. The amounts of the combination and the relative timings of administration will be selected in order to achieve the desired combined therapeutic effect.

In one particular embodiment of the invention, the SCLC cells are sensitized through administration of an LSD1 inhibitor prior to administration of the therapeutic combinations as described herein.

In one particular embodiment of the invention, the SCLC cells are sensitized through administration of (trans)-N1-((1R,2S)-2-phenylcyclopropyl)cyclohexane-1,4-diamine, or a pharmaceutically acceptable salt thereof, prior to administration of the therapeutic combinations as described herein.

In one particular embodiment of the invention, the SCLC cells are sensitized through administration of (trans)-N1-((1R,2S)-2-phenylcyclopropyl)cyclohexane-1,4-diamine, or a pharmaceutically acceptable salt thereof, five days on/two days off (5/2) for three weeks prior to administration of the therapeutic combinations as described herein.

In one particular embodiment of the invention, the SCLC cells are sensitized through administration of (trans)-N1-((1R,2S)-2-phenylcyclopropyl)cyclohexane-1,4-diamine, or a pharmaceutically acceptable salt thereof, at a dose of 40 µg per kg (upk) five days on/two days off (5/2) for three weeks prior to administration of the therapeutic combinations as described herein.

In one particular embodiment of the invention, the SCLC cells are sensitized through administration of (trans)-N1-((1R,2S)-2-phenylcyclopropyl)cyclohexane-1,4-diamine, or a pharmaceutically acceptable salt thereof, at a dose of 40 µg per kg (upk) five days on/two days off (5/2) for three weeks prior to administration of a therapeutic combination comprising Etoposide, Carboplatin and (trans)-N1-((1R,2S)-2-phenylcyclopropyl)cyclohexane-1,4-diamine, or a pharmaceutically acceptable salt thereof.

In one particular embodiment of the invention, the SCLC cells are sensitized through administration of (trans)-N1-((1R,2S)-2-phenylcyclopropyl)cyclohexane-1,4-diamine, or a pharmaceutically acceptable salt thereof, at a dose of 40 µg per kg (upk) five days on/two days off (5/2) for three weeks prior to administration of a therapeutic combination comprising Etoposide at a dose of 5 mg per kg (mpk) daily for five days (qd×5), Carboplatin at a dose of 100 mpk weekly for three weeks (qwk×3) and (trans)-N1-((1R,2S)-2-phenylcyclopropyl)cyclohexane-1,4-diamine, or a pharmaceutically acceptable salt thereof, at a dose of 20 upk five days on/two days off for three weeks.

One particular embodiment of the invention relates to a method for the treatment of a neoplastic disease, which method comprises sensitizing through administration of an LSD1 inhibitor followed by administering an effective amount of a therapeutic combination as described herein to a human being or animal.

One particular embodiment of the invention relates to a method for the treatment of a neoplastic disease, which method comprises sensitizing through administration of (trans)-N1-((1R,2S)-2-phenylcyclopropyl)cyclohexane-1,4-diamine or a pharmaceutically acceptable salt thereof followed by administering an effective amount of a therapeutic combination as described herein to a human being or animal.

One particular embodiment of the invention relates to a method for the treatment of a neoplastic disease, which method comprises sensitizing through administration of (trans)-N1-((1R,2S)-2-phenylcyclopropyl)cyclohexane-1,4-diamine or a pharmaceutically acceptable salt thereof five days on/two days off (5/2) for three weeks followed by administering an effective amount of a therapeutic combination as described herein to a human being or animal.

One particular embodiment of the invention relates to a method for the treatment of a neoplastic disease, which method comprises sensitizing through administration of (trans)-N1-((1R,2S)-2-phenylcyclopropyl)cyclohexane-1,4-diamine or a pharmaceutically acceptable salt thereof at a dose of 40 µg per kg (upk) five days on/two days off (5/2) for three weeks followed by administering an effective amount of a therapeutic combination as described herein to a human being or animal.

One particular embodiment of the invention relates to a method for the treatment of a neoplastic disease, which method comprises sensitizing through administration of (trans)-N1-((1R,2S)-2-phenylcyclopropyl)cyclohexane-1,4-diamine or a pharmaceutically acceptable salt thereof at a dose of 40 µg per kg (upk) five days on/two days off (5/2) for three weeks followed by administering an effective amount of a therapeutic combination comprising Etoposide, Carboplatin and (trans)-N1-((1R,2S)-2-phenylcyclopropyl)cyclohexane-1,4-diamine to a human being or animal.

One particular embodiment of the invention relates to a method for the treatment of a neoplastic disease, which method comprises sensitizing through administration of (trans)-N1-((1R,2S)-2-phenylcyclopropyl)cyclohexane-1,4-diamine or a pharmaceutically acceptable salt thereof at a dose of 40 µg per kg (upk) five days on/two days off (5/2) for three weeks followed by administering an effective amount of a therapeutic combination comprising Etoposide at a dose of 5 mg per kg (mpk) daily for five days (qd×5), Carboplatin at a dose of 100 mpk weekly for three weeks (qwk×3) and (trans)-N1-((1R,2S)-2-phenylcyclopropyl)cyclohexane-1,4-diamine at a dose of 20 upk five days on/two days off for three weeks to a human being or animal.

Pharmaceutical Compositions

Another embodiment provides pharmaceutical compositions or medicaments comprising a therapeutic combination as described herein and a pharmaceutically acceptable excipient.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The therapeutic combinations as described herein may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The therapeutic combinations as described herein may be administered in any convenient administrative form, e.g., tablets, powders, capsules, solutions, dispersions, suspensions, syrups, sprays, suppositories, gels, emulsions, patches, etc. Such compositions may comprise components conventional in pharmaceutical preparations, e.g., diluents, carriers, pH modifiers, preservatives, solubilizers, stabilizers, wetting agents, emulsifiers, sweeteners, colorants, flavorants, salts for varying the osmotic pressure, buffers, masking agents, antioxidants, and further active agents. They can also comprise still other therapeutically valuable substances.

A typical formulation is prepared by mixing a therapeutic combination as described herein and a pharmaceutically acceptable excipient. Suitable excipients are well known to those skilled in the art and are described in detail in, e.g., Ansel H. C. et al.[103]; Rowe R. C.[104] and Gennaro A. R. et al.[105]. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

The dosage at which therapeutic combination as described herein can be administered can vary within wide limits and will, of course, be fitted to the individual requirements in each particular case.

An example of a suitable oral dosage form is a tablet comprising about 0.01 mg to 10 mg of a therapeutic combination as described herein compounded with about 90 to 30 mg anhydrous lactose, about 5 to 40 mg sodium croscarmellose, about 5 to 30 mg polyvinylpyrrolidone (PVP) K30, and about 1 to 10 mg magnesium stearate. The powdered ingredients are first mixed together and then mixed with a solution of the PVP. The resulting composition can be dried, granulated, mixed with the magnesium stearate and compressed to tablet form using conventional equipment.

An example of an aerosol formulation can be prepared by dissolving a therapeutic combination as described herein, for example 0.1 to 100 mg, in a suitable buffer solution, e.g. a phosphate buffer, adding a tonicifier, e.g. a salt such as sodium chloride, if desired. The solution may be filtered, e.g., using a 0.2 µm filter, to remove impurities and contaminants.

Another embodiment relates to a pharmaceutical composition comprising a therapeutic combination as described herein and one or more pharmaceutically acceptable excipient.

Articles of Manufacture

In another embodiment of the invention, an article of manufacture, or "kit", containing a combination useful for the treatment of the diseases and disorders described above is provided.

In one embodiment, the kit comprises a container and a therapeutic combination as described herein.

One embodiment of the invention provides an article of manufacture comprising a therapeutic combination as described herein useful in the treatment of a neoplastic disease.

The kit may further comprise a label or package insert, on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold a combination, or a formulation thereof, which is effective for treating the condition and may have a sterile access port (for example, the container may be an intravenous solution bag or a vial having a stopper pierceable by a hypodermic injection needle). The label or package insert indicates that the composition is used for treating the condition of choice, such as cancer. In one embodiment, the label or package inserts indicates that the composition comprising the combination can be used to treat a disorder resulting from abnormal cell growth. The label or package insert may also indicate that the composition can be used to treat other disorders. Alternatively, or additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the combination, and, if present, the second pharmaceutical formulation. For example, if the kit comprises a first composition comprising the LSD1 inhibitor or a pharmaceutically acceptable salt thereof and a second pharmaceutical formulation comprising one or more active pharmaceutical ingredients selected from a compound of Table 2 and pharmaceutically acceptable salts thereof, the kit may further comprise directions for the simultaneous, sequential or separate administration of the first and second pharmaceutical compositions to a patient in need thereof.

In another embodiment, the kits are suitable for the delivery of solid oral forms of a combination, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, a kit may comprise (a) a first container with the LSD1 inhibitor or a pharmaceutically acceptable salt thereof contained therein; (b) a second container with one or more active pharmaceutical ingredients selected from a compound of Table 2 and pharmaceutically acceptable salts thereof and (c) a third container with a third pharmaceutical formulation contained therein, wherein the third pharmaceutical formulation comprises another compound with anti-hyperproliferative activity. Alternatively, or additionally, the kit may comprise another container comprising a pharmaceutically-acceptable buffer, such as bacteriostatic water for injection (BWFI), phosphate-buffered saline, Ringer's solution and dextrose solution. It may further include other materials desirable from a commercial and 5 user standpoint, including other buffers, diluents, filters, needles, and syringes.

Where the kit comprises a composition of the LSD1 inhibitor or a pharmaceutically acceptable salt thereof and one or more active pharmaceutical ingredients selected from a compound of Table 2 and pharmaceutically acceptable salts thereof, the kit may comprise a container for containing the separate compositions such as a divided bottle or a divided foil packet, however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

Medical Uses and Methods of Treatment

Another embodiment relates to a therapeutic combination as described herein for use as therapeutically active substance.

Another embodiment relates to a therapeutic combination as described herein for use in the treatment of a neoplastic disease.

Another embodiment relates to a method for the treatment of a neoplastic disease, which method comprises administering an effective amount of a therapeutic combination as described herein to a human being or animal.

Another embodiment relates to the use of a therapeutic combination as described herein for the treatment of a neoplastic disease.

Another embodiment relates to the use of a therapeutic combination as described herein for the preparation of medicaments useful in the treatment of a neoplastic disease.

In a particular embodiment of the invention the therapeutic combination as described herein is administered to a patient in need thereof orally, such as an oral solution.

In a particular embodiment of the invention the neoplastic disease that is potentially treatable by the therapeutic combination as described herein is a cancer, particularly a cancer selected from the group consisting of breast cancer, prostate cancer, cervical cancer, ovarian cancer, gastric cancer, colorectal cancer (i.e. including colon cancer and rectal cancer), pancreatic cancer, liver cancer, brain cancer, neuroendocrine cancer, lung cancer, kidney cancer, hematological malignancies, melanoma and sarcomas.

In a particular embodiment of the invention the cancer that is potentially treatable by the therapeutic combination as described herein is selected from the group consisting of hematological malignancies, neuroendocrine cancer, breast cancer, cervical cancer, ovarian cancer, colorectal cancer, melanoma and lung cancer.

In a particular embodiment of the invention the neoplastic disease is a cancer selected from the group consisting of blood cancer or lung cancer, more particularly acute myelogenous leukemia (AML), chronic myelogenous leukemia (CML), chronic neutrophilic leukemia, chronic eosinophilic leukemia, chronic lymphocytic leukemia (CLL), acute lymphoblastic leukemia (ALL), hairy cell leukemia, small cell lung carcinoma (SCLC) and non-small-cell lung carcinoma (NSCLC).

In a particular embodiment of the invention the neoplastic disease is a blood cancer or lung cancer selected from the group of acute myelogenous leukemia (AML), chronic myelogenous leukemia (CML), chronic neutrophilic leukemia, chronic eosinophilic leukemia, chronic lymphocytic leukemia (CLL), acute lymphoblastic leukemia (ALL), hairy cell leukemia, small cell lung carcinoma (SCLC) and non-small-cell lung carcinoma (NSCLC).

In a particular embodiment of the invention the neoplastic disease is a cancer is selected from the group consisting of acute myeloid leukemia (AML), non-Hodgkin's lymphoma, small cell lung cancer (SCLC), thyroid cancer, and melanoma.

In a particular embodiment of the invention the neoplastic disease is a cancer selected from the group consisting of acute myeloid leukemia (AML), thyroid cancer, melanoma, or small cell lung cancer (SCLC).

In a particular embodiment of the invention the neoplastic disease is a cancer selected from the group consisting of acute myeloid leukemia (AML) and small cell lung cancer (SCLC).

In a particular embodiment of the invention the neoplastic disease is neuroendocrine cancer.

In a particular embodiment of the invention the neoplastic disease is a solid tumor.

In a particular embodiment of the invention the neoplastic disease is a malignant solid tumor selected from sarcomas, carcinomas, and lymphomas.

In a particular embodiment of the invention the neoplastic disease is lung cancer.

In a particular embodiment of the invention the neoplastic disease is small cell lung cancer (SCLC).

In a particular embodiment of the invention the neoplastic disease is small cell lung cancer (SCLC), wherein the SCLC cells are is sensitive to LSD1 inhibitor-based therapy.

In a particular embodiment of the invention the neoplastic disease is small cell lung cancer (SCLC), wherein the SCLC cells are sensitive to LSD1 inhibitor-based therapy, wherein the sensitivity to LSD 1 inhibitor-based therapy is assessed based on predictive mRNA expression levels as described herein.

In a particular embodiment of the invention the neoplastic disease is small cell lung cancer (SCLC), wherein the SCLC cells are sensitive to LSD1 inhibitor-based therapy, wherein the sensitivity to LSD 1 inhibitor-based therapy is assessed using an in vitro method comprising:
   a) measuring in a sample from the patient the levels of a gene panel, wherein the gene panel comprises one or more genes selected from responder genes and non-responder genes,
   b) calculating a signature score from the measured levels of the gene panel,
   c) comparing the signature score calculated to a threshold level, and
   d) identifying the patient as more likely to respond to the therapy comprising an LSD1 inhibitor when the signature score is above the threshold level.

In a particular embodiment of the invention the neoplastic disease is small cell lung cancer (SCLC), wherein the SCLC cells exhibit response to single agent treatment with LSD1 inhibitors.

In a particular embodiment of the invention the neoplastic disease is small cell lung cancer (SCLC), wherein the SCLC cells exhibit response to single agent treatment with LSD1 inhibitors, wherein the response to single agent treatment with LSD1 inhibitors is assessed based on predictive mRNA expression levels as described herein.

In a particular embodiment of the invention the neoplastic disease is small cell lung cancer (SCLC), wherein the SCLC cells exhibit response to single agent treatment with LSD1 inhibitors, wherein the response to single agent treatment with LSD1 inhibitors is assessed using an in vitro method comprising:
- a) measuring in a sample from the patient the levels of a gene panel, wherein the gene panel comprises one or more genes selected from responder genes and non-responder genes,
- b) calculating a signature score from the measured levels of the gene panel,
- c) comparing the signature score calculated to a threshold level, and
- d) identifying the patient as more likely to respond to the therapy comprising an LSD1 inhibitor when the signature score is above the threshold level.

Gene Panels and mRNA Signatures

Table 3 provides a list including description of the genes employed in present invention.

TABLE 3

Description of the genes employed in the invention

| Gene | Ensembl Gene ID* | Description | Synonyms | Location: Chromosome |
|---|---|---|---|---|
| ASCL1 | ENSG00000139352 | achaete-scute family bHLH transcription factor 1 | ASH1, bHLHa46, HASH1 | Chromosome 12: 102, 957, 686-102, 960, 516 forward strand. |
| DDC | ENSG00000132437 | dopa decarboxylase | AADC | Chromosome 7: 50, 458, 436-50, 565, 457 reverse strand. |
| CEACAM6 | ENSG00000086548 | carcinoembryonic antigen-related cell adhesion molecule 6 | CD66c, NCA | Chromosome 19: 41, 750, 977-41, 772, 208 forward strand. |
| LRRIQ4 | ENSG00000188306 | leucine-rich repeats and IQ motif containing 4 | LRRC64 | Chromosome 3: 169, 821, 922-169, 837, 775 forward strand. |
| NR0B2 | ENSG00000131910 | nuclear receptor subfamily 0, group B, member 2 | SHP | Chromosome 1: 26, 911, 489-26, 913, 966 reverse strand. |
| GRP | ENSG00000134443 | gastrin-releasing peptide | | Chromosome 18: 59, 220, 168-59, 230, 774 forward strand. |
| CEACAM5 | ENSG00000105388 | carcinoembryonic antigen-related cell adhesion molecule 5 | CD66e, CEA | Chromosome 19: 41, 576, 273-41, 729, 798 forward strand. |
| SOX21 | ENSG00000125285 | SRY (sex determining region Y)-box 21 | SOX25 | Chromosome 13: 94, 709, 622-94, 712, 399 reverse strand. |
| OR51E2 | ENSG00000167332 | olfactory receptor, family 51, subfamily E, member 2 | PSGR | Chromosome 11: 4, 680, 171-4, 697, 854 reverse strand. |
| SEC11C | ENSG00000166562 | SEC11 homolog C, signal peptidase complex subunit | SEC11L3, SPC21, SPCS4C | Chromosome 18: 59, 139, 477-59, 158, 836 forward strand. |
| BAALC | ENSG00000164929 | brain and acute leukemia, cytoplasmic | | Chromosome 8: 103, 140, 710-103, 230, 305 forward strand. |
| CCDC40 | ENSG00000141519 | coiled-coil domain containing 40 | CILD15, FAP172, FLJ20753, FLJ32021, KIAA1640 | Chromosome 17: 80, 036, 632-80, 100, 613 forward strand. |
| RAB3B | ENSG00000169213 | RAB3B, member RAS oncogene family | | Chromosome 1: 51, 907, 956-51, 990, 764 reverse strand. |
| RGS17 | ENSG00000091844 | regulator of G-protein signaling 17 | RGS-17, RGSZ2 | Chromosome 6: 153, 004, 459-153, 131, 249 reverse strand. |
| ABCE1 | ENSG00000164163 | ATP-binding cassette, sub-family E (OABP), member 1 | OABP, RLI, RNASEL1, RNASELI, RNS4I | Chromosome 4: 145, 097, 932-145, 129, 179 forward strand. |
| ETS2 | ENSG00000157557 | v-ets avian erythroblastosis virus E26 oncogene homolog 2 | | Chromosome 21: 38, 805, 307-38, 824, 955 forward strand. |
| CCDC154 | ENSG00000197599 | coiled-coil domain containing 154 | C16orf29, LOC645811 | Chromosome 16: 1, 434, 383-1, 444, 556 reverse strand. |
| SPAG6 | ENSG00000077327 | sperm associated antigen 6 | CT141, pf16, Repro-SA-1 | Chromosome 10: 22, 345, 445-22, 454, 224 forward strand. |

TABLE 3-continued

Description of the genes employed in the invention

| Gene | Ensembl Gene ID* | Description | Synonyms | Location: Chromosome |
|---|---|---|---|---|
| PON1 | ENSG00000005421 | paraoxonase 1 | ESA, PON | Chromosome 7: 95, 297, 676-95, 324, 707 reverse strand. |
| TMEM176A | ENSG00000002933 | transmembrane protein 176A | HCA112, MS4B1 | Chromosome 7: 150, 800, 403-150, 805, 120 forward strand. |
| C1orf127 | ENSG00000175262 | chromosome 1 open reading frame 127 | FLJ37118 | Chromosome 1: 10, 946, 471-10, 982, 037 reverse strand. |
| IGF2BP2 | ENSG00000073792 | insulin-like growth factor 2 mRNA binding protein 2 | IMP-2 | Chromosome 3: 185, 643, 739-185, 825, 056 reverse strand. |
| IGFBP5 | ENSG00000115461 | insulin-like growth factor binding protein 5 | | Chromosome 2: 216, 672, 105-216, 695, 525 reverse strand. |
| FAM84A | ENSG00000162981 | family with sequence similarity 84, member A | FLJ35392, NSE1 | Chromosome 2: 14, 632, 686-14, 650, 814 forward strand. |
| FOXA2 | ENSG00000125798 | forkhead box A2 | HNF3B | Chromosome 20: 22, 581, 005-22, 585, 455 reverse strand. |
| HOXA10 | ENSG00000253293 | homeobox A10 | HOX1, HOX1H | Chromosome 7: 27, 170, 591-27, 180, 261 reverse strand. |
| MYC | ENSG00000136997 | v-myc avian myelocytomatosis viral oncogene homolog | bHLHe39, c-Myc, MYCC | Chromosome 8: 127, 735, 434-127, 741, 434 forward strand. |
| NCAM1 | ENSG00000149294 | neural cell adhesion molecule 1 | CD56, NCAM | Chromosome 11: 112, 961, 247-113, 278, 436 forward strand. |
| NCAM2 | ENSG00000154654 | neural cell adhesion molecule 2 | MGC51008, NCAM21 | Chromosome 21: 20, 998, 315-21, 543, 329 forward strand. |
| NEUROD1 | ENSG00000162992 | neuronal differentiation 1 | BETA2, BHF-1, bHLHa3, MODY6, NEUROD | Chromosome 2: 181, 673, 088-181, 680, 876 reverse strand. |
| KRT8 | ENSG00000170421 | keratin 8, type II | CARD2, CK8, CYK8, K2C8, K8, KO | Chromosome 12: 52, 897, 187-52, 949, 954 reverse strand. |
| ENO2 | ENSG00000111674 | enolase 2 (gamma, neuronal) | | Chromosome 12: 6, 913, 745-6, 923, 698 forward strand. |
| AVP | ENSG00000101200 | arginine vasopressin | ADH, ARVP | Chromosome 20: 3, 082, 556-3, 084, 724 reverse strand. |
| OXT | ENSG00000101405 | oxytocin/neurophysin I prepropeptide | OT, OT-NPI, OXT-NPI | Chromosome 20: 3, 071, 620-3, 072, 517 forward strand. |
| SYP | ENSG00000102003 | synaptophysin | MRX96 | Chromosome X: 49, 187, 804-49, 200, 259 reverse strand. |
| CHGA | ENSG00000100604 | chromogranin A | | Chromosome 14: 92, 923, 080-92, 935, 293 forward strand. |
| CHGB | ENSG00000089199 | chromogranin B | SCG1, SgI | Chromosome 20: 5, 911, 430-5, 925, 361 forward strand. |
| BCL2 | ENSG00000171791 | B-cell CLL/lymphoma 2 | Bcl-2, PPP1R50 | Chromosome 18: 63, 123, 346-63, 320, 128 reverse strand. |

(*http://www.ensembl.org/, Cunningham F. et al.[106]).

The present invention identifies a gene panel (also referred to as "multi-gene panel", "gene expression panel" or "panel of genes") whose mRNA expression signature based on in vitro data may serve to identify patients most likely to respond to LSD1 inhibitor containing therapy regimens. The genes listed are characteristic of the SCLC classic phenotype (generally of neuroendocrine origin) to the exclusion of those cell lines of "variant" phenotype. The expression of these genes may have predictive benefit in identifying responder patients of other histological subtypes in additional tumor settings.

It has been found that the mRNA signature is characterized by high expression in responder genes: ASCL1, HOXA10, NCAM1, NCAM2, NEUROD1, DDC, GRP, KRT8, ENO2, AVP, OXT, SYP, CHGA, CHGB, SOX21 and BCL2.

It has further been found, that non-responder lines may be characterized by high levels of the oncogene MYC.

The baseline expression levels of responder genes and non-responder genes listed herein may yield, alone or in combination with one another, a composite score that discriminates between cell lines and patient-derived clinical specimens that are resistant to therapy, and identifies those that are sensitive (responsive) to therapy using an LSD1 inhibitor.

Thus higher levels of responder genes and/or lower expression levels of non-responder genes are indicative for the response to a therapy using an LSD1 inhibitor. Combining the expression levels of several responder and/or non-responder genes may provide a multi-gene signature with improved confidence regarding responsiveness as compared to the readout from single gene expression levels.

The present invention identifies mRNAs associated with and for identifying responses to LSD1 inhibition.

The present invention also relates to a method for identifying sensitivity to LSD1 inhibitor-based therapy.

The present invention also relates to the use of a gene panel in order to determine a patient's response to a neoplastic disease when a patient is to be treated with an LSD1 inhibitor-based therapy.

The present invention also identifies mRNAs expression for monitoring the treatment of neoplastic diseases in a patient with an LSD1 inhibitor.

The present invention also provides the predictive mRNA values in determining the effectiveness of LSD1 inhibitor-based therapy to neoplastic diseases.

One embodiment of the invention provides an in vitro method of identifying a patient having a neoplastic disease as likely to respond to a therapy comprising an LSD1 inhibitor, the method comprising
a) measuring in a sample from the patient the levels of a gene panel, wherein the gene panel comprises one or more genes selected from responder genes and non-responder genes,
b) comparing the levels of the gene panel measured in a) to a reference level, and
c) identifying the patient as more likely to respond to the therapy comprising an LSD1 inhibitor when the levels of the responder genes of the gene panel measured in a) in the sample from the patient are above the reference level, and/or when the levels of the non-responder genes of the gene panel measured in a) in the sample from the patient are below the reference level.

One embodiment of the invention provides an in vitro method of identifying a patient having a neoplastic disease as likely to respond to a therapy comprising an LSD1 inhibitor, the method comprising
a) measuring in a sample from the patient the levels of a gene panel, wherein the gene panel comprises one or more genes selected from responder genes and non-responder genes,
b) calculating a signature score from the measured levels of the gene panel,
c) comparing the signature score calculated to a threshold level, and
d) identifying the patient as more likely to respond to the therapy comprising an LSD1 inhibitor when the signature score is above the threshold level.

Another embodiment of the invention provides an in vitro method of identifying a patient having a neoplastic disease as likely to respond to a therapy comprising an LSD1 inhibitor, the method comprising
a) measuring in a sample from the patient the levels of a gene panel, wherein the gene panel comprises one or more genes selected from responder genes and non-responder genes,
b) comparing the levels of the gene panel measured in a) to a reference level,
c) identifying the patient as more likely to respond to the therapy comprising an LSD1 inhibitor when the levels of the responder genes of the gene panel measured in a) in the sample from the patient are above the reference level, and/or when the levels of the non-responder genes of the gene panel measured in a) in the sample from the patient are below the reference level, and
d) administering an effective amount of LSD1 inhibitor.

One embodiment of the invention provides an in vitro method of identifying a patient having a neoplastic disease as likely to respond to a therapy comprising an LSD1 inhibitor, the method comprising
a) measuring in a sample from the patient the levels of a gene panel, wherein the gene panel comprises one or more genes selected from responder genes and non-responder genes,
b) calculating a signature score from the measured levels of the gene panel,
c) comparing the signature score calculated to a threshold level,
d) identifying the patient as more likely to respond to the therapy comprising an LSD1 inhibitor when the signature score is above the threshold level, and
e) administering an effective amount of LSD1 inhibitor.

Another embodiment of the invention provides an in vitro method of monitoring efficacy of therapy comprising an LSD1 inhibitor in patient having a neoplastic disease, the method comprising
a) measuring in a sample from the patient prior to start of the therapy the levels of a gene panel, wherein the gene panel comprises one or more genes selected from responder genes and non-responder genes,
b) using the levels of the gene panel measured in a) to calculate the patient's signature score prior to start of the therapy,
c) measuring in a sample from the patient after start of the therapy the levels of the gene panel,
d) using the levels of the gene panel measured in c) to calculate the patient's signature score after start of the therapy,
e) comparing the patient's signature score obtained in d) after start of the therapy with the signature score obtained in b) prior to start of the therapy, and
f) identifying the patient as responding to the therapy when the signature score obtained in d) after start of the therapy are higher than the signature score obtained in b) prior to start of the therapy.

In this application, the term "readout levels" denotes a value which can be in any form of mRNA expression measurement, such as for example expression levels derived from RNA-sequencing such as normalized read counts and RPKM (Reads per Kilobase of Million mapped reads); RT-qPCR; or microarrays.

In this application, the term "normalized read count" denotes the read count which is obtained directly from a RNA-sequencing experiment and which is normalized to make it comparable across experiments.

In this application, the term "normalized expression level" denotes a value which is obtained in a particular kind of expression measurement and which is normalized to make it comparable across experiments (e.g. normalized expression from microarrays, normalized expression from RNA-sequencing).

In one aspect of the invention, the normalized expression level is the normalized read count.

In one aspect of the invention, the levels measured are mRNA expression levels.

In one aspect of the invention, the levels measured are mRNA expression levels derived from RNA-sequencing, RT-qPCR or microarrays.

In one aspect of the invention, the reference level is a standard value from a patient with the same neoplastic disease.

In another embodiment, the reference level is median mRNA expression measured in a population of patients with the same neoplastic disease.

In one aspect of the invention, the reference level for certain genes of the gene panel are as follows (indicated as normalized read counts): ASCL1 (4515.83); DDC (2005.02); GRP (426.01); HOXA10 (10.04).

The reference levels reported above were obtained by selecting the lower normalized read count for the corresponding gene among two small cell lung cancer cell lines $C_S$ and $C_R$, wherein $C_S$ is the sensitive cell line with the lowest expression of the selected gene, and $C_R$ is the resistant cell line with the highest expression of the selected gene.

A signature score as used herein is a gene-based algorithm-derived score (a multi-gene signature) composed of values indicative for up-regulations of responder genes and for down-regulation or copy number variation of non-responder genes.

A signature score larger than a threshold level predicts response to therapy comprising an LSD1 inhibitor. The higher the threshold level for predicting response is selected for the signature score, the higher the specificity obtained. The lower the threshold level for predicting response is selected for the signature score, the higher the sensitivity obtained.

In one embodiment of the invention, the threshold level corresponds to a Signature Score 1 of 0.4 to 0.6, particularly 0.5±20%, most particularly 0.5, wherein the signature score is obtained by partial least square (PLS) analysis using the second principal component:

Signature Score 1 = 0.0900693 +

(Normalized expression level of ASCL1) × 0.00000211296 +

(Normalized expression level of DDC) × 0.000000536658 +

(Normalized expression level of GRP) × 0.00000297345 +

(Normalized expression level of HOXA10) × 0.000234721 −

(Copy number variation of MYC) × 0.0537056.

In one embodiment of the invention, the threshold level corresponds to a Signature Score 2 of 0.4 to 0.6, particularly 0.5±20%, most particularly 0.5, wherein the signature score is obtained by partial least square (PLS) analysis using the first principal component:

Signature Score 2 = 0.483918 +

(Normalized expression level of ASCL1) × 0.00000188066 +

(Normalized expression level of DDC) × 0.00000188066 +

(Normalized expression level of GRP) × 0.00000352033 −

(Copy number variation of MYC) × 0.0407898.

In one embodiment of the invention, the threshold level corresponds to a Signature Score 3 of 0.4 to 0.6, particularly 0.5±20%, most particularly 0.5, wherein the signature score is obtained by partial least square (PLS) analysis using the first principal component:

Signature Score 3 = 0.393569 +

(Normalized expression level of ASCL1) × 0.00000182731 +

(Normalized expression level of DDC) × 0.00000189664 +

(Normalized expression level of GRP) × 0.00000342046.

A signature score above the threshold level indicates a high likelihood of response to treatment with an LSD1 inhibitor, whereas a signature score below said level indicates a lower likelihood to respond to such treatment. A higher score is associated with higher mRNA expression of ASCL1, DDC, GRP and HOXA10, and with lower copy number variations in MYC.

In one embodiment of the invention, the reference level is the threshold level of a signature score.

In one embodiment of the invention, the signature score to predict response to therapy comprising an LSD1 inhibitor may be obtained by performing the following steps:

a. Select a gene panel which comprises m genes, wherein m is an integer greater than 1, selected among the genes disclosed in Table 9, and optionally HOXA10 and MYC.

b. Select a set of one or more sensitive and a set of one or more resistant cancer cell lines, particularly originating from neuroendocrine tumors such as small cell lung cancer (SCLC), as for example described in Table 6. Alternatively select a set of one or more classic and set of one or more variant small cell lung cancer cell lines.

c. Generate an n×m matrix, wherein m is as defined above and n is the total number of small cell lung cancer cell lines selected. The matrix contains expression levels of the selected genes (and/or copy number variations in case of the MYC). Gene expression levels may be reported as RPKM or as normalized read counts.

d. Generate a response vector of size n, which describes each cell line as being sensitive ("S") or resistant ("R"), as defined in Table 6. Alternatively, this vector may describe each cell line as being of "classic" ("C") or "variant" ("V") subtype.

e. Apply a machine learning algorithm for classification of the matrix described above in point c. Examples of such machine learning algorithms include, but are not limited to, decision trees, support-vector machines, neural networks, nearest neighbor analysis, naïve Bayes, random forest, partial least square, etc.

f. Perform appropriate cross-validation using either cell lines included in the analysis and/or cell lines not included in the analysis to optimize the model's predictive power.

g. Select a function f(x), as appropriate for the machine learning algorithm selected, to obtain a signature score y (y=f(x)). This function f(x) comprises a set of coefficients a1 ... ap calculated by the machine learning algorithm (where p is the number of coefficients selected by a given algorithm) and gene expression levels (x1 ... xm) of the genes selected.

h. Select a threshold, as proposed by the machine learning method, to determine whether the signature score predicts sensitivity or resistance to an LSD1 inhibition therapy.

In a particular embodiment of the invention the gene panel comprises one or more genes selected from the group of ASCL1, MYC, HOXA10, DDC, GRP, NCAM1, NCAM2, NEUROD1, KRT8, ENO2, AVP, OXT, SYP, CHGA, CHGB, SOX21 and BCL2.

In a particular embodiment of the invention the gene panel comprises one or more genes selected from the group of ASCL1, MYC, HOXA10, DDC, GRP, NCAM1, NCAM2, NEUROD1, SOX21 and BCL2.

In a particular embodiment of the invention the gene panel comprises two, three, four or five genes selected from the group of ASCL1, MYC, HOXA10, DDC, GRP, NCAM1, NCAM2, NEUROD1, SOX21 and BCL2.

In a particular embodiment of the invention the gene panel comprises one or more genes selected from the group of ASCL1, MYC, HOXA10, DDC and GRP.

In a particular embodiment of the invention the gene panel comprises two, three, four or five genes selected from the group of ASCL1, MYC, HOXA10, DDC and GRP.

In a particular embodiment of the invention the gene panel comprises one or more genes selected from the group of ASCL1, MYC and HOXA10.

In a particular embodiment of the invention the gene panel comprises the ASCL1 gene.

In a particular embodiment of the invention the gene panel comprises the MYC gene.

In a particular embodiment of the invention the gene panel comprises the HOXA10 gene.

In a particular embodiment of the invention the gene panel comprises the DDC gene.

In a particular embodiment of the invention the gene panel comprises the GRP gene.

In a particular embodiment of the invention the gene panel consists of one, two, three, four or five genes.

In a particular embodiment of the invention the gene panel consists of two, three or four genes.

In a particular embodiment of the invention the responder genes are selected from the group of ASCL1, HOXA10, DDC, GRP, NCAM1, NCAM2, NEUROD1, KTR8, ENO2, AVP, OXT, SYP, CHGA, CHGB, SOX21 and BCL2.

In a particular embodiment of the invention the non-responder genes are selected from MYC.

EXAMPLES

Figure 1A:
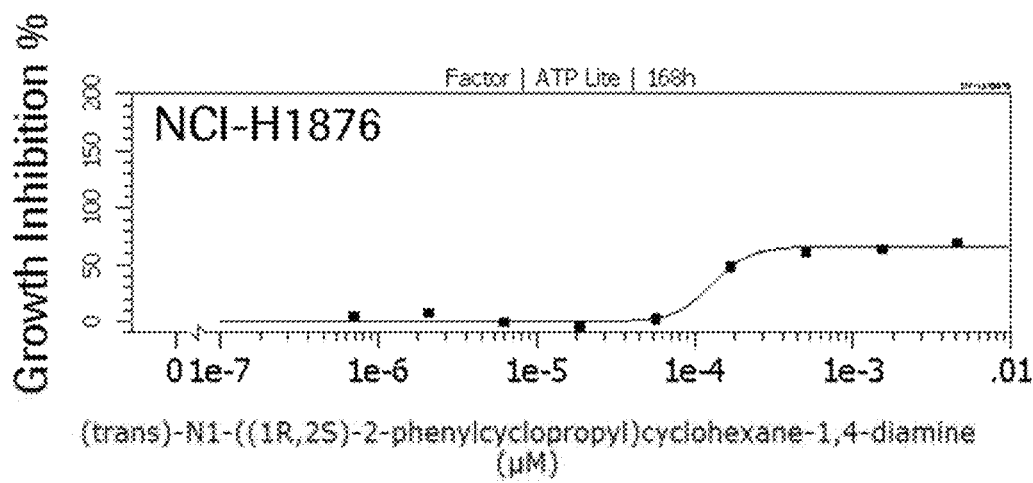
FIG. 1A and FIG. 1B: In vitro differential activity of LSD1 inhibitors (i.e. (trans)-N1-((1R,2S)-2-phenylcyclopropyl)cyclohexane-1,4-diamine) in a panel of SCLC cell lines treated for 7 days. "Classic" neuroendocrine cell lines such as NCI-H1876 (FIG. 1A) and NCI-H510 (FIG. 1B) maintained a high level of sensitivity.

The following examples 1 to 9 are provided for illustration of the invention. They should not be considered as limiting the scope of the invention, but merely as being representative thereof.

Methods

Expression Data

Expression data were obtained from whole transcriptomic RNA sequencing (RNA-seq) by Illumina, Inc. (San Diego, Calif.). The Illumina HiSeq machine generates raw base calls in reads of 50 or 100 bp length, which are subjected to several data analysis steps. The RNA-seq is conducted at 40 to 50 million reads per sample. This number provides relatively high sensitivity to detect low-expressed genes while allowing for cost-effective multiplexing of samples. RNA is prepared by standard kits and RNA libraries by polyA TruSeq Illumina kits. 100 ng of mRNA per cell line is used for each RNA-seq reaction. A number of quality control procedures are applied to the RNA-seq data for each sample. The Illumina HiSeq software reports the total number of clusters (DNA fragments) loaded in each lane, percent passing sequencing quality filters (which identifies errors due to overloading and sequencing chemistry), a phred quality score for each base of each sequence read, overall average phred scores for each sequencing cycle, and overall percent error (based on alignment to the reference genome). For each RNA-seq sample, the percentage of reads that contain mitochondrial and ribosomal RNA is calculated. The FASTQC package is used to provide additional QC metrics (base distribution, sequence duplication, overrepresented sequences, and enriched kmers) and a graphical summary. Raw reads were aligned against the human genome (hg19) using GSNAP and recommended options for RNASeq data. In addition to the genome sequence, GSNAP is given a database of human splice junctions and transcripts based on Ensembl v73. Resulting SAM files are then converted to sorted BAM files using Samtools. Gene expression values are calculated both as RPKM values following (Mortazavi et al.[107]) and as read counts. Normalized read counts were obtained using the R package DESeq2.

Copy Number Variations (CNV)

To obtain copy number variation data genomic DNA were extracted and array CGH analysis were performed by Roche NimbleGen (Madison, Wis.) using their standard protocols. Normalized signal intensities and copy number changes were obtained using the segMNT algorithm. CGH microarrays contain isothermal, 45- to 85-mer oligonucleotide probes that are synthesized directly on a silica surface using light-directed photochemistry (Selzer et al.[108]). The genomic DNA samples are randomly fragmented into lower molecular weight species and differentially labeled with fluorescent dyes.

Principal Component Analysis

Principal component analysis was carried out with Simca v 14 (Umetrics AB, Umeå, Sweden).

Differential Gene Expression Analysis

Differential gene expression analysis used to generate data in Table 9 was carried out with the R package DESeq2 starting from raw read counts for 19 cell lines.

Heat Maps of Cell Lines

Heat maps of cell lines (as in FIG. 4 and FIG. 5) were generated using GenePattern v 3.9.4 (Reich M. et al.[109]) to visualize color-coded gene expression levels. GenePattern takes in input the logarithm of normalized read counts (as reported in Table 10) plus one and applies a row-based normalization which consists of calculating z-scores for all expression levels of a given gene across the cell lines tested. A z-score of 0 corresponds to the mean of a distribution, and positive or negative value represent normalized gene expression levels above or below the mean, respectively. The color mapping capped the z-score range from −1.5 to +1.5, that is, z-scores above +1.5 are displayed in black and z-scores below −1.5 are in white. Intermediate values are displayed in different shades of gray. Gene Pattern performs hierarchical clustering to group and sort cell lines based on their gene expression profile.

Example 1—Differential Activity of LSD1 Inhibitors in SCLC Cell Lines

Figure 1B:
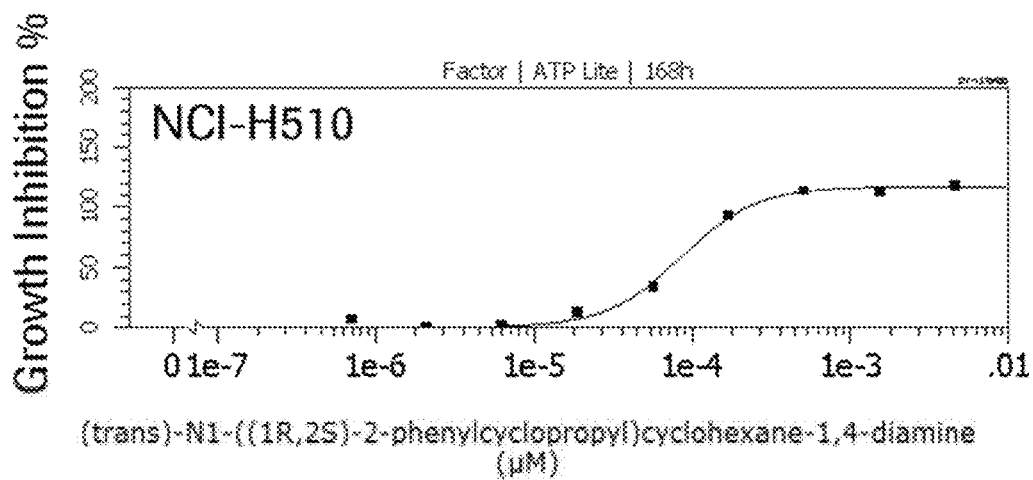

The differential activity of (trans)-N1-((1R,2S)-2-phenylcyclopropyl)cyclohexane-1,4-diamine in SCLC Cell Lines is presented in FIGS. 1A-1B. The activity of (trans)-N1-((1R,2S)-2-phenylcyclopropyl)cyclohexane-1,4-diamine was assessed in vitro in a panel of SCLC cell lines treated for 7 days. Cell lines characterized as "classic" neuroendocrine lineages, such as NCI-H1876 (FIG. 1A) and NCI-H510 (FIG. 1B), maintained a high level of sensitivity to (trans)-N1-((1R,2S)-2-phenylcyclopropyl)cyclohexane-1,4-diamine.

The compound potency determination was performed by culturing small cell lung cancer cell lines for 7 days at 37 degrees C. at 5% $CO_2$ in humidified incubators in the presence of 15-serially dilutions (trans)-N1-((1R,2S)-2-phenylcyclopropyl)cyclohexane-1,4-diamine at the indicated concentration. Each of the cell lines was propagated and tested in distinct optimized media as recommended by ATCC or cell line source.

Cells were thawed from a liquid nitrogen preserved state. Once cells have been expanded and divided at their expected doubling times, screening was started. Cells were seeded in growth media in black 384-well tissue culture treated plates at 500 cells per well (except where noted in Analyzer). Cells were equilibrated in assay plates via centrifugation and placed in incubators attached to the Dosing Modules at 37° C. for twenty-four hours before treatment. At the time of treatment, a set of assay plates (which did not receive treatment) were collected and ATP levels were measured by adding ATPLite (Perkin Elmer). These Tzero (T0) plates were read using ultra-sensitive luminescence on Envision Plate Readers. Treated assay plates were incubated with (trans)-N1-((1R,2S)-2-phenylcyclopropyl)cyclohexane-1,4-diamine for one-hundred and sixty-eight hours. After one-hundred and sixty-eight hours, plates were developed for endpoint analysis using ATPLite. All data points were collected via automated processes; quality controlled; and analyzed using Horizon CombinatoRx proprietary software. Assay plates were accepted if they passed the following quality control standards: relative luciferase values were consistent throughout the entire experiment, Z-factor scores were greater than 0.6, untreated/vehicle controls behaved consistently on the plate.

Horizon Discovery utilizes Growth Inhibition (GI) as a measure of cell viability. The cell viability of vehicle was measured at the time of dosing (T0) and after one hundred and sixty-eight hours (T168). A GI reading of 0% represents no growth inhibition—cells treated with (trans)-N1-((1R, 2S)-2-phenylcyclopropyl)cyclohexane-1,4-diamine and T168 vehicle signals were matched. A GI 100% represents complete growth inhibition—cells treated by compound and T0 vehicle signals were matched. Cell numbers have not increased during the treatment period in wells with GI 100% and may suggest a cytostatic effect for compounds reaching a plateau at this effect level. A GI 200% represents complete death of all cells in the culture well. Compounds reaching an activity plateau of GI 200% were considered cytotoxic. Horizon CombinatoRx calculates GI by applying the following test and equation:

$$\text{If} < V_0 : 100 * \left(1 - \frac{T - V_0}{V_0}\right)$$

$$\text{If} \geq V_0 : 100 * \left(1 - \frac{T - V_0}{V - V_0}\right)$$

where T is the signal measure for a test article, V is the vehicle-treated control measure, and Vo is the vehicle control measure at time zero. This formula was derived from the Growth Inhibition calculation used in the National Cancer Institute's NCI-60 high throughput screen.

Example 2—Synergistic Effects of LSD1 Inhibitors Combined with Other Active Pharmaceutical Ingredients Table 4 provides a heat map of synergy scores, the values indicating the strength of the synergistic effects. Synergy scores >6.4 were considered significant and warranted further validations. Cell lines that exhibited particular single agent response to (trans)-N1-((1R,2S)-2-phenylcyclopropyl)cyclohexane-1,4-diamine (NCI-H187, NCI-H1417, NCI-H1876, NCI-H510) were sensitized to the effects of a broad range of drug classes including HDAC and BET inhibitors, DNA alkylating agents, topoisomerase inhibitors, anti-mitotic agents, Aurora kinase inhibitors, BCL2 family inhibitors and Chk inhibitors. Similar leves of synergy were not uniformly observed in cell lines that were insensitive to (trans)-N1-((1R,2S)-2-phenylcyclopropyl)cyclohexane-1,4-diamine (NSCLC cell lines and SCLC cell line NCI-H1048, NCI-H446 and SBC-5). These data suggest the LSD1 inhibition may broadly sensitize SCLC cell lines to intervention by chemotherapeutics and targeted therapies.

Cells were thawed from a liquid nitrogen preserved state and expanded until they reached their expected doubling times. Each of the cell lines was propagated and tested in distinct optimized media as recommended by ATCC or cell line source.

Cells were seeded in 384-well assay plates at assigned densities (determined in the optimization phase). Cells were then equilibrated via centrifugation in incubators attached to the Dosing Modules for 24 hours before (trans)-N1-((1R,2S)-2-phenylcyclopropyl)cyclohexane-1,4-diamine pretreatment. Assay plates were then treated with the assigned concentrations of (trans)-N1-((1R,2S)-2-phenylcyclopropyl)cyclohexane-1,4-diamine (determined in the optimization phase).

At the time of (trans)-N1-((1R,2S)-2-phenylcyclopropyl)cyclohexane-1,4-diamine treatment, a set of assay plates (which do not compound treatment) were collected and ATP levels measured by adding ATPLite (Perkin Elmer). These Tzero (T0) plates were read on Envision Plate Readers to measure luminescence. Treated assay plates were incubated with (trans)-N1-((1R,2S)-2-phenylcyclopropyl)cyclohexane-1,4-diamine for 96 hours before treatment with the second compound. After this time, assay plates were then treated with 8 point serial dilutions of enhancer compound in a 9×9 extended matrix and harvested after another 72 hours incubation. After a total of 168 hours from the initial (trans)-N1-((1R,2S)-2-phenylcyclopropyl)cyclohexane-1,4-diamine treatment time, plates were developed for endpoint analysis using ATPLite. All data points were collected via automated processes; quality controlled; and analyzed using Horizon CombinatoRx proprietary software. Assay plates were accepted if they passed the following quality control standards: relative luciferase values were consistent throughout the entire experiment, Z-factor scores were greater than 0.6, untreated/vehicle controls behaved consistently on the plate.

Horizon Discovery utilizes Growth Inhibition (GI) as a measure of cell viability. The cell viability of vehicle is measured at the time of dosing (T0) and after one hundred and sixty-eight hours (T168). A GI reading of 0% represents no growth inhibition—cells treated with compound and T168 vehicle signals are matched. A GI 100% represents complete growth inhibition—cells treated by compound and T0 vehicle signals are matched. Cell numbers have not increased during the treatment period in wells with GI 100% and may suggest a cytostatic effect for compounds reaching a plateau at this effect level. A GI 200% represents complete death of all cells in the culture well. Compounds reaching an activity plateau of GI 200% are considered cytotoxic. Horizon CombinatoRx calculates GI by applying the following test and equation:

$$\text{If} < V_0 : 100 * \left(1 - \frac{T - V_0}{V_0}\right)$$

$$\text{If} \geq V_0 : 100 * \left(1 - \frac{T - V_0}{V - V_0}\right)$$

where T is the signal measure for a test article, V is the vehicle-treated control measure, and Vo is the vehicle control measure at time zero. This formula is derived from the Growth Inhibition calculation used in the National Cancer Institute's NCI-60 high throughput screen.

Loewe additivity model is dose-based and applies only to the activity levels achieved by the single agents. Loewe Volume is used to assess the overall magnitude of the combination interaction in excess of the Loewe additivity model. Loewe Volume is particularly useful when distinguishing synergistic increases in a phenotypic activity (positive Loewe Volume) versus synergistic antagonisms (negative Loewe Volume). When antagonisms are observed, as in the current dataset, the Loewe Volume should be assessed to examine if there is any correlation between antagonism and a particular drug target-activity or cellular genotype. This model defines additivity as a non-synergistic combination interaction where the combination dose matrix surface should be indistinguishable from either drug crossed with itself. The calculation for additivity is:

$$I_{Loewe} \text{ that satisfies } (X/X_I) + (Y/Y_I) = 1$$

where $X_I$ and $Y_I$ are the single agent effective concentrations for the observed combination effect I. For example, if 50% inhibition is achieved separately by 1 mM of drug A or 1 mM of drug B, a combination of 0.5 mM of A and 0.5 mM of B should also inhibit by 50%.

To measure combination effects in excess of Loewe additivity, the Horizon Discovery platform was utilized. This method devised a scalar measure to characterize the strength of synergistic interaction termed the Synergy Score. The Synergy Score is calculated as:

$$\text{Synergy Score} = \log f_X \log f_Y \Sigma \max(0, I_{data})(I_{data} - I_{Loewe})$$

The fractional inhibition for each component agent and combination point in the matrix is calculated relative to the median of all vehicle-treated control wells. The Synergy Score equation integrates the experimentally-observed activity volume at each point in the matrix in excess of a model surface numerically derived from the activity of the component agents using the Loewe model for additivity. Additional terms in the Synergy Score equation (above) are used to normalize for various dilution factors used for individual agents and to allow for comparison of synergy scores across an entire experiment.

Activity over Loewe additivity is most easily calculated using a simple volume score, where $V_{Loewe} = \log f_X \log f_Y \Sigma (I_{data} - I_{Loewe})$, summed over all non-single agent concentration pairs and where $\log f_{X,Y}$ are the natural logarithm of the dilution factors used for each single agent. This effectively calculates a volume between the measured and Loewe additive response surfaces, corrected for varying dilution factors. This volume score emphasizes the overall synergistic or antagonistic effect of the combination, thus minimizing the effects of outlying data spikes and identifying combinations with a robust synergy across a wide range of concentrations and at high effect levels. $V_{Loewe}$ is positive for mostly synergistic combinations and negative for antagonism. The uncertainty $\sigma_V$ can be calculated based on the measured errors $\sigma_I$ and standard error propagation.

"Synergy Score" $S = f_{cov} \ln f^X \ln f^Y \Sigma \max(0, I^{data}) \max(0, I^{data} - I^{Loewe})$, which is a positive-gated, inhibition-weighted volume over Loewe additivity. This provides an additional prioritization favoring combinations whose synergy occurs at high effect levels, ignoring antagonistic portions of the response surface. Here $f^{X,Y}$ are the dilution factors used for each single agent and the coverage factor $f^{cov}$ accounts for missing data, scaling the score up by the ratio of total/tested combination dose matrix points. S is always positive, and its uncertainty as can be calculated based on the measured errors $\sigma_I$ and standard error propagation. An alternative to the synergy score is the "Hit Score" $H=f^{COV} \log f^X \log f^Y \Sigma \max(0,I_{data}) \max(0,I^{data}-I^{HSA})$, which refers to the HSA model. The key distinctions between S and H lie in the different underlying models and also in how the single agents are used in the model calculations. In the Chalice Analyzer, the HSA model is calculated directly from the single agent responses at corresponding concentrations, while the Loewe additive model is derived from the sigmoidal fits to the single agent response curves.

To prioritize hits, distributions of a score (S or H) and its error can be used to define an appropriate selection cutoff. For example, combinations with S>3σs are "individually significant" at ~99% confidence, assuming normal errors. To estimate systematic experimental errors that are not tested by replicate plates, the distribution of synergy scores for any drug-with-itself combinations acquired during the experiment can be used to determine a plausible range for non-detections. Alternatively, the score distribution for the whole experiment can be used to identify outliers at a chosen confidence level.

Example 3—In Vitro Synergistic Effects for SCLC of LSD1 Inhibitors Combined with Other Active Pharmaceutical Ingredients Table 5 provides a heat map of synergy scores, the values indicating the strength of the synergistic effects. Synergy scores >6.4 were considered significant and warranted further validations. A select panel of drug classes were prioritized for further evaluation in an expanded panel of SCLC cell lines based upon the level of synergy observed and potential clinical use of the compounds in a therapeutic regimen in SCLC. Targeted therapies and chemical probes that inhibited the epigenetic regulator BET (particularly Brd4) ((+)-JQ1, CPI-203, MS 436, GSK1324726A, GSK1210151A and OTX015) and anti-apoptotic regulator BCL2 (Obatoclax, ABT-199, ABT-737, and TW-37) were highly synergistic with LSD1 inhibition. Synergy was also observed with other epigenetic regulators, EZH2 (e.g. CPI-169, EPZ005687, EPZ-6438, GSK126, GSK343) and DOT1L (e.g. EPZ-5676, SGC 0946), albeit at a low level compared to BET (particularly BRD4) and BCL2 inhibitors.

Inhibitors of the Notch, Hedgehog or Smoothened pathway were not synergistic with (trans)-N1-((1R,2S)-2-phenylcyclopropyl)cyclohexane-1,4-diamine treatment, indicating that LSD1 inhibition sensitizes cell lines to select compound and drug classes that include HDAC and BET inhibitors, DNA alkylating agents, topoisomerase inhibitors, anti-mitotic agents, Aurora kinase inhibitors, BCL2 family inhibitors, EZH2, DOT1L and Chk inhibitors.

Cells were treated and data analyzed as described in Example 2 above.

TABLE 4

Synergistic effects of combinations of (trans)-N1-((1R,2S)-2-phenylcyclopropyl)cyclohexane-1,4-diamine with a panel of suitable active pharmaceutical ingredients (API).

| | Synergy Scores in NSCLC | | | Synergy Scores in SCLC | | | | | | |
|---|---|---|---|---|---|---|---|---|---|---|
| 2nd API: | CAL-12T | A549 | NCI-H441 | NCI-H187 | NCI-H1417 | NCI-H1876 | NCI-H510 | NCI-H1048 | NCI-H446 | SBC-5 |
| (+)-JQ1 | 0.51 | 0.07 | 0.12 | 11.29 | 39.59 | 18.65 | 11.88 | 0.68 | 1.74 | 0.15 |
| ABT-263 | 0.01 | 0.89 | 0.75 | 14.31 | 19.10 | 23.63 | 18.16 | 14.92 | 0.29 | 3.35 |
| ABT-888 | 0.22 | 0.02 | 0.04 | 2.26 | 3.26 | 8.62 | 4.10 | 0.40 | 0.05 | 0.27 |
| Belinostat | 0.42 | 0.52 | 0.66 | 14.35 | 19.12 | 9.05 | 15.72 | 1.61 | 3.21 | 1.84 |
| Benda-mustine | 0.10 | 0.02 | 0.01 | 8.19 | 5.20 | 12.38 | 1.12 | 2.01 | 0.10 | 0.37 |
| BGJ398 | 0.49 | 0.16 | 0.17 | 9.26 | 9.66 | 19.85 | 4.42 | 9.55 | 17.33 | 0.69 |
| Carbo-platin | 0.06 | 0.03 | 1.27 | 7.49 | 10.45 | 10.90 | 9.96 | 1.47 | 1.58 | 0.22 |
| CGK 733 | 0.39 | 3.07 | 0.27 | 3.35 | 0.91 | 4.59 | 3.03 | 1.21 | 5.16 | 0.78 |
| Cisplatin | 0.85 | 0.04 | 1.80 | 4.91 | 15.96 | 5.34 | 9.89 | 3.72 | 1.56 | 0.48 |
| Docetaxel | 1.42 | 1.21 | 1.82 | 13.67 | 11.72 | 19.92 | 31.60 | 0.50 | 3.33 | 0.88 |
| Doxo-rubicin | 0.76 | 0.45 | 6.86 | 6.85 | 33.43 | 3.74 | 15.96 | 3.13 | 4.93 | 1.20 |
| Erlotinib | 0.43 | 0.18 | 0.70 | 3.17 | 2.87 | 5.21 | 3.29 | 0.50 | 1.99 | 0.32 |
| Etoposide | 0.15 | 0.00 | 5.83 | 8.28 | 13.22 | 11.17 | 11.55 | 1.04 | 0.12 | 0.54 |
| Fluorouracil | 0.07 | 0.00 | 0.68 | 1.97 | 1.63 | 4.91 | 0.62 | 0.80 | 0.09 | 0.42 |
| Gem-citabine | 0.58 | 0.93 | 6.78 | 19.43 | 15.18 | 2.74 | 23.37 | 1.11 | 1.01 | 0.33 |
| GSK-J1 | 0.01 | 0.07 | 0.09 | 2.14 | 2.26 | 10.21 | 3.80 | 0.23 | 0.03 | 0.85 |
| Irinotecan | 0.14 | 0.02 | 3.45 | 13.74 | 21.62 | 8.75 | 17.17 | 2.00 | 1.16 | 0.48 |
| Lapatinib | 1.23 | 0.00 | 0.36 | 1.23 | 7.00 | 5.69 | 20.64 | 0.75 | 20.44 | 0.03 |
| LY-2603618 | 1.46 | 0.20 | 2.22 | 6.47 | 1.05 | 11.98 | 14.09 | 1.47 | 0.37 | 0.87 |
| Menadione | 0.01 | 0.06 | 0.02 | 3.89 | 4.18 | 8.81 | 3.63 | 0.45 | 0.06 | 0.52 |
| Metho-trexate | 0.25 | 1.95 | 0.29 | 1.45 | 1.82 | 4.20 | 1.75 | 0.62 | 0.74 | 0.34 |
| MLN8237 | 0.76 | 0.08 | 0.81 | 7.60 | 9.15 | 23.31 | 28.91 | 1.02 | 1.16 | 0.51 |
| Nutlin-3A | 0.11 | 0.04 | 0.36 | 1.56 | 2.56 | 7.24 | 1.63 | 0.29 | 0.36 | 0.48 |
| Paclitaxel | 0.83 | 1.11 | 1.33 | 12.68 | 14.10 | 20.99 | 28.03 | 2.26 | 2.64 | 1.83 |
| Pano-binostat | 1.11 | 1.34 | 0.45 | 10.41 | 17.19 | 2.60 | 12.47 | 0.58 | 15.30 | 1.13 |
| Peme-trexed | 2.12 | 0.01 | 2.76 | 4.10 | 2.54 | 4.27 | 0.86 | 0.20 | 0.18 | 0.11 |
| PF-04217903 | 0.15 | 0.07 | 0.16 | 0.99 | 0.81 | 6.68 | 1.11 | 0.56 | 0.01 | 0.49 |
| Temozo-lomide | 0.04 | 0.00 | 4.12 | 2.52 | 21.79 | 8.49 | 5.43 | 0.81 | 0.37 | 0.10 |

TABLE 4-continued

Synergistic effects of combinations of (trans)-N1-((1R,2S)-2-phenylcyclopropyl)cyclohexane-1,4-diamine with a panel of suitable active pharmaceutical ingredients (API).

| | Synergy Scores in NSCLC | | | Synergy Scores in SCLC | | | | | | |
|---|---|---|---|---|---|---|---|---|---|---|
| 2nd API: | CAL-12T | A549 | NCI-H441 | NCI-H187 | NCI-H1417 | NCI-H1876 | NCI-H510 | NCI-H1048 | NCI-H446 | SBC-5 |
| Topotecan | 0.08 | 1.92 | 1.98 | 11.49 | 2.24 | 6.23 | 23.12 | 3.73 | 6.87 | 0.20 |
| Vincristine | 0.49 | 1.23 | 0.04 | 18.07 | 27.52 | 7.80 | 10.01 | 0.08 | 2.31 | 0.15 |

TABLE 5 in vitro Synergistic Effects in SCLC cell lines of combinations of (trans)-N1-((1R,2S)-2-phenylcyclopropyl)cyclohexane-1,4-diamine with a panel of suitable active pharmaceutical ingredients (API).

| | Synergy Scores of SCLC cell lines | | | | | | | | | |
|---|---|---|---|---|---|---|---|---|---|---|
| 2nd API | NCI-H1876 | NCI-H510 | NCI-H1417 | NCI-H187 | NCI-H2171 | NCI-H69 | SHP-77 | NCI-H526 | DMS-114 | NCI-H446 |
| (+)-JQ1 | 9.15 | 24.21 | 7.87 | 2.83 | 8.69 | 6.44 | 0.45 | 8.06 | 1.55 | 4.03 |
| ABT-199 | 4.63 | 13.46 | 11.01 | 1.95 | 0.04 | 5.07 | 0.33 | 3.47 | 0.03 | 0.07 |
| ABT-263 | 21.80 | 10.70 | 12.21 | 2.51 | 6.19 | 8.22 | 3.59 | 4.18 | 0.26 | 1.41 |
| ABT-737 | 19.84 | 11.80 | 25.26 | 4.17 | 3.15 | 4.01 | 1.88 | 11.44 | 0.42 | 1.73 |
| BMS-906024 | 0.22 | 0.00 | 0.33 | 0.45 | 0.19 | 8.46 | 0.03 | 5.80 | 0.02 | 0.12 |
| CPI-169 | 8.50 | 5.76 | 0.38 | 0.09 | 0.00 | 0.03 | 0.03 | 2.46 | 0.06 | 0.31 |
| CPI-203 | 15.25 | 25.41 | 13.47 | 1.24 | 6.83 | 8.68 | 0.37 | 11.09 | 1.58 | 0.58 |
| EPZ005687 | 4.57 | 10.77 | 0.46 | 0.10 | 0.48 | 0.80 | 0.23 | 3.66 | 0.14 | 0.35 |
| EPZ-5676 | 6.68 | 19.72 | 0.87 | 0.11 | 0.05 | 0.70 | 0.12 | 1.20 | 0.00 | 0.24 |
| EPZ-6438 | 8.18 | 9.06 | 0.31 | 0.03 | 0.01 | 0.68 | 0.02 | 1.82 | 0.04 | 0.00 |
| FLI 06 | 6.95 | 0.83 | 0.28 | 1.71 | 1.76 | 4.01 | 6.32 | 2.18 | 5.48 | 3.29 |
| GDC-0449 | 5.64 | 3.05 | 0.25 | 0.16 | 0.10 | 0.90 | 0.24 | 1.76 | 0.01 | 0.16 |
| GSK1210151A | 11.42 | 15.35 | 15.13 | 1.77 | 10.11 | 10.38 | 0.66 | 12.65 | 0.67 | 0.32 |
| GSK126 | 10.80 | 12.69 | 0.41 | 0.35 | 0.80 | 1.63 | 0.02 | 3.20 | 0.51 | 0.41 |
| GSK1324726A | 15.98 | 21.32 | 21.84 | 2.66 | 9.12 | 10.17 | 0.72 | 12.18 | 1.22 | 1.25 |
| GSK343 | 0.81 | 4.25 | 0.24 | 0.15 | 0.36 | 0.81 | 0.13 | 2.48 | 0.05 | 0.01 |
| LDE225 | 0.57 | 5.81 | 1.01 | 0.73 | 0.34 | 0.78 | 0.53 | 2.17 | 0.08 | 0.02 |
| LY-3039478 | 0.19 | 0.00 | 0.21 | 0.47 | 0.30 | 4.94 | 0.12 | 7.90 | 0.00 | 0.28 |
| MK-0752 | 0.69 | 0.71 | 0.15 | 0.32 | 0.17 | 3.88 | 0.03 | 6.03 | 0.04 | 0.43 |
| MS 436 | 5.74 | 5.52 | 12.37 | 0.06 | 1.37 | 3.82 | 0.23 | 15.84 | 0.18 | 0.42 |
| Obatoclax | 6.11 | 6.31 | 2.36 | 0.81 | 0.61 | 6.01 | 4.76 | 8.19 | 1.87 | 2.57 |
| OTX015 | 14.88 | 11.52 | 14.26 | 0.88 | 5.30 | 8.65 | 0.78 | 16.72 | 0.10 | 0.44 |
| PF-3084014 | 0.25 | 0.03 | 0.02 | 0.10 | 1.02 | 1.53 | 0.19 | 8.64 | 0.02 | 1.31 |
| SGC 0946 | 6.81 | 24.63 | 0.28 | 0.12 | 0.07 | 4.50 | 0.06 | 1.80 | 0.00 | 0.06 |
| Taladegib | 1.64 | 2.50 | 0.19 | 0.09 | 0.11 | 2.35 | 0.19 | 3.66 | 0.10 | 0.01 |
| TW-37 | 0.86 | 6.95 | 8.08 | 0.57 | 0.72 | 2.23 | 0.45 | 3.60 | 0.59 | 0.28 |

Example 4. LSD1 Inhibitors Improve Potency and Duration of SCLC-SOC In Vivo

Figure 2A:
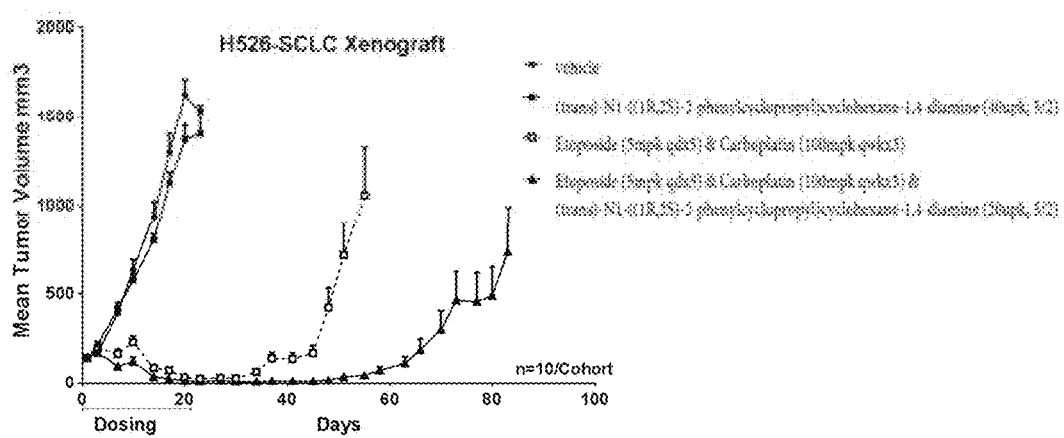
FIG. 2A and FIG. 2B: LSD1 inhibitors (i.e. (trans)-N1-((1R,2S)-2-phenylcyclopropyl)cyclohexane-1,4-diamine) improve potency and duration of SCLC standards of care (SOC) etoposide and carboplatin in vivo (FIG. 2A) as well as in vivo in mice (FIG. 2B).

In vivo, the effects of (trans)-N1-((1R,2S)-2-phenylcyclopropyl)cyclohexane-1,4-diamine treatment synergized with both etoposide and carboplatin to induce a cytotoxic response as can be seen from FIG. 2A. In the clinic the one standard of care (SOC) for SCLC is to combine etoposide and carboplatin.

Figure 2B:
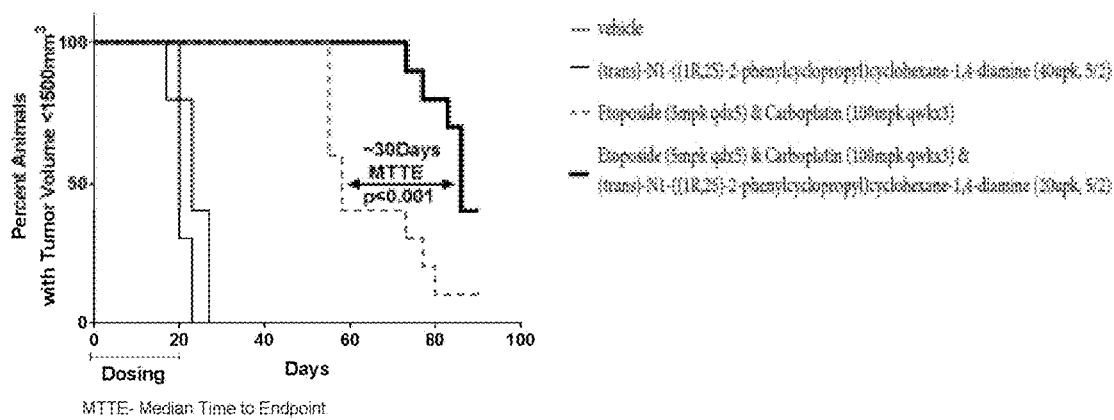

In vivo, the combination of etoposide and carboplatin promotes rapid tumor regression during the dosing period in the NCI-H526 model as can be seen from FIG. 2B. The addition of (trans)-N1-((1R,2S)-2-phenylcyclopropyl)cyclohexane-1,4-diamine to SOC improved the duration of tumor regression and significantly delayed tumor regrowth by 30 days after the suspension of dosing. Together the data suggest that LSD1 inhibition can sensitize cells to select chemotherapeutics and targeted agents in vitro and in vivo.

NCI-H526 Models:

8-12-week old nu/nu mice were injected with 1×107 H526 cells or 5×106 SHP-77 resuspended in 100 μL of 1:1 mixture of Matrigel® and PBS. Tumors were staged at 100-150 mm$^3$ animals and distributed into dosing groups. (trans)-N1-((1R,2S)-2-phenylcyclopropyl)cyclohexane-1,4-diamine was administered at a dose of 40 μg per kg (upk) five days on/two days off (5/2) for three weeks. Etoposide was administered i.p at a dose of 5 mg per kg (mpk) daily for five days (qd×5). Carboplatin was administered i.p. at a dose of 100 mpk weekly for three weeks (qwk×3). In combination with etoposide and carboplatin, (trans)-N1-((1R,2S)-2-phenylcyclopropyl)cyclohexane-1,4-diamine was administered at a dose of 20 upk five days on/two days off for three weeks. Tumor volume was measure biweekly using a digital caliber. The endpoint of the experiment was a tumor volume of 1000 mm$^3$ or 90 days, whichever came first. Statistical analysis was performed using unpaired t-test and Gehan-Breslow-Wilcoxon test.

Example 5. Cell Response to LSD1 Inhibition

The compound potency determination was performed by culturing 19 small cell lung cancer cell lines (of various tumor origins) for 4 days at 37 degrees C. at 5% $CO_2$ in humidified incubators in the presence of serially diluted (trans)-N1-((1R,2S)-2-phenylcyclopropyl)cyclohexane-1,4-diamine bis-hydrochloride.

As a positive control for cytotoxicity the Hsp90 inhibitor 17-N-allylamino-17-demethoxygeldanamycin (17-AAG, a geldanamycin analogue) was used as positive control in serial dilution. Each of the cell lines was propagated and tested in distinct optimized media as recommended by ATCC or cell line source.

Small cell lung cancer cell lines can be categorized as "classic" or "variant", based on their enzymatic activities, cellular morphologies, and growth phenotypes (Desmond et al[110]. Shoemaker R. H.[111]). Classic cells lines express elevated levels of L-dopa decarboxylase, bombesin-like immunoreactivity, neuron-specific enolase, and the brain isozyme of creatine kinase; variant cell lines continue to express neuron-specific enolase and the brain isozyme of creatine kinase, but have undetectable levels of L-dopa decarboxylase and bombesin-like immunoreactivity. Unlike classic cell lines, some variant cell lines are amplified for and have increased expression of the c-myc (MYC)oncogene.

Some cell lines exhibit features specific to both a classic and variant subtype. For example, SHP-77 has biochemical properties of classic SCLC (e.g. elevated levels of L-dopa decarboxylase and bombesin-like immunoreactivity) but the morphology of a variant. According to the literature, SHP-77 is considered classic based on its biochemical profile but variant based on its morphology and growth characteristic.

For NCI-H2029 and SBC-5 no subtype is reported in literature however their transcriptomic profile (mRNA expression levels of DDC/GRP) clearly shows their class membership which is provided in brackets in Table 6.

Depending on their responses to (trans)-N1-((1R,2S)-2-phenylcyclopropyl)cyclohexane-1,4-diamine bis-hydrochloride, cell lines are classified as either "sensitive" [S], defined as having EC50<0.05 µM, or "resistant", defined as having EC50>=0.05 µM [R].

Cell-based response to (trans)-N1-((1R,2S)-2-phenylcyclopropyl)cyclohexane-1,4-diamine bis-hydrochloride was greater in classic SCLC cell lines compared to variant SCLC cell lines (p-value 0.0055 Table 6). Out of the 19 SCLC cell lines tested, 9 out of 11 classic cell lines [C] are sensitive [S], and 7 out of 8 variant cell lines [V] are resistant [R] (Table 7).

The variant and classic subtypes predict response to an LSD1 inhibitor therapy with a sensitivity of 82% and specificity of 88%.

Higher copy number variations (CNV) in the MYC gene (Ensembl Gene ID: ENSG00000136997) are associated with small cell lung cancer of variant subtype (V) (Am J Pathol. 1988 July; 132(1): 13-17). Indeed, among the 19 cell lines here described, high copy number variations of the MYC gene (CNV>>2) were found exclusively in cell lines with a variant subtype (NCI-H2171, NCI-H446, NCI-H82, see Table 6). Furthermore, all three cell lines with high copy number variations of MYC were resistant to LSD1 inhibition, indicating that the presence of MYC amplification can predict resistance (R) to an LSD1 inhibition therapy.

Figure 3:
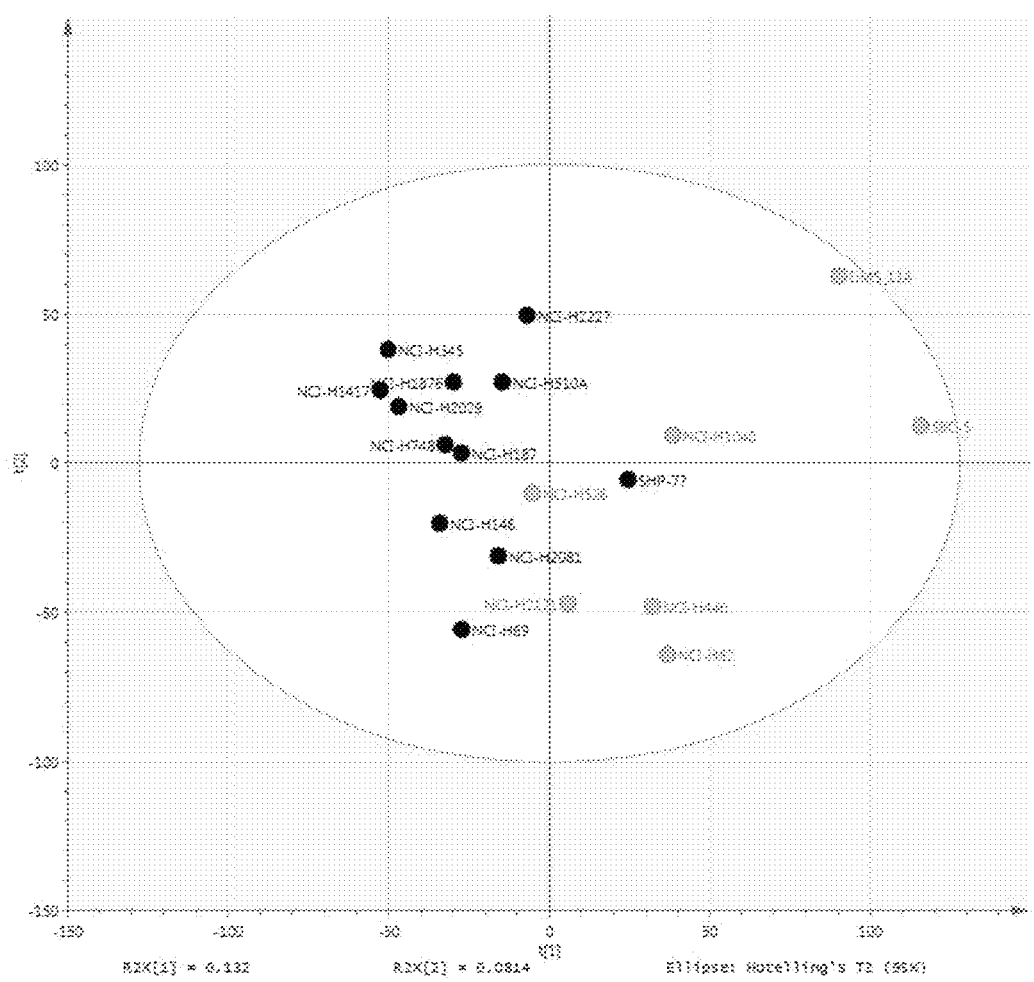
FIG. 3: Principal component analysis score plot for principal component 1 (t[1], x-axis) and principal component 2 (t[2], y-axis) separates classic cell lines (C, black) from variant cell lines (V, gray) according to Example 5.

Principal component analysis carried out from RNA-seq data for the cell lines of Table 6 surprisingly revealed that classic and variant SCLC cell lines form distinct clusters. (FIG. 3).

TABLE 6

Cell-based response to (trans)-N1-((1R,2S)-2-phenyl-cyclopropyl)cyclohexane-1,4-diamine bis-hydrochloride in classic SCLC cell lines [C] as compared to variant SCLC cell lines [V].

| Cell Line | SubType Lit. | Max. Response (%) | EC50 (µM) | Sensitivity to LSD1 inh. | MYC CNV |
|---|---|---|---|---|---|
| NCI-H1876 | C | 145 | $4.32 \times 10^{-5}$ | S | 0.81 |
| NCI-H69 | C | 44 | $5.85 \times 10^{-4}$ | S | 1.14 |
| NCI-H510A | C | 68 | $3.15 \times 10^{-4}$ | S | 2.56 |
| NCI-H146 | C | 48 | $1.00 \times 10^{-4}$ | S | 1.24 |
| NCI-H187 | C | 61 | $1.36 \times 10^{-4}$ | S | 1.12 |
| NCI-H2081 | C | 10 | $9.20 \times 10^{-4}$ | S | 2.22 |
| NCI-H345 | C | 7 | $2.75 \times 10^{-5}$ | S | 1.26 |
| NCI-H526 | V | 35 | $6.32 \times 10^{-4}$ | S | 1.07 |
| NCI-H748 | C | 13 | $3.00 \times 10^{-4}$ | S | 1.05 |
| NCI-H1417 | C | 77 | $3.02 \times 10^{-4}$ | S | NA |
| DMS-114 | V | 0 | $>5 \times 10^{-2}$ | R | 1.21 |
| NCI-H1048 | V | 27 | $>5 \times 10^{-2}$ | R | 0.98 |
| NCI-H2029 | (C) | 0 | $>5 \times 10^{-2}$ | R | 1.23 |
| NCI-H2171 | V | 0 | $>5 \times 10^{-2}$ | R | 7.46 |
| NCI-H2227 | C | 0 | $>5 \times 10^{-2}$ | R | 0.81 |
| NCI-H446 | V | 7 | $>5 \times 10^{-2}$ | R | 6.72 |
| NCI-H82 | V | 0 | $>5 \times 10^{-2}$ | R | 9.44 |
| SHP-77 | V (C) | 0 | $>5 \times 10^{-2}$ | R | 1.36 |
| SBC-5 | (V) | 23 | $>5 \times 10^{-2}$ | R | 1.21 |

TABLE 7

Contingency matrix showing the number of classic and variant cell lines that are sensitive or resistant to an LSD1 inhibition therapy.

|  | Classic [C] | Variant [V] |
|---|---|---|
| Sensitive [S] | 9 | 1 |
| Resistant [R] | 2 | 7 |

Example 6. Gene Panel to Predict Response to LSD1 Inhibition

Differential gene expression analysis between two resistant cell lines that have features of a classic subtype (SHP-77 and NCI-2029) and classic and variant cell lines which are sensitive (NCI-H1876, NCI-H69, NCI-H510A, NCI-H146, NCI-H187, NCI-H2081, NCI-H345, NCI-H526, NCI-H748) interestingly revealed that lower mRNA expression levels of HOXA10 correlate with resistance to an LSD1 inhibition therapy (Table 8). This suggests that low levels of HOXA10 mRNA may predict resistance to an LSD1 inhibition therapy even in the presence of a classic phenotype.

A predictive mRNA expression signature of response to an LSD1 inhibition therapy was defined by selecting top differentially expressed genes between classic and variant cell lines (Table 9). Based on adjusted p-values, DDC (adjusted p-value 4.37E-23), which encodes the enzyme L-dopa decarboxylase, and GRP (adjusted p-value 5.19E-14), which encodes bombesin-like immunoreactivity peptides rank as second and sixth most differentially expressed genes. The most differentially expressed gene is ASCL1 (adjusted p-value 2.6E-23). ASCL1 is a transcription factor required for proper development of pulmonary neuroendocrine cells, and is essential for the survival of a majority of lung cancers (Augustyn et al.[112]).

As discussed in Example 5 above, MYC amplification can predict resistance to LSD1 inhibition therapy.

Table 10 lists normalized read counts of DDC, GRP, and ASCL1 across the 19 cell lines of Table 6 described while Table 11 lists the corresponding z-scores.

Figure 4:
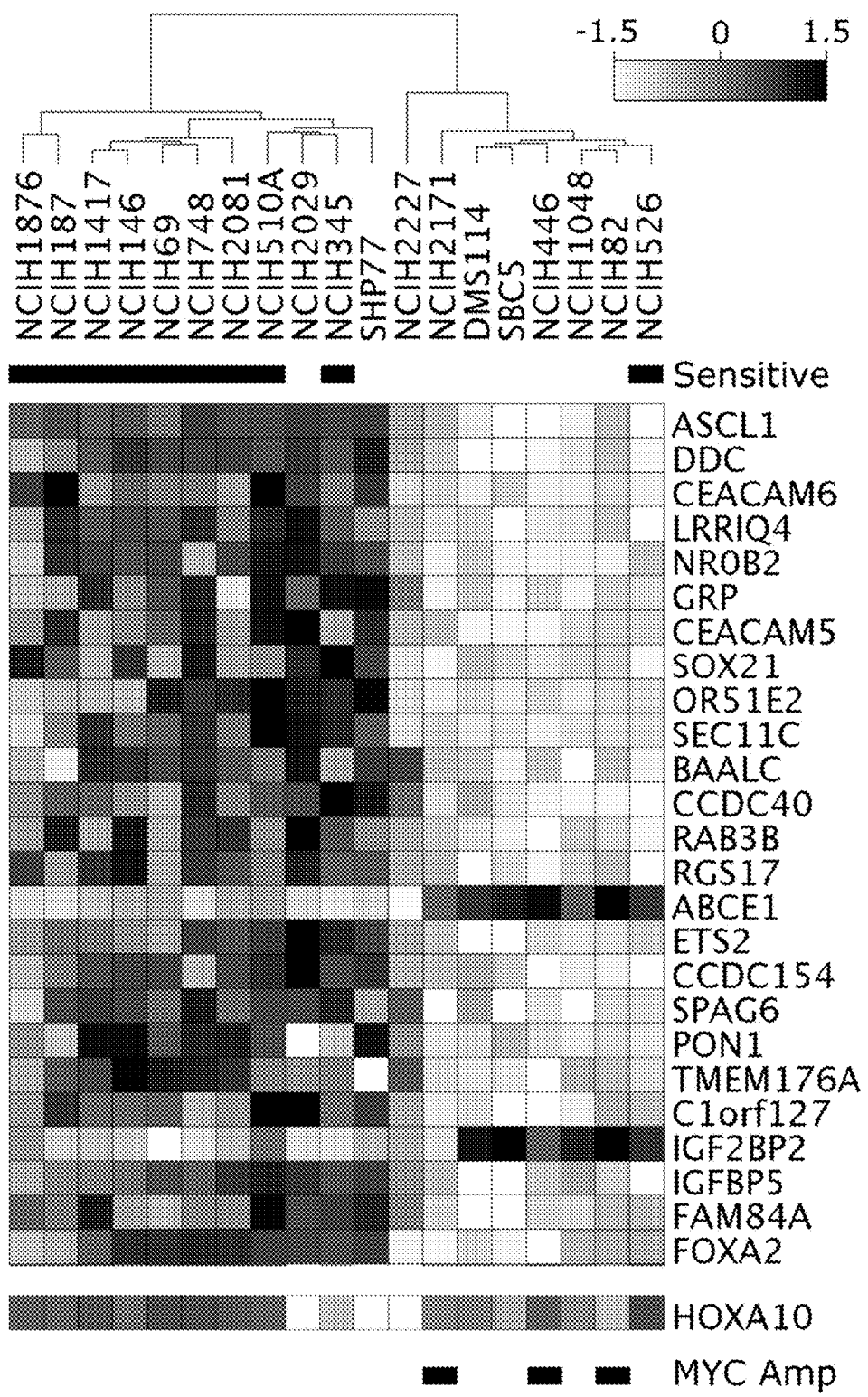
FIG. 4: Heat Map showing mRNA expression (as z-scores) for the gene panel of Example 6 comprising the genes of Table 8, Table 6 and MYC. These genes best predict response to an LSD1 inhibition therapy in the 19 cell lines of Table 6. Higher z-scores correlate with better sensitivity.

The heat map of FIG. 4 visually shows that sensitive cell lines can be distinguished from resistant cell lines based on mRNA expression levels of genes listed in Table 9, and based on expression levels of HOXA10 and copy number variations of MYC.

TABLE 8

Principal component analysis for HOXA10 carried out from RNA-seq data for selected cell lines

| Ensembl Gene ID* | Gene | baseMean | log2Fold Change | pvalue |
|---|---|---|---|---|
| ENSG00000253293 | HOXA10 | 2717.58 | 8.21 | 7.45E−023 |

(*http://www.ensembl.org/, Cunningham F. et al.[106])

TABLE 9

Genes sorted according to pvalue obtained through principal component analysis carried out from RNA-seq data for selected cell lines

| Ensembl Gene ID* | Gene | baseMean | log2Fold Change | pvalue |
|---|---|---|---|---|
| ENSG00000139352 | ASCL1 | 43665.33 | 6.82 | 2.62E−023 |
| ENSG00000132437 | DDC | 15817.8 | 6.42 | 4.37E−023 |
| ENSG00000086548 | CEACAM6 | 210.89 | 6.34 | 1.23E−017 |
| ENSG00000188306 | LRRIQ4 | 90.81 | 5.1 | 4.61E−016 |
| ENSG00000131910 | NR0B2 | 600.58 | 6.35 | 5.15E−015 |
| ENSG00000134443 | GRP | 6711.45 | 6.52 | 5.19E−014 |
| ENSG00000105388 | CEACAM5 | 1788.17 | 6.22 | 9.23E−014 |
| ENSG00000125285 | SOX21 | 523.59 | 5.88 | 2.29E−013 |
| ENSG00000167332 | OR51E2 | 3047.56 | 6.39 | 3.37E−013 |
| ENSG00000166562 | SEC11C | 36139.18 | 3.33 | 5.01E−013 |
| ENSG00000164929 | BAALC | 1833.4 | 4.33 | 1.66E−012 |
| ENSG00000141519 | CCDC40 | 2309.83 | 2.26 | 2.07E−012 |
| ENSG00000169213 | RAB3B | 28247.78 | 3.64 | 2.80E−012 |
| ENSG00000091844 | RGS17 | 2783.99 | 3.2 | 3.72E−012 |
| ENSG00000164163 | ABCE1 | 13643.12 | −1.08 | 4.99E−012 |
| ENSG00000157557 | ETS2 | 11829.42 | 3.06 | 5.19E−012 |
| ENSG00000197599 | CCDC154 | 1198.98 | 4.61 | 7.21E−012 |
| ENSG00000077327 | SPAG6 | 767.39 | 5.34 | 7.85E−012 |
| ENSG00000005421 | PON1 | 334.17 | 5.15 | 1.53E−011 |
| ENSG00000002933 | TMEM176A | 3224.04 | 5.38 | 7.65E−011 |
| ENSG00000175262 | C1orf127 | 596.15 | 5.04 | 1.19E−010 |
| ENSG00000073792 | IGF2BP2 | 2414.53 | −5.17 | 1.28E−010 |
| ENSG00000115461 | IGFBP5 | 86866.7 | 4.41 | 1.38E−010 |
| ENSG00000162981 | FAM84A | 4954.8 | 3.93 | 1.45E−010 |
| ENSG00000125798 | FOXA2 | 4530.46 | 5.12 | 1.71E−010 |

(*http://www.ensembl.org/, Cunningham F. et al.[106])

TABLE 10

Normalized read counts from mRNA expression levels.

| Cell Line | ASCL1 | DDC | GRP | HOXA10 |
|---|---|---|---|---|
| NCI-H1417 | 42666.4 | 16161.1 | 10935.2 | 3327.72 |
| NCI-H1876 | 34116.3 | 986.718 | 43.7461 | 2779.5 |
| NCI-H69 | 19902.1 | 25773.6 | 3256.24 | 4271.2 |
| NCI-H510A | 79879.7 | 19456.3 | 27861 | 2730.14 |
| NCI-H2227 | 4515.83 | 2005.02 | 645.86 | 2.59381 |
| NCI-H2029 | 127171 | 39070.6 | 1800.43 | 10.0396 |
| NCI-H146 | 59238.2 | 45308.8 | 426.015 | 2126.39 |
| NCI-H187 | 71323.6 | 4363.62 | 130.681 | 2448.85 |
| NCI-H2081 | 69670.9 | 29683.5 | 2.97459 | 3423.76 |
| NCI-H345 | 81805.8 | 16935.7 | 30601.3 | 263.11 |
| SHP-77 | 115523 | 71808.9 | 39002.6 | 4.72759 |
| NCI-H748 | 122007 | 27938.7 | 12773.8 | 3940.53 |
| DMS-114 | 59.1696 | 16.3227 | 12.242 | 1462.92 |
| NCI-H1048 | 38.9626 | 90.2292 | 0 | 1168.88 |
| NCI-H2171 | 1115.78 | 368.976 | 0 | 1248.61 |
| NCI-H446 | 13.1805 | 32.0098 | 11.2976 | 2818.75 |
| NCI-H82 | 577.05 | 486.304 | 9.30725 | 221.047 |

TABLE 10-continued

Normalized read counts from mRNA expression levels.

| Cell Line | ASCL1 | DDC | GRP | HOXA10 |
|---|---|---|---|---|
| SBC5 | 4.51028 | 13.5308 | 0 | 617.908 |
| NCI-H526 | 11.9576 | 38.2644 | 4.78305 | 4091.9 |

TABLE 11

Z-scores generated by GenePattern from normalized mRNA read counts.

| Cell Line | ASCL1 | DDC | GRP | HOXA10 |
|---|---|---|---|---|
| NCI-H1417 | 0.63 | 0.69 | 1.09 | 0.67 |
| NCI-H1876 | 0.57 | −0.24 | −0.34 | 0.6 |
| NCI-H69 | 0.42 | 0.85 | 0.78 | 0.78 |
| NCI-H510A | 0.8 | 0.76 | 1.34 | 0.59 |
| NCI-H2227 | 0.02 | 0 | 0.35 | −2.31 |
| NCI-H2029 | 0.93 | 0.99 | 0.62 | −1.82 |
| NCI-H146 | 0.72 | 1.04 | 0.25 | 0.48 |
| NCI-H187 | 0.77 | 0.26 | −0.06 | 0.54 |
| NCI-H2081 | 0.77 | 0.9 | −0.98 | 0.69 |
| NCI-H345 | 0.81 | 0.71 | 1.36 | −0.43 |
| SHP-77 | 0.9 | 1.19 | 1.43 | −2.11 |
| NCI-H748 | 0.92 | 0.88 | 1.13 | 0.75 |
| DMS-114 | −1.16 | −1.59 | −0.66 | 0.32 |
| NCI-H1048 | −1.27 | −1.04 | −1.34 | 0.22 |
| NCI-H2171 | −0.36 | −0.57 | −1.34 | 0.25 |
| NCI-H446 | −1.55 | −1.38 | −0.68 | 0.6 |
| NCI-H82 | −0.54 | −0.48 | −0.73 | −0.51 |
| SBC5 | −1.81 | −1.65 | −1.34 | −0.06 |
| NCI-H526 | −1.58 | −1.32 | −0.88 | 0.76 |

Figure 5:
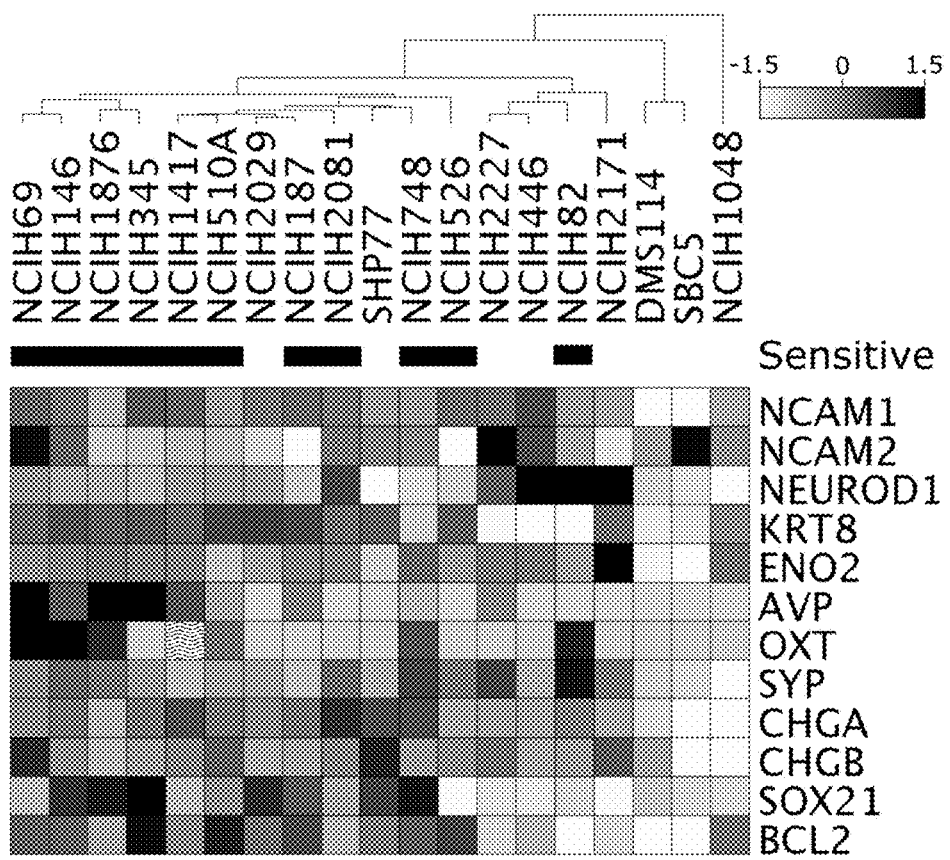
FIG. 5: Heat Map showing mRNA expression (as z-scores) for the neuroendocrine genes of Example 7 in the 19 cell lines of Table 6. Sensitive cell-lines display a stronger expression (higher z-score) of such neuroendocrine markers.

Example 7. Neuroendocrine Gene Panel to Predict Response to LSD1 Inhibition mRNA expression levels for a second set of genes according to Table 12 (NCAM1, NCAM2, NEUROD1, KRT8, ENO2, AVP, OXT, SYP, CHGA, CHGB, SOX21, BCL2) that includes genes representative of a neuroendocrine phenotype and that are used as immunohistochemical markers for diagnosing lung neuroendocrine tumors are strongly downregulated in resistant cell lines DMS114, SBC5, and NCI-H1048, as illustrated in FIG. 5. This is an agreement with our hypothesis that an LSD1 inhibition therapy stops cellular growth in tumors of neuroendocrine origin.

Tables 13A and 14B list normalized read counts of the genes of Table 12 across the 19 cell lines of Table 6 described.

TABLE 12

Genes of the second neuroendocrine gene panel

| Ensembl Gene ID* | Gene |
|---|---|
| ENSG00000149294 | NCAM1 |
| ENSG00000154654 | NCAM2 |
| ENSG00000162992 | NEUROD1 |
| ENSG00000170421 | KRT8 |
| ENSG00000111674 | ENO2 |
| ENSG00000101200 | AVP |
| ENSG00000101405 | OXT |
| ENSG00000102003 | SYP |
| ENSG00000100604 | CHGA |
| ENSG00000089199 | CHGB |
| ENSG00000125285 | SOX21 |
| ENSG00000171791 | BCL2 |

(*http://www.ensembl.org/, Cunningham F. et al.[106]).

TABLE 13A

Normalized read counts from mRNA expression levels.

| Cell Line | NCAM1 | NCAM2 | NEUROD1 | KRT8 | ENO2 | AVP |
|---|---|---|---|---|---|---|
| NCI-H1417 | 52961.1 | 230.0 | 257.7 | 32261.1 | 32287.3 | 5.8 |
| NCI-H1876 | 12131.4 | 111.0 | 143.4 | 36460.8 | 37021.4 | 33.2 |
| NCI-H69 | 53702.4 | 16861.8 | 295.0 | 28560.6 | 28765.0 | 18.6 |
| NCI-H510A | 21010.6 | 197.4 | 255.2 | 67662.7 | 11901.4 | 1.7 |
| NCI-H2227 | 42956.2 | 32469.4 | 1273.6 | 181.6 | 35558.6 | 2.6 |
| NCI-H2029 | 37343.8 | 70.3 | 244.3 | 76401.1 | 22753.0 | 0.0 |
| NCI-H146 | 39176.8 | 1929.1 | 173.4 | 50190.4 | 32430.6 | 5.5 |
| NCI-H187 | 47022.6 | 8.5 | 31.3 | 61809.4 | 32195.9 | 2.8 |
| NCI-H2081 | 37569.1 | 1279.1 | 2427.3 | 26842.7 | 32137.5 | 0.0 |
| NCI-H345 | 62260.5 | 131.6 | 96.7 | 46256.4 | 32848.5 | 45.6 |
| SHP-77 | 21787.1 | 990.4 | 0.0 | 35148.0 | 8851.6 | 0.0 |
| NCI-H748 | 21844.8 | 892.7 | 12.1 | 1508.8 | 44468.6 | 0.9 |
| DMS-114 | 95.9 | 512.1 | 18.4 | 377.5 | 3260.5 | 0.0 |
| NCI-H1048 | 14740.2 | 760.8 | 0.0 | 12726.4 | 38304.4 | 0.0 |
| NCI-H2171 | 16524.2 | 35.4 | 60402.8 | 26223.8 | 212034.0 | 0.0 |
| NCI-H446 | 79657.4 | 3747.0 | 19164.5 | 45.2 | 36229.5 | 0.0 |
| NCI-H82 | 20878.5 | 437.4 | 34283.3 | 27.9 | 22702.7 | 0.0 |
| SBC-5 | 130.8 | 19026.6 | 9.0 | 640.5 | 160.1 | 0.0 |
| NCI-H526 | 44561.3 | 0.0 | 23.9 | 38233.3 | 24912.5 | 0.0 |

TABLE 13B

Normalized read counts from mRNA expression levels.

| Cell Line | OXT | SYP | CHGA | CHGB | SOX21 | BCL2 |
|---|---|---|---|---|---|---|
| NCI-H1417 | NA | 6220.2 | 44388.5 | 11152.1 | 20.4 | 6170.7 |
| NCI-H1876 | 4.2 | 13216.2 | 7061.0 | 3968.7 | 1201.4 | 4126.7 |
| NCI-H69 | 9.5 | 10950.9 | 16527.4 | 52724.6 | 20.9 | 10853.4 |
| NCI-H510A | 1.8 | 9116.9 | 22660.3 | 20808.2 | 79.1 | 27378.7 |
| NCI-H2227 | 0.0 | 19962.0 | 11537.3 | 14927.4 | 2.6 | 1136.1 |
| NCI-H2029 | 0.0 | 8905.1 | 16397.9 | 5776.1 | 786.4 | 8687.6 |
| NCI-H146 | 16.9 | 14940.0 | 22829.6 | 9597.3 | 660.2 | 10340.5 |
| NCI-H187 | 0.0 | 5696.0 | 23923.2 | 6804.0 | 264.2 | 14934.6 |
| NCI-H2081 | 0.0 | 14334.6 | 79374.1 | 10934.6 | 44.6 | 2778.3 |
| NCI-H345 | 0.0 | 9686.8 | 22971.1 | 7702.7 | 4953.5 | 39332.3 |
| SHP-77 | 0.0 | 7861.2 | 47453.1 | 61511.4 | 480.6 | 7364.0 |
| NCI-H748 | 2.7 | 19958.6 | 46176.5 | 7932.8 | 1408.9 | 11595.8 |
| DMS-114 | 0.0 | 4299.0 | 1897.5 | 6161.8 | 10.2 | 185.7 |
| NCI-H1048 | 0.0 | 260.6 | 16.4 | 6.2 | 4.1 | 8063.2 |
| NCI-H2171 | 0.0 | 12335.6 | 9407.4 | 23159.9 | 0.0 | 1065.6 |
| NCI-H446 | 0.0 | 7403.7 | 10702.6 | 5688.3 | 1.9 | 2398.9 |
| NCI-H82 | 4.7 | 31714.5 | 19382.3 | 7303.9 | 4.7 | 148.9 |
| SBC-5 | 0.0 | 3642.1 | 311.2 | 203.0 | 4.5 | 306.7 |
| NCI-H526 | 0.0 | 12538.8 | 9920.1 | 9877.0 | 0.0 | 16511.1 |

Example 8. Signature Scores to Predictive Response to LSD1 Inhibition

Normalized expression levels (Norm_read_count) of ASCL1, DDC, GRP, and HOXA10 and MYC copy number variations (Copy_number_variation) were used to generate a gene signature to predict response to an LSD1 inhibition therapy as follows:

A score was generated from the following equation, obtained by partial least square (PLS) analysis using the second principal component:

$$\text{Signature Score 1} = $$
$$0.0900693 + \text{Norm\_read\_count}(ASCL1) \times 0.00000211296 +$$
$$\text{Norm\_read\_count}(DDC) \times 0.000000536658 +$$
$$\text{Norm\_read\_count}(GRP) \times 0.00000297345 +$$
$$\text{Norm\_read\_count}(HOXA10) \times 0.000234721 -$$
$$\text{Copy\_number\_variation}(MYC) \times 0.0537056$$

Figure 6:
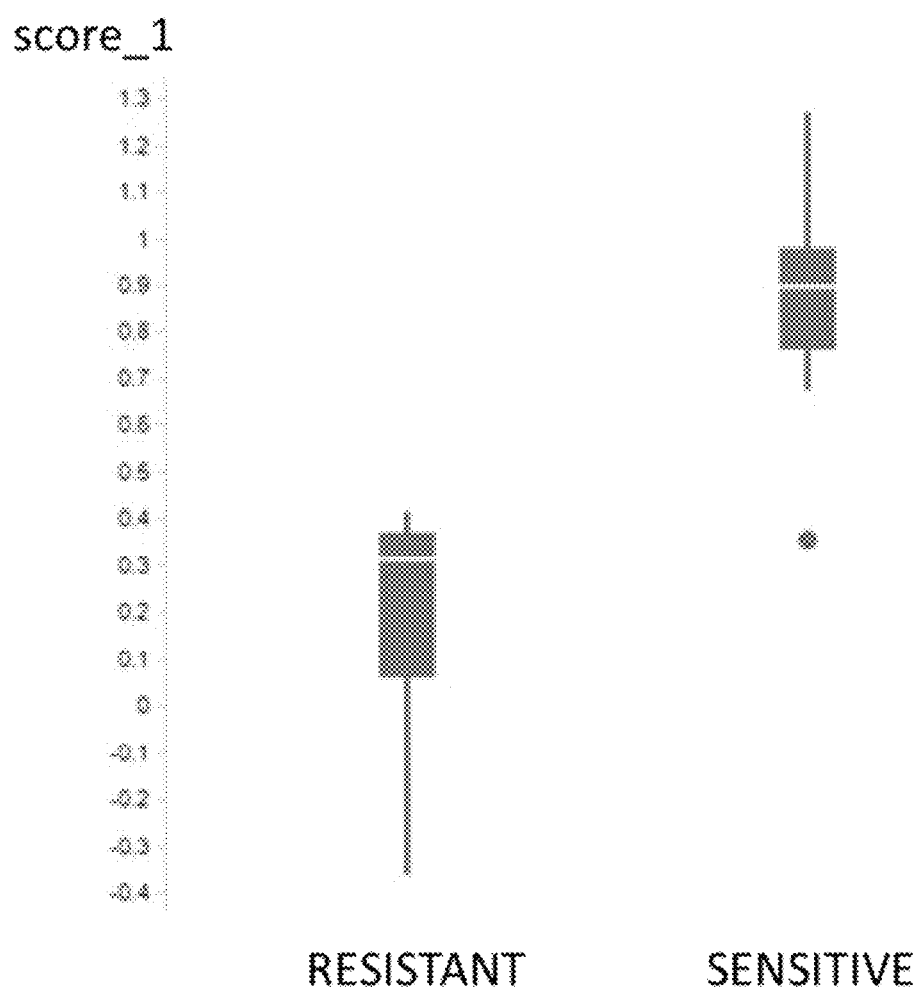
FIG. 6: Signature scores obtained by PLS analysis using the second principal component according to Example 8. Cell lines with score_1>0.5 are more likely to be sensitive to an LSD1 inhibition therapy.

A Signature Score 1>0.5 predicts response to an LSD1 inhibition therapy (Fisher's exact test two-tailed p 0.0001, sensitivity 90%, specificity 100%) as depicted in FIG. 6.

Alternatively, a score was generated from the following equation, obtained by partial least square analysis using the first principal component:

$$\text{Signature Score 2} =$$
$$0.483918 + \text{Norm\_read\_count}(ASCL1) \times 0.00000188066 +$$
$$\text{Norm\_read\_count}(DDC) \times 0.00000188066 +$$
$$\text{Norm\_read\_count}(GRP) \times 0.00000352033 -$$
$$\text{Copy\_number\_variation}(MYC) \times 0.0407898$$

Figure 7:
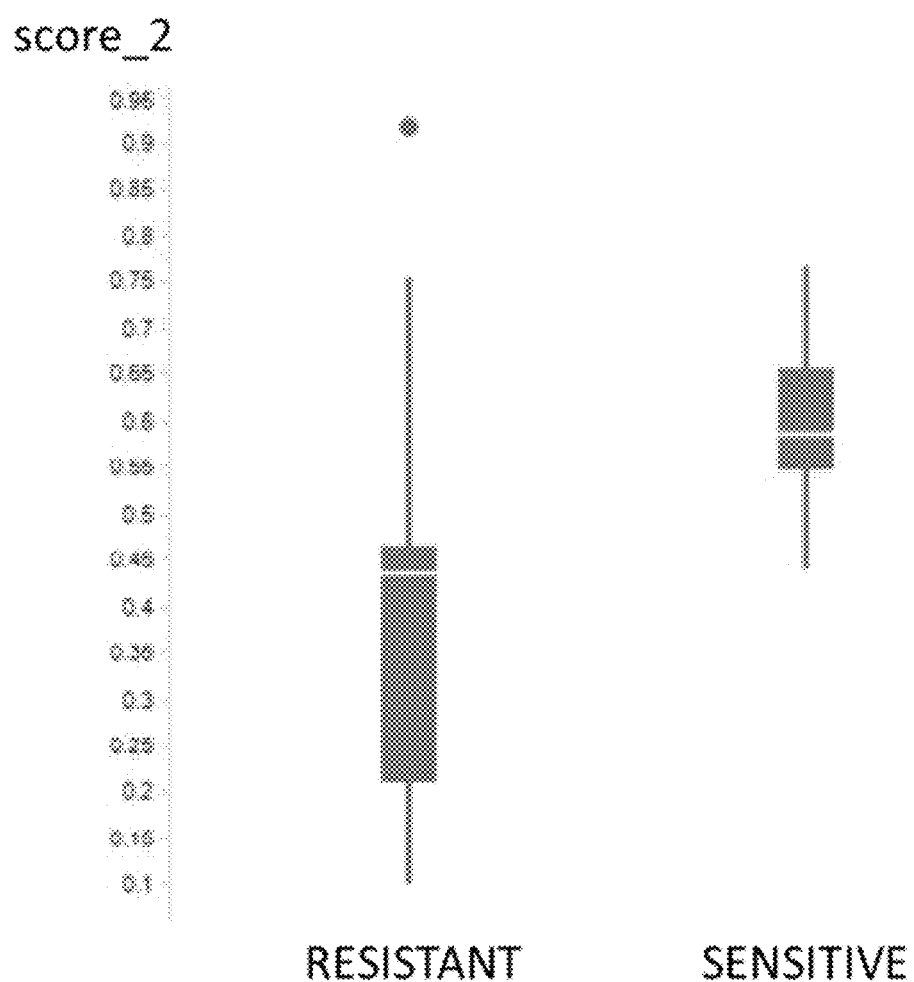
FIG. 7: Signature scores obtained by PLS analysis using the first principal component according to Example 8. Cell lines with score_2>0.5 are more likely to be sensitive to an LSD1 inhibition therapy.

A Signature Score 2>0.5 predicts response to an LSD1 inhibition therapy (Fisher's exact test two-tailed p 0.0055, sensitivity 90%, specificity 77.8%) as depicted in FIG. 7.

Further, a score was generated from the following equation, obtained by partial least square analysis using the first principal component:

$$\text{Signature Score 3} =$$
$$0.393569 + \text{Norm\_read\_count}(ASCL1) \times 0.00000182731 +$$
$$\text{Norm\_read\_count}(DDC) \times 0.00000189664 +$$
$$\text{Norm\_read\_count}(GRP) \times 0.00000342046$$

Figure 8:
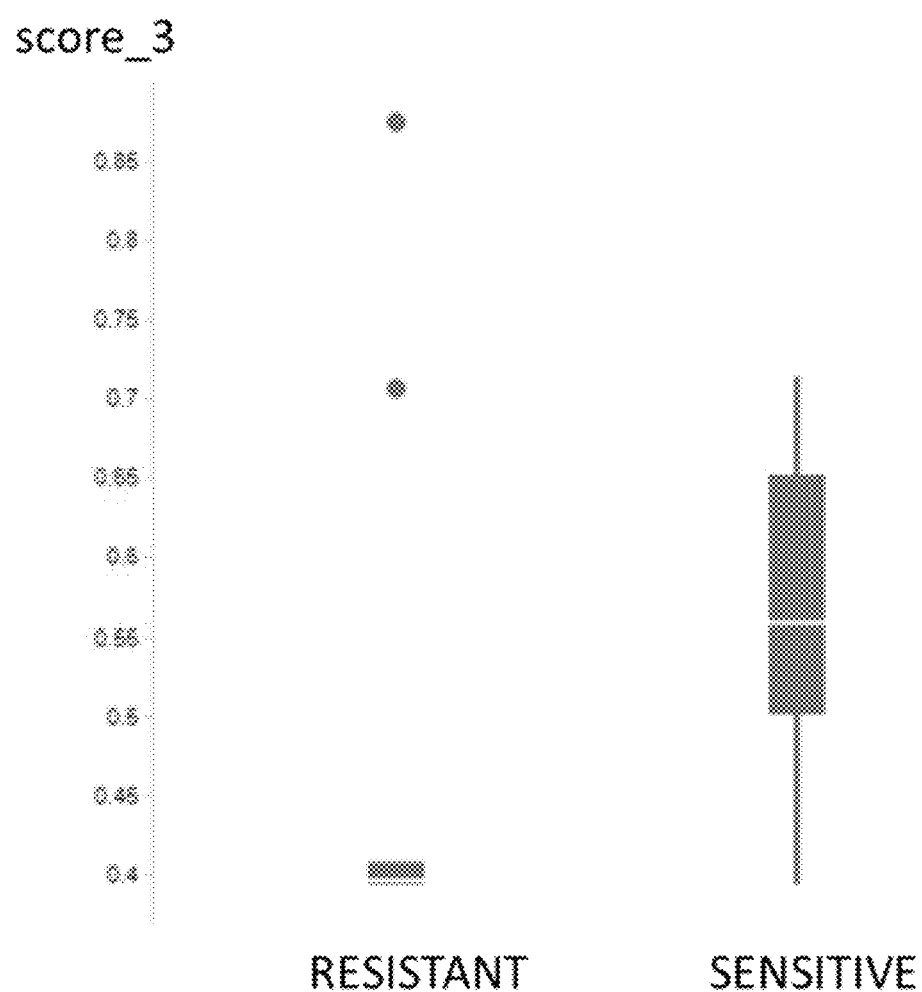
FIG. 8: Signature scores obtained by PLS analysis using the first principal component according to Example 8. Cell lines with score_3>0.45 are more likely to be sensitive to an LSD1 inhibition therapy.

A Signature Score 3>0.45 predicts response to an LSD1 inhibition therapy (Fisher's exact test two-tailed p 0.0055, sensitivity 90%, specificity 77.8%) as depicted in FIG. 8.

A signature score above the reference level indicates a high likelihood of response to treatment with an LSD1 inhibitor, whereas a signature score below said level indicates a lower likelihood to respond to such treatment. A higher score is associated with higher mRNA expression of ASCL1, DDC, GRP, HOXA10, and with lower copy number variations in MYC.

Example 9. In Vivo Tumor Growth Inhibition

NCI-H510A Models:
7-8-week old athymic nude mice animals were injected with 5×10$^6$ H510A cells resuspended in 100 μL of 1:1 mixture of Matrigel® matrix (Corning Inc., Tewksbury/MA, C. S. Hughes et al.[113]) and PBS. Tumors were staged at 200-300 mm$^3$ animals and distributed into dosing groups.

(trans)-N1-((1R,2S)-2-phenylcyclopropyl)cyclohexane-1,4-diamine was administered at a dose of 40 µg per kg (upk) five days on/two days off until end of study. Tumor volume was measure biweekly using a digital caliber. The study was concluded when mean tumor volume within control group reached 2000 mm³ or 28 days post-staging. Statistical analysis was performed using unpaired t-test.

NCI-H526 and SHP-77 Models:

8-12-week old nu/nu mice were injected with 1×10⁷ H526 cells or 5×10⁶ SHP-77 resuspended in 100 µL of 1:1 mixture of Matrigel® and PBS. Tumors were staged at 100-150 mm³ animals and distributed into dosing groups. (trans)-N1-((1R,2S)-2-phenylcyclopropyl)cyclohexane-1,4-diamine was administered at a dose of 40 upk five days on/two days off until end of study. Tumor volume was measure biweekly using a digital caliber. The study was concluded when mean tumor volume within control group reached 2000 mm³ or 28 days post-staging. Statistical analysis was performed using unpaired t-test.

Figure 9:
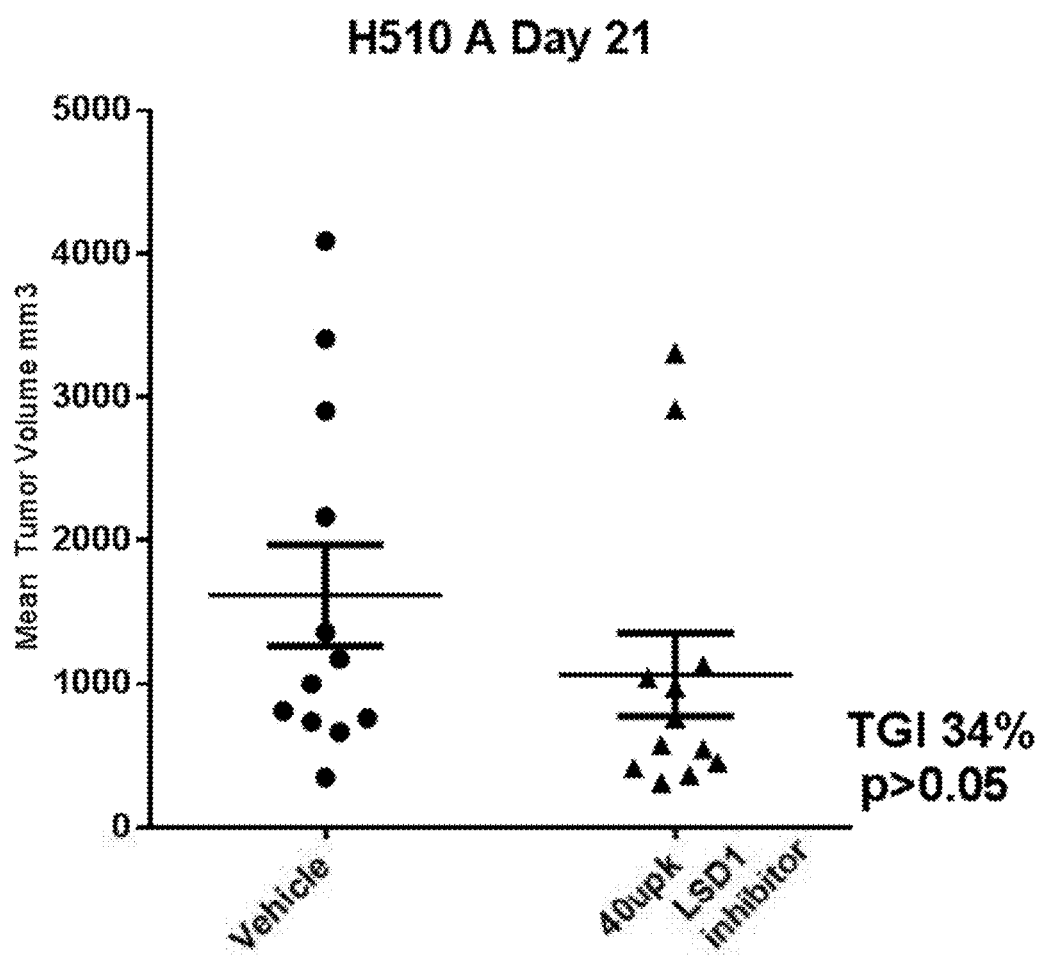
FIG. 9: in vivo tumor growth inhibition of (trans)-N1-((1R,2S)-2-phenylcyclopropyl)cyclohexane-1,4-diamine in classic (C) cell line H-510A.

The in vitro activity of the LSD1 inhibitor (trans)-N1-((1R,2S)-2-phenylcyclopropyl)cyclohexane-1,4-diamine translated into in vivo growth inhibition in the H510A xenograft model as shown in FIG. 9. Treatment of (trans)-N1-((1R,2S)-2-phenylcyclopropyl)cyclohexane-1,4-diamine in the "responsive signature" positive cell line H510A model resulted in a modest but measurable tumor growth inhibition of 34% compared to untreated controls after 21 days of dosing. These results suggest that the 15 gene response signature as previously defined may predict in vivo sensitivity to (trans)-N1-((1R,2S)-2-phenylcyclopropyl)cyclohexane-1,4-diamine. The in vivo activity of (trans)-N1-((1R,2S)-2-phenylcyclopropyl)cyclohexane-1,4-diamine has also been assessed in the "response signature positive" SHP-77 and "response signature negative" H526 xenografts to validate the predictability of the gene signature from in vitro results.

Example 10. Expression Patterns in SCLC Patient Samples

Gene expression patterns in a set of SCLC patient samples were found to be similar to those observed in SCLC cell lines (Example 6, FIG. 4), suggesting that use of LSD1 inhibitor response gene signature, particularly the use of the (trans)-N1-((1R,2S)-2-phenylcyclopropyl)cyclohexane-1,4-diamine response gene signature, may increase the likelihood of identifying patients who will clinically benefit from LSD1 inhibitor based therapies, particularly from (trans)-N1-((1R,2S)-2-phenylcyclopropyl)cyclohexane-1,4-diamine based therapies.

Figure 10:
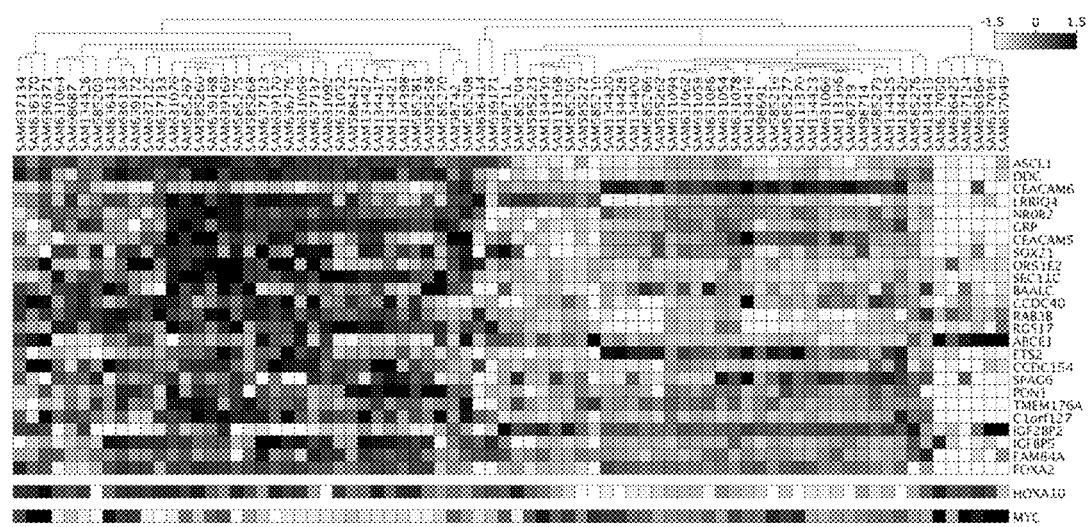
FIG. 10: Heat Map showing mRNA expression (as z-scores) patterns in SCLC patient samples.

FIG. 10 provides a Heat Map showing mRNA expression (as z-scores) patterns in SCLC patient samples comprising the genes of Table 8, Table 9 and MYC. Higher z-scores correlate with better sensitivity.

The dataset used corresponds to the dataset EGAD00001000223 obtained from European Genome-phenome Archive (EGA) of the The European Bioinformatics Institute, Part of the European Molecular Biology Laboratory (EMBL-EBI, Hinxton/UK, https://www.ebi.ac.uk/ega/datasets/EGAD00001000223). The patient ID (SAMxxxxxx) corresponds to the ID used in this dataset.

[1] Shi et al. (2004) Cell 119:941
[2] WO 2011/131697 A1
[3] WO 2012/135113 A2
[4] WO 2013/057322 A1
[5] WO 2010/143582
[6] WO 2011/131576
[7] WO 2013/022047
[8] WO 2013/025805
[9] WO 2014/058071
[10] WO 2014/084298
[11] WO 2014/085613
[12] WO 2014/086790
[13] WO2014/164867
[14] WO 2014/194280
[15] WO 2014/205213
[16] WO 2015/021128
[17] WO 2015/031564
[18] WO 2015/089192
[19] WO 2015/120281
[20] WO 2015/123465
[21] WO 2015/123437
[22] WO 2015/123424
[23] WO 2015/123408
[24] WO 2015/134973
[25] WO 2015/156417
[26] WO 2016/004105
[27] WO 2016/007722
[28] WO 2016/007727
[29] WO 2016/007731
[30] WO 2016/007736
[31] WO 2016/034946
[32] WO 2016/037005
[33] CN 105541806
[34] WO 2016/123387
[35] WO 2016/130952
[36] CN 105924362
[37] CN 105985265
[38] WO 2016/161282
[39] CN 106045862
[40] CN 106045881
[41] WO 2016/172496
[42] WO 2016/177656
[43] WO 2017/004519
[44] WO 2017/027678
[45] WO 2010/138588 A2
[46] US 2007/0027135 A1
[47] WO 2005/049594 A1
[48] US 2006/0229289 A1
[49] WO 2011/091213 A2
[50] WO 2009/040517 A2
[51] DD 159877 A1
[52] WO 2006/000420 A1
[53] WO 2012/129353 A1
[54] ES 544159 A1
[55] WO 2007/015632 A1
[56] Rosenberg B. et al. Nature (1969) 222(5191):385-6
[57] WO 2013/120104 A2
[58] WO 2014/134583 A2
[59] EP 253738 A1
[60] DE 2510866 A1
[61] Daigle S. R. et al. Cancer Cell (2011) 20(1):53-65
[62] WO 2012/118812 A2
[63] WO 2012/075381 A2
[64] WO 2012/142504 A1
[65] CH 514578 A
[66] WO 2013/178821 A1
[67] U.S. Pat. No. 2,802,005
[68] WO 2006/028958 A2
[69] GB 2136425
[70] WO 2011/140324 A1
[71] WO 2011/054843 A1
[72] WO 2011/140325 A1
[73] WO 2012/052390 A1

[74] U.S. Pat. No. 6,121,451 A
[75] WO 2011/143651 A1
[76] WO 99/35146 A1
[77] WO 2010/033481 A1
[78] WO 2006/105262 A1
[79] WO 2013/016081 A1
[80] U.S. Pat. No. 2,331,725
[81] WO 2002/081435 A1
[82] WO 2008/063525 A1
[84] US 2005/0282803
[85] WO 2004/106328 A1
[86] U.S. Pat. No. 5,712,274 A
[87] EP 253739 A1
[88] WO 2002/022577 A2
[89] EP 432677 A1
[90] US 2007/0265272 A1
[91] US 2005/0215610 A1
[92] WO 93/07148 A1
[93] Yu et al., Nature Communications (2012) 3(1288):1-11
[94] JP 10152462 A
[95] WO 2010/147917 A1
[96] DE 3231255 A1
[97] EP 321122 A2
[98] WO 2006/023778 A2
[99] BE 624076
[100] S. P. Parker, Ed., McGraw-Hill Dictionary of Chemical Terms (1984) McGraw-Hill Book Company, New York
[101] Eliel, E. and Wilen, S., "Stereochemistry of Organic Compounds", John Wiley & Sons, Inc., New York, 1994
[102] Cahn et al. Angew. Chem. Inter. Edit. 1966, 5, 385; errata 511
[103] Ansel's Pharmaceutical Dosage Forms and Drug Delivery Systems (2004) Lippincott, Williams & Wilkins, Philadelphia
[104] Rowe R. C, Handbook of Pharmaceutical Excipients (2005) Pharmaceutical Press, Chicago
[105] Remington: The Science and Practice of Pharmacy (2000) Lippincott, Williams & Wilkins, Philadelphia
[106] Cunningham F. et al., Nucl. Acids Res. (2015) 43(D1): D662-D669
[107] Mortazavi et al. Nat Methods (2008) 5(7):621-8
[108] Selzer et al., Genes Chromosomes Cancer (2005) 44(3): 305-319
[109] Reich M. et al., Nature Genetics (2006) 38(5): 500-501
[110] Desmond et al., Cancer Res (1985) 45(6):2913-2923
[111] Shoemaker R. H., Nature Reviews Cancer (2016) 6:813-823
[112] Augustyn et al., Proc Natl Acad Sci USA (2014) 111 (41):14788-93
[113] Hughes et al., Proteomics (2010) 10(9):1886-90

The invention claimed is:

1. A therapeutic combination comprising an LSD1 inhibitor, wherein the LSD1 inhibitor is (trans)-N1-((1R,2S)-2-phenylcyclopropyl)cyclohexane-1,4-diamine or a pharmaceutically acceptable salt thereof, and one or more active pharmaceutical ingredients selected from the list of ABT-199, ABT-263, ABT-737 Belinostat, Bendamustine, BGJ398, Carboplatin, Cisplatin, CPI-203, Docetaxel, Doxorubicin, EPZ-5676, EPZ-6438, Etoposide, Gemcitabine, GSK126, GSK1324726A, GSK1210151A, Irinotecan, (+)-JQ1, Lapatinib, LY2603618, MLN8237, OTX015, Paclitaxel, Panobinostat, SGC 0946, Temozolomide, Topotecan, Vincristine and pharmaceutically acceptable salts thereof.

2. The therapeutic combination according to claim 1 comprising the LSD1 inhibitor or a pharmaceutically acceptable salt thereof and one BCL2 inhibitor selected from the list of ABT-199, ABT-263, ABT-737 and a pharmaceutically acceptable salt thereof.

3. The therapeutic combination according to claim 1 comprising the LSD1 inhibitor or a pharmaceutically acceptable salt thereof and one BET inhibitor selected from the list of CPI-203, GSK1324726A, GSK1210151A, (+)-JQ1, OTX015 and a pharmaceutically acceptable salt thereof.

4. The therapeutic combination according to claim 1 comprising the LSD1 inhibitor or a pharmaceutically acceptable salt thereof and one EZH2 inhibitor selected from the list of EPZ-6438, GSK126 and a pharmaceutically acceptable salt thereof.

5. The therapeutic combination according to claim 1 comprising the LSD1 inhibitor or a pharmaceutically acceptable salt thereof and one DOT1L inhibitor selected from the list of EPZ-5676, SGC 0946 and a pharmaceutically acceptable salt thereof.

6. The therapeutic combination according to claim 1 comprising the LSD1 inhibitor or a pharmaceutically acceptable salt thereof and one Chk inhibitor selected from LY2603618 and a pharmaceutically acceptable salt thereof.

7. The therapeutic combination according to claim 1 comprising the LSD1 inhibitor or a pharmaceutically acceptable salt thereof and one DNA alkylating agent selected from the list of Bendamustine, Carboplatin, Cisplatin, Temozolomide and a pharmaceutically acceptable salt thereof.

8. The therapeutic combination according to claim 1 comprising the LSD1 inhibitor or a pharmaceutically acceptable salt thereof and one HDAC inhibitor selected from the list of Belinostat, Panobinostat, and a pharmaceutically acceptable salt thereof.

9. The therapeutic combination according to claim 1 comprising the LSD1 inhibitor or a pharmaceutically acceptable salt thereof and one topoisomerase inhibitor selected from the list of Etoposide, Irinotecan, Topotecan and a pharmaceutically acceptable salt thereof.

10. The therapeutic combination according to claim 1 comprising the LSD1 inhibitor or a pharmaceutically acceptable salt thereof and one Aurora kinase inhibitor selected from the list of MLN8237 and a pharmaceutically acceptable salt thereof.

11. The therapeutic combination according to claim 1 comprising the LSD1 inhibitor or a pharmaceutically acceptable salt thereof and one anti-mitotic agent selected from the list of Docetaxel, Paclitaxel, Vincristine and a pharmaceutically acceptable salt thereof.

12. The therapeutic combination according to claim 1 comprising the LSD1 inhibitor or a pharmaceutically acceptable salt thereof, Etoposide or a pharmaceutically acceptable salt thereof, and Carboplatin or a pharmaceutically acceptable salt thereof.

13. A pharmaceutical composition comprising a therapeutic combination according to claim 1 and one or more pharmaceutically acceptable excipients.

14. The therapeutic combination according to claim 1 comprising (trans)-N1-((1R,2S)-2-phenylcyclopropyl)cyclohexane-1,4-diamine or a pharmaceutically acceptable salt thereof, Etoposide or a pharmaceutically acceptable salt thereof, and Carboplatin or Cisplatin or a pharmaceutically acceptable salt thereof.

* * * * *